US008679097B2

(12) United States Patent
Jorgensen et al.

(10) Patent No.: US 8,679,097 B2
(45) Date of Patent: Mar. 25, 2014

(54) METHOD AND DEVICES FOR MINIMALLY INVASIVE ARTHROSCOPIC PROCEDURES

(75) Inventors: Glen Jorgensen, Jacksonville, FL (US); William G. Dennis, Jacksonville, FL (US)

(73) Assignee: OrthoDynamix LLC, Jacksonville, FL (US)

( * ) Notice: Subject to any disclaimer, the term of this patent is extended or adjusted under 35 U.S.C. 154(b) by 1026 days.

(21) Appl. No.: 12/399,471

(22) Filed: Mar. 6, 2009

(65) Prior Publication Data

US 2009/0171159 A1 Jul. 2, 2009

Related U.S. Application Data

(63) Continuation-in-part of application No. 12/119,799, filed on May 13, 2008, which is a continuation of application No. 11/643,740, filed on Dec. 20, 2006.

(60) Provisional application No. 60/752,284, filed on Dec. 20, 2005.

(51) Int. Cl.
*A61B 17/00* (2006.01)

(52) U.S. Cl.
USPC ............................................................ 606/1

(58) Field of Classification Search
USPC ............................................................ 606/1
See application file for complete search history.

(56) References Cited

U.S. PATENT DOCUMENTS

| 5,306,245 | A | 4/1994 | Heaven |
| 5,318,528 | A | 6/1994 | Heaven et al. |
| 5,322,505 | A | 6/1994 | Krause et al. |
| 5,411,514 | A | 5/1995 | Fucci et al. |
| 5,439,478 | A | 8/1995 | Palmer |
| 5,454,827 | A | 10/1995 | Aust et al. |
| 5,507,297 | A | 4/1996 | Slater et al. |
| 5,510,070 | A | 4/1996 | Krause et al. |
| 5,618,293 | A | 4/1997 | Sample et al. |
| 5,618,294 | A | 4/1997 | Aust et al. |
| 5,643,294 | A | 7/1997 | Tovey et al. |
| 5,643,303 | A | 7/1997 | Donahue |
| 5,766,196 | A | 6/1998 | Griffiths |
| 5,782,834 | A | 7/1998 | Lucey et al. |
| 5,797,959 | A | 8/1998 | Castro et al. |
| 5,836,960 | A | 11/1998 | Kolesa et al. |
| 5,899,914 | A * | 5/1999 | Zirps et al. .................. 606/170 |
| 5,938,678 | A | 8/1999 | Zirps et al. |
| 6,228,023 | B1 * | 5/2001 | Zaslavsky et al. ............ 600/204 |
| 6,352,503 | B1 | 3/2002 | Matsui et al. |

(Continued)

FOREIGN PATENT DOCUMENTS

| EP | 1586275 A2 | 10/2005 |
| EP | 06848010.2 | 1/2010 |
| WO | WO 2005/086839 A2 | 9/2005 |

*Primary Examiner* — Bill Thomson
*Assistant Examiner* — John R Downey
(74) *Attorney, Agent, or Firm* — Pandiscio & Pandiscio

(57) ABSTRACT

A surgical device is provided, the device having a tubular outer body member with a handle at its proximal end and a flexible distal end segment extending from its distal end. The surgical device also has an operable end extending from the distal end of the flexible distal end segment. The device is configured for selectively causing the flexible end segment to bend to adopt a desired curvature and for selectively rotating the operable end relative to the flexible distal end segment about an axis of the flexible distal end segment.

15 Claims, 40 Drawing Sheets

(56) References Cited

U.S. PATENT DOCUMENTS

| | | |
|---|---|---|
| 6,423,059 B1 | 7/2002 | Hanson et al. |
| 6,464,711 B1 | 10/2002 | Emans et al. |
| 6,500,189 B1 | 12/2002 | Lang et al. |
| 6,533,749 B1 | 3/2003 | Mitusina et al. |
| 6,569,105 B1 | 5/2003 | Kortenbach et al. |
| 6,645,218 B1 | 11/2003 | Cassidy et al. |
| 6,656,195 B2 | 12/2003 | Peters et al. |
| 6,695,772 B1 | 2/2004 | Bon et al. |
| 6,743,239 B1 | 6/2004 | Kuehn et al. |
| 7,033,357 B2 | 4/2006 | Baxter et al. |
| 7,090,637 B2 | 8/2006 | Danitz et al. |
| 7,090,683 B2 * | 8/2006 | Brock et al. .......... 606/130 |
| 7,147,650 B2 | 12/2006 | Lee |
| 7,169,141 B2 | 1/2007 | Brock et al. |
| 7,214,230 B2 | 5/2007 | Brock et al. |
| 7,229,456 B2 | 6/2007 | Lang et al. |
| 7,303,560 B2 | 12/2007 | Chin et al. |
| 7,338,513 B2 | 3/2008 | Lee et al. |
| 7,364,582 B2 | 4/2008 | Lee |
| 7,371,210 B2 | 5/2008 | Brock et al. |
| 7,585,300 B2 | 9/2009 | Cha |
| 2003/0135204 A1 * | 7/2003 | Lee et al. .......... 606/1 |
| 2004/0102772 A1 | 5/2004 | Baxter et al. |
| 2004/0138525 A1 | 7/2004 | Saadat et al. |
| 2005/0043682 A1 | 2/2005 | Kucklick et al. |
| 2005/0119527 A1 | 6/2005 | Banik et al. |
| 2005/0159765 A1 | 7/2005 | Moutafis et al. |
| 2005/0187543 A1 | 8/2005 | Underwood et al. |
| 2005/0197623 A1 | 9/2005 | Leeflang et al. |
| 2005/0209622 A1 | 9/2005 | Carrison |
| 2005/0216033 A1 | 9/2005 | Lee et al. |
| 2006/0095074 A1 | 5/2006 | Lee et al. |

* cited by examiner

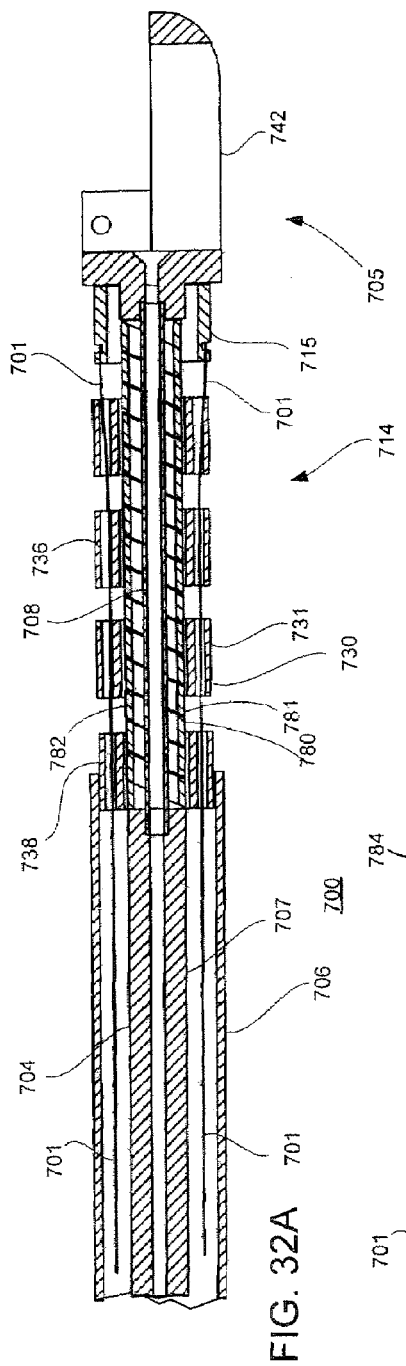
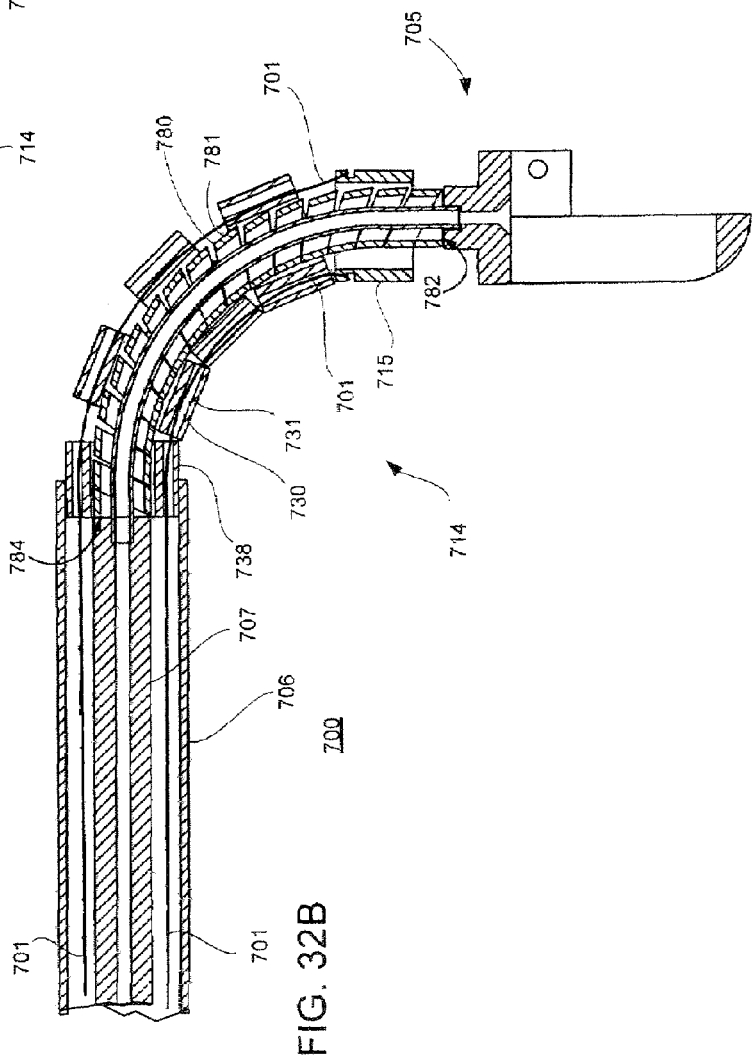
FIG. 32A
FIG. 32B

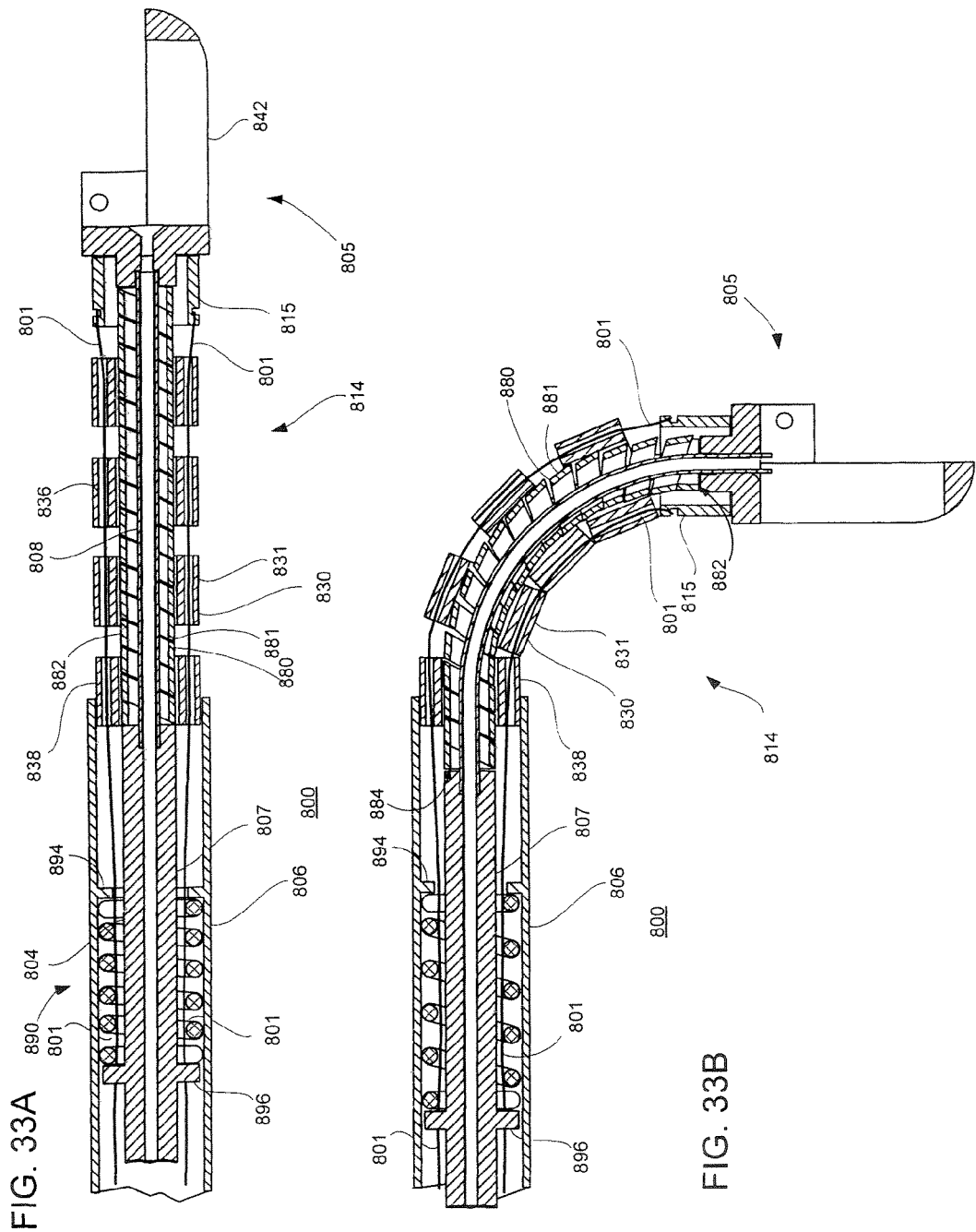

METHOD AND DEVICES FOR MINIMALLY INVASIVE ARTHROSCOPIC PROCEDURES

CROSS-REFERENCE TO RELATED APPLICATIONS

The present application is a continuation-in-part of U.S. patent application Ser. No. 12/119,799, filed on May 13, 2008, which is a continuation of U.S. patent application Ser. No. 11/643,740, filed Dec. 20, 2006, which claims the benefit of U.S. provisional application 60/752,284, filed Dec. 20, 2005, each of which is incorporated herein by reference in its entirety.

FIELD OF THE INVENTION

The present invention relates generally to devices and methods for performing arthroscopic procedures, particularly arthroscopic procedures on the hip, including arthroscopic diagnostic and surgical procedures.

BACKGROUND OF THE INVENTION

Access to the knee and shoulder capsules during arthroscopic surgery is typically made through opposing portals often called the operative portal and the visualization portal. The arthroscope is typically inserted through the visualization portal, while the medical device is inserted through the operative portal. The visualization portal can be readily interchanged with the operative portal to provide an enhanced view of and access to internal capsular structures.

The hip is complex and difficult to access using arthroscopic techniques. FIGS. 1 and 2 illustrate the basic anatomy of the hip. For the sake of simplification, the figures do not show the surrounding synovial membrane, the femor ligament complex, the tough adductor muscle structure, varying layers of fat, and other tissue, which all compound the difficulty in accessing the joint capsule. There are also many delicate structures surrounding the joint that are not shown in the figures, i.e., the anterior femoral neurovascular bundle, the lateral femoral cutaneous nerve, the lateral femoral circumflex artery and the sciatic nerve, among others. Damage to these structures is permanent and irreparable Typically, access to the hip joint for minimally invasive arthroscopic surgery is through two cannulas positioned in the posterolateral and anterolateral positions that are located 1-2 cm above (superior) and 1-2 cm on each side of the landmark greater trocanter, as shown in FIG. 3. Typically, the arthroscope is in the posterolateral position and the operative device (e.g. forceps, dissector, scissors, scalpel, punch, probe, powered shaver, manual graspers, electrocautery wand, etc.) is in the anterolateral position. It is common to interchange these positions to improve visualization and/or access to the target site.

Despite the ability to interchange positions, parts of the distended surfaces of the hip joint can not be fully visualized. FIG. 3 shows this "No See" zone. The portions of the hip not accessible by straight and rigid operative instruments is even larger. For example, if the target site is in a region that is hidden on the far side of the femoral head, a third portal must often be established in the anterior position. Such an added portal considerably increases the risk of the procedure because the proximity of the lateral femoral cutaneous nerve, the lateral femoral circumflex artery, and the femoral neurovascular bundle. Access via the opposite, posterior side of the joint, i.e. the gluteal region, is not a viable option nor is the medial approach from the groin.

Roughly half of the distended hip joint is not accessible through the normal, accepted, portal placement positions. While the situation can be relieved somewhat through the use of 70 degree scopes and physically prying the cannulas into a contrived position, the access problem remains a significant hurdle to the performance of arthroscopic procedures on the hip.

SUMMARY OF THE INVENTION

The invention generally relates to devices and methods for performing arthroscopic procedures, particularly arthroscopic procedures on the hip. The devices and methods provide visualization and access to regions of the spherically-shaped hip joint that are inaccessible with the current technology of arthroscopic instrumentation.

The devices and methods can suitably be used to perform arthroscopic procedures not only on the hip, but also on other parts of the body that require flexible access, such as the knee and shoulder. The devices and methods are not limited to arthroscopy, and can further be used in endoscopic and laparoscopic procedures as well as open surgery.

In one aspect, the invention generally relates to a device for arthroscopic medical procedures and comprises a handle at a proximal end, an operable portion at a distal end, a body member extending between the handle and the operable end, the body member comprising an outer rigid member and an inner member slidably housed within outer rigid member, the inner member having flexibility along at least a portion of its length. As the inner member is retracted within outer rigid member, the inner member takes on the profile of the outer rigid member, and wherein as the inner member is extended outside the outer rigid member, the inner member takes on a curved profile.

In another aspect, the invention generally relates to an arthroscopic medical device for use in performing a medical procedure at a site within a patient comprising a handle for positioning outside of the patient, a body member extending from the handle, wherein at least a portion of the body member is inserted within the patient, the body member comprising an outer member having a position fixed relative to the handle and an inner member slidably and rotatably housed within outer member and having flexibility along at least a portion of its length, a rotation mechanism that causes inner member to rotate relative to outer member, an extension mechanism that causes inner member to extend outside of and retract within outer member and an operable end removably mounted on the inner member. The inner member has a distal end that takes on a predetermined arcuate path.

In another aspect, the invention generally relates to a device for arthroscopic medical procedures comprising a handle, a rigid outer tube extending from the handle, and a pre-bent flexible inner tube slidably received within the outer tube. The inner tube is disposed so as to advance out of the outer tube in an arcuate shaped path and so as to rotate about the linear axis of the rigid tube and/or the arcuate axis of the advancing flexible tube. The inner tube has an operable end at its distal end in the form of a visualization device, an electrical manipulation device, and/or a mechanical manipulation device.

In another aspect, the invention generally relates to a device for diagnostic or surgical procedures comprising a handle at a proximal end; an elongate body member extending from the handle, the elongate body member having a proximal end and a distal end; a flexible, steerable distal end segment extending from the distal end of the elongate body member; an operable end rotatably mounted to the distal end segment; a manipulation mechanism at the proximal end of the device for manipulating the distal end segment and rotating the operable end; wherein the device provides the following independent degrees of freedom including: linear translation along the linear axis of the elongated body member, rotation about the linear axis of the elongated body member, curvilinear bending of the flexible end segment to provide the flexible end segment with an arcuate axis, and rotation of the operable end about the arcuate axis of the flexible end segment.

In another aspect, the invention generally relates to a device for diagnostic or surgical procedures comprising a handle at a proximal end; an operable end at a distal end; an outer rigid or semi-rigid body member fixed relative to the handle; an inner body member slidably housed and rotatably positioned within the outer body member, the inner body member having flexibility along at least a portion of its length; and an pre-formed element, rotatably fixed to the handle and slidably fixed within the inner body member, the pre-formed element defining a bend radius; wherein as the inner body member is retracted within outer body member, the inner body member takes on the profile of the outer member, and wherein as the inner body member is extended outside the outer body member, the inner body member takes on a curved profile proportional to the bend radius of the pre-formed element, the curved profile providing the inner body member with an arcuate axis, and wherein the operable end is rotatable about the arcuate axis of the inner member.

In another aspect, the invention generally relates to a device for diagnostic or surgical procedures comprising a handle at a proximal end; an operable end rotatably mounted at a distal end; a rigid or semi-rigid elongate body member fixed relative to the handle and interconnected with the operable portion via a flexible distal portion; flexion control means for bending the flexible distal portion; one or more pairs of cables interconnecting the flexion control means and the flexible distal portion, wherein manipulation of flexion control means places a tensile force on one or more cables and causes the flexible distal portion to bend proportionally to the tensile force, wherein bending of the flexible distal portion provides the flexible distal portion with an arcuate axis; and rotation control means in connection with the operable portion for rotating the operative end about the arcuate axis of the flexible distal segment.

In another aspect, the invention generally relates to a device for diagnostic or surgical procedures comprising a handle; a rigid or semi-rigid tubular body member extending from the handle and having a proximal end and a distal end; and a flexible, steerable, distal end segment with an operable end rotatably mounted to the distal end of the body member, the operable end in the form of a visualization device, an electrical tissue manipulation device, and/or a mechanical tissue manipulation device.

Embodiments according to these aspects of the invention can include the following features. The device can be designed for use in medical procedures on the hip, for example, arthroscopic procedures on the hip, and the inner body member or the flexible distal segment/distal end segment takes on a curved profile having a bend radius corresponding to the curvature of the femoral head. In some embodiments, the bend radius can be approximately 25 mm. The device can be designed for use in medical procedures on the knee or shoulder, and the inner member can take on a curved profile having a bend radius less than 25 mm. In some embodiments, the bend radius can be approximately 12 mm. The device can be for use in medical procedures on the elbow, wrist, or intraverterbral spaces, and the inner member can take on a curved profile having a bend radius less than 12 mm. In some embodiments, the bed radius can range from about 1 mm to about 5 mm. The device can be for use in general abdominal laparoscopy, and the inner member can take on a curved profile having a bend radius ranging from about 25 mm to about 50 mm. The inner and outer members can have a cylindrical shape with a circular cross-section. The inner and outer members can be fabricated of a lightweight and strong bio-compatible material. The material can be selected from surgical grade stainless steel, anodized aluminum, and polymeric materials and composites. The operable end of the device can be in the form of gaspers, scissors, forceps, scalpels, punches, probes, dissectors, mono polar cautery, bi-polar ablation/cautery, CCD cameras and lens. The operable end can include a pair of arms, jaws, or elements movable with relation to each other, and the device can further include an actuation mechanism at its proximal end. The actuation mechanism can comprises a trigger, ring, or one or more actuating buttons on the handle. The actuation mechanism can comprise finger and thumb holes movable with relation to each other. The body member can be hollow and house apparatus that connects the actuation mechanism to the operable end. The apparatus that connects the actuation mechanism to the operable end can include one or more cables or push/pull rods in connection with a cam. The apparatus that connects the actuation mechanism to the operable end can include one or more push/pull rods in connection with a rack having ridges along at least a portion of its length, a pinion having ridges that mate with the ridges on the rack, the pinion being in connection with the actuation mechanism. The actuation mechanism can be provided such that actuation rotates the rack, which, in turn, moves the pinion proximally or distally relative to the device, which, in turn, pushes and pulls the push/pull rods, which, in turn, opens and closes the pair of arms, jaws, or elements movable with relation to each other. The device can further comprise a spring that pre-loads the actuation mechanism and causes the pinion to move. A pre-curved member can be embedded within the inner member along at least a portion of the length of the inner member, such that, as the inner member is extended outside the outer rigid member, the inner member takes the profile of the pre-curved member. The pre-curved member can be formed of a shape memory material, such as nitinol. The inner member can include one or more articulating knuckle members and, as the inner member is extended outside the outer rigid member, the inner member can bend at the one or more articulating knuckle members to take on a curved profile. A shape memory material, such as nitinol, pre-formed into a curved profile, can be embedded along at least a portion of the length of the inner member such that, as the inner member is extended outside the outer member, the inner member takes on the pre-formed curved profile of the shape memory material. At least a portion of the inner member can be formed of a shape memory material, such as nitinol, pre-formed into a desired curved profile such that, as the inner member is extended outside the outer rigid member, the inner member takes on the pre-formed curved profile. The device can further comprise a curvilinear actuation mechanism in connection with the inner member for controlling advancement of the inner member outside of the outer member. The device can include an actuating rod slidably disposed within the handle. The actuating rod can have a distal end in connection with the inner member and a proximal end extending outside the handle, such that movement of the actuating rod in a proximal direction pulls the inner member within the outer member, and movement of the actuating rod in a distal direction pushes the inner member outside of the outer member. The operable end can be rotatable about the longitudinal axis of the device. The inner member can be rotatable within outer member, thereby providing rotation of the operable end. The operable end can be rotatably mounted to the inner member. The device can provide visualization and access to the entire site via two portals, without interchanging access portals or providing access through additional portals. The device can have any combination of the following five degrees of freedom, which are described in more detail herein: "curvilinear bending" of a distal portion of the device, "rotation about the linear axis of the elongate body member", "rotation of the operable end", "operable end motion", and "rectilinear extension". The device can further comprise a curvilinear actuation assembly for movement of the inner member relative to the outer member. The operable end can be removable and interchangeable. The inner member can be removable and interchangeable. The operable end can comprise a camera and the device can further includes an LED illumination source in connection with one or more fiber optics extending through inner member and in connection with the camera. The operable end can further includes a lens system and the one or more fiber optics can comprise a fiber optic bundle, and the camera and lens system can be mounted at the distal end of the inner member and are surrounded by the fiber optic bundle. The LED illumination source can be mounted on a carrier slidably and rotatably disposed within housing and in connection with the inner member. The fiber optic bundle can be potted. The operable end can comprise an RF electrode electrically insulated from the inner member and/or the outer member and the handle. The RF electrode can comprise opposing electrodes for bi-polar and ablative applications or a single electrode for mono-polar applications at a single potential. The operable end can be in the form of a pair of jaws that, when disposed in a closed position, overlap each other to resect or punch tissue positioned between the pair of jaws. The operable end can be in the form of a powered blade with suction, and the device can further includes an actuation mechanism at its proximal end. The actuation mechanism can comprises a flexible drive shaft that can be in connection with an external motor powered unit Thus, tissue and other material can be pulled into the operable end using suction and the tissue and other material can be resected and withdrawn through the device using the blade, in combination with suction (e.g. by connecting the device to a vacuum source). The entire device or one or more portions of the device, such as the inner member, elongate member, and/or operable end, can be disposable. The entire device or one or more parts of the device can be reusable.

In another aspect, the invention generally relates to a medical device kit, comprising one or more of the components set forth herein. The one or more devices can be packaged in sterile condition.

In another aspect, the invention generally relates to a method for performing minimally invasive hip arthroscopic surgical procedures comprising (a) providing a device comprising a handle at a proximal end, an operable portion at a distal end, a body member extending between the handle and the operable end, the body member comprising an outer rigid member, and an inner member slidably housed within outer rigid member, the inner member having flexibility along at least a portion of its length, wherein as the inner member is retracted within outer rigid member, the inner member takes on the profile of the outer rigid member, and wherein as the inner member is extended outside the outer rigid member, the inner member takes on a curved profile, (b) disposing the inner member in a retracted position within the outer rigid member, (c) inserting the body member into the body and into the hip capsule, (d) extending the inner member outside the outer rigid member, (e) allowing the inner member to take on a curved profile, (f) performing the procedure, (g) withdrawing the inner member within the outer member, and (h) removing the body member from the body. The operable end can be further rotatable about the arcuate axis of the curved inner member.

In another aspect, the invention generally relates to a method of performing hip arthroscopy comprising providing a first portal in the posterolateral position and second portal in the anterolateral position; inserting a first device in the anterolateral position, the first device comprising a handle at a proximal end, an operable portion comprising a visualization device at a distal end, a body member extending between the handle and the operable end, the body member comprising an outer rigid member and an inner member slidably housed within outer rigid member, the inner member having flexibility along at least a portion of its length; inserting a second device in the posterolateral position, the second device comprising a handle at a proximal end, an operable portion comprising a operative device at a distal end, a body member extending between the handle and the operable end, the body member comprising an outer rigid member and an inner member slidably housed within outer rigid member, the inner member having flexibility along at least a portion of its length; and extending the inner member of the first device and second device outside of the outer member and allowing the inner member or the first and/or second device to take on an arcuate shaped path concentric with the radii of the femor head and acetabulum of the hip joint.

In another aspect, the invention generally relates to a method of performing minimally invasive diagnostic and surgical procedures on the hip comprising (a) providing a visualization and/or an operable device(s) comprising a handle at a proximal end; an operable end at a distal end; a rigid or semi rigid elongate body member extending between the handle and the operable end; a distal flexible end segment that rotatably connects the operable end to the elongate body member; the handle comprising control means to precisely maneuver the operable end by iteratively adjusting each of the following degrees of freedom: linear translation of the operable end into the hip joint capsule; rotation about the linear axis of the elongated body member; curvilinear bending of the distal flexible end segment; and rotation about an axis of a bend in the distal end segment; (b) disposing the flexible end segment into a straight configuration; (c) inserting the distal end of the device into the body and into the hip capsule; (d) linearly translating the operable end into the capsule; (e) iteratively adjusting the curvilinear bend radius of the distal flexible end segment while translating the operable end toward the operative target; (f) performing the procedure; (g) disposing the end segment into a straight configuration; and (h) removing the device from the capsule.

In another aspect, the invention generally relates to a method of performing arthroscopic procedures comprising providing a first portal in the posterolateral position and second portal in the anterolateral position; inserting a first device in the anterolateral position, the first device comprising a handle at a proximal end, an operable end comprising a visualization device at a distal end, a body member extending between the handle and the operable end, and an end segment connecting the operable end to the body member and capable of being iterively manipulated to translate, bend, and rotate to achieve a desired position at the target site and to achieve a desired field of view; and inserting a second device in the posterolateral position, the second device comprising a handle at a proximal end, an operable end comprising an electrical manipulation device or a mechanical manipulation device at a distal end, a body member extending between the handle and the operable end, and an end segment connecting the operable end to the body member and capable of being iteratively manipulated to translate, bend, and rotate to achieve a desire position at the target site and to actuate to achieve the desired surgical outcome.

A particular aspect of the invention provides a device for diagnostic or surgical procedures. The device comprises a tubular outer body member having a proximal end and a distal end and having a handle attached to the proximal end of the outer body member. A flexible distal end segment extends from the distal end of the outer body member. This flexible distal end segment has an axial end segment passage formed through it. The device further comprises a rotation control member comprising an extension tube portion rotatably disposed within the outer body member and a flexible drive shaft portion. The flexible drive shaft portion is attached to and extends distally from a distal end of the extension tube portion for rotation therewith. At least a portion of the flexible drive shaft portion is rotatably and slidably disposed within the axial end segment passage so as to take on a profile of the flexible distal end segment. The device also comprises an operable end attached at a distal end of the flexible drive shaft portion for rotation therewith. The flexible drive shaft is selectively rotatable to establish a desired rotational orientation of the operable end. The flexible distal end segment may comprise an exterior flexible member attached to the distal end of the outer body member and an interior flexible member. The exterior flexible member may have an exterior member axial passage formed therethrough. The interior flexible member has proximal and distal ends and defines the axial end segment passage. At least a portion of the interior flexible member is disposed within the exterior flexible member so as to take on a profile of the exterior flexible member.

Methods in accordance with these aspects can further include the following features. The method can include rotating the inner member of the first and/or second device about the longitudinal axis of the outer member, and/or rotating the operable end about the arcuate axis of the curved elongate body member/inner body member. The operable end includes a pair of arms, jaws, or one or more movable elements, and the handle further comprises control means to actuate the movement of the one or more movable elements, and the method further comprises performing the procedure by actuating the operable end to manipulate tissue and other target sites within the hip joint capsule.

A particular aspect of the invention provides a method of performing a surgical procedure within a confined body cavity of a patient using a surgical device. The surgical device has a tubular outer body member with a handle at its proximal end and a flexible distal end segment extending from its distal end. The surgical device also has an operable end extending from the distal end of the flexible distal end segment. The surgical device is configured for selectively causing the flexible end segment to bend to adopt a desired curvature and for selectively rotating the operable end relative to the flexible distal end segment about an axis of the flexible distal end segment. The method comprises placing the flexible end segment into a straight configuration and inserting the operable end and at least a portion of the flexible end segment into the body cavity. The method further comprises linearly translating the operable end to a desired location within the body cavity. The method still further comprises adjusting the curvature of the flexible end segment to establish an engagement angle of the operable end relative to the outer body of the device and rotating the operable end about an axis of the flexible end segment to establish a desired operable end rotational angle.

The method also comprises operating the operable end to perform a surgical function with respect to a target tissue within the body cavity.

Other aspects and advantages of the invention will become apparent from the following description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings, in which:

FIG. 17A shows side view of a device in accordance with another embodiment of the present invention, wherein a flexible distal end segment is provided, and wherein the.

FIGS. 32A and 32B show side cross-sectional views of a portion of a surgical device according to an embodiment of the invention.

FIGS. 33A and 33B show side cross-sectional views of a portion of a surgical device according to an embodiment of the invention.

DETAILED DESCRIPTION OF THE INVENTION

Figure 1:
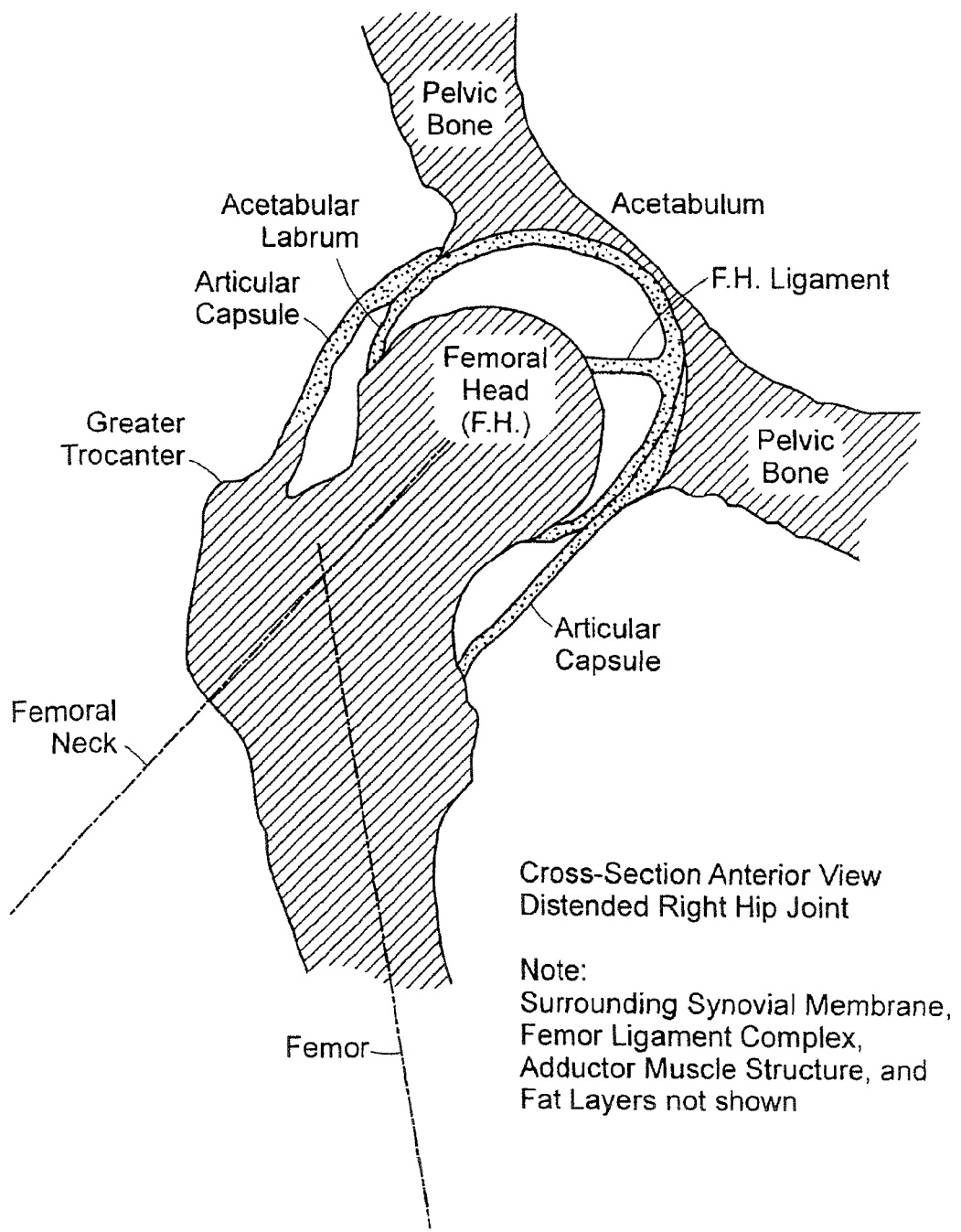
FIG. 1 shows a cross sectional anterior view of a distended right hip joint.
Figure 2A:
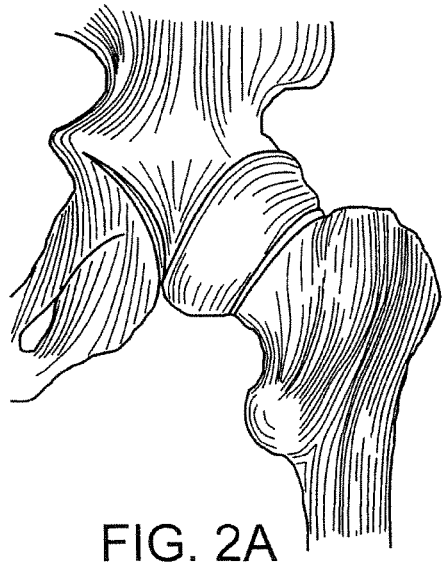
FIG. 2A shows a posterior view of the right hip joint.
Figure 2B:
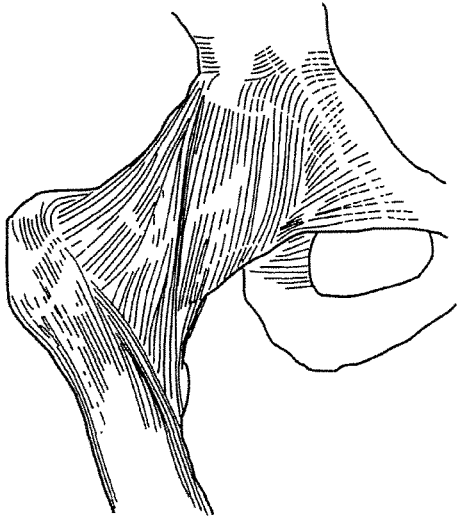
FIG. 2B shows an anterior view of a right hip joint with various ligaments shown.
Figure 2C:
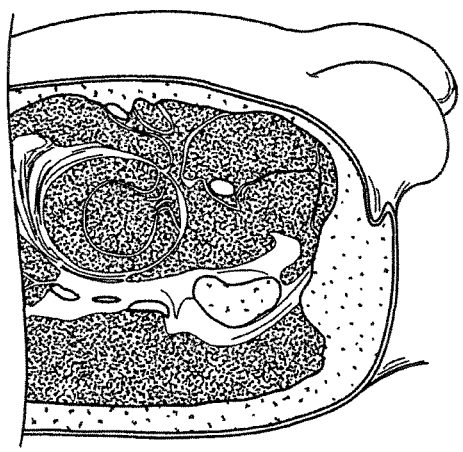
FIG. 2C shows the structures surrounding the right hip joint.
Figure 2D:
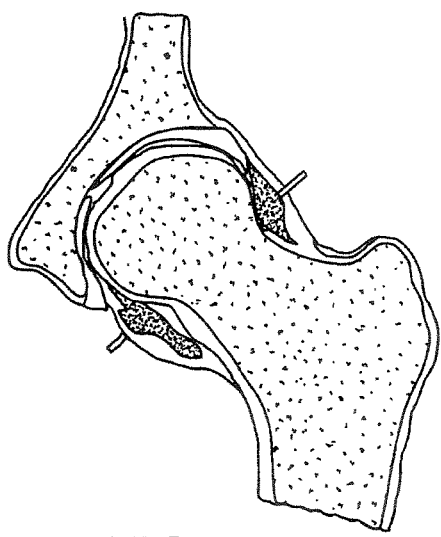
FIG. 2D shows a cross-sectional posterior view of the right hip joint.
Figure 3:
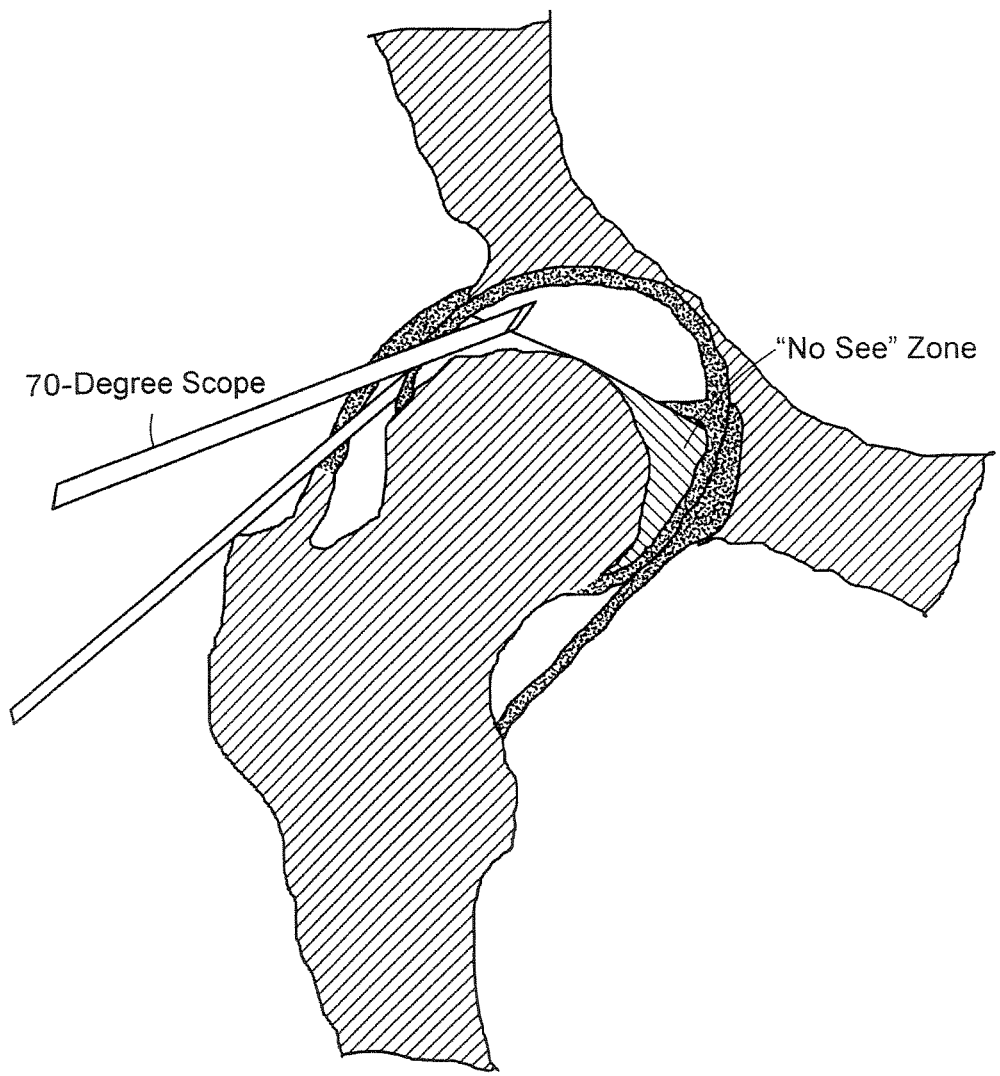
FIG. 3 shows access to the hip joint using 70.degree. arthroscopes and rigid operative tools.
Figure 4:
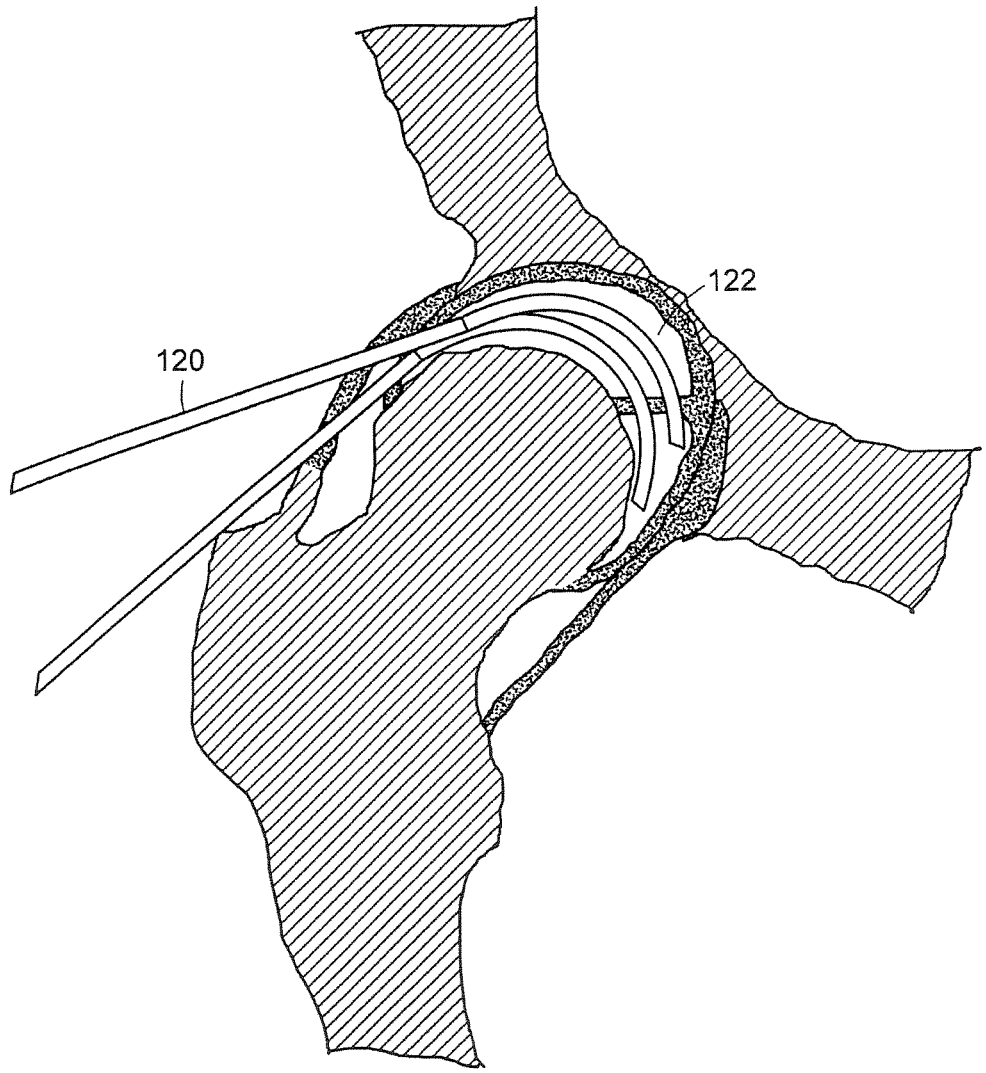
FIG. 4 shows access to the hip joint using an embodiment of the present invention.

The devices and methods of the invention are primarily illustrated and described herein by means of devices which have been adapted for use in performing arthroscopic procedures on the hip. The devices and methods provide access to the internal portions of the distended hip capsule during arthroscopic procedures that are presently not accessible using currently available arthroscopic instruments. The devices and methods can suitably be used to perform arthroscopic procedures not only on the hip, but also on other parts of the body, such as the knee and shoulder. The devices are particularly suitable for performing procedures on parts of the body that require flexible access. The devices and methods are not limited to arthroscopy, and can further be used in endoscopic and laparoscopic procedures as well as open surgeries. The devices can be in the general form of any conventional diagnostic or operative instrument including, but not limited to, gaspers, scissors, forceps, scalpels, punches, probes, dissectors, mono polar cautery, bi-polar ablation/cautery, CCD camera and lens. Thus, the disclosure to follow should be construed as illustrative rather than in a limiting sense.

FIGS. 5-16 illustrate various embodiments and views of a medical device 100 according to the invention. The medical device 100 has a proximal end 102, a distal end 104 defining an operable end 105 of the device, and an elongate body member 106 extending therebetween. As used herein, "elongate" generally refers to a member or element that is long in proportion to width, "proximal" generally refers to a position or direction that corresponds to the user, and "distal" generally refers to a position or direction that corresponds to the patient.

The elongate body member 106 is shown having a generally cylindrical shape with a circular cross-section. However, this shall not be construed as limiting the body member 106 to such as shape, as it is within the scope of the present invention for other geometric shapes to be used for the elongate body member 106. In an exemplary embodiment, the body member 106 includes a smooth outer surface. The elongate body member 106 is also shown having a straight, rigid shape along a substantial portion of its length. However, this shall not be construed as limiting the body member 106 to such as shape, as it is within the scope of the present invention for other geometric shapes to be used for the elongate body member 106. For example, a flexible elongate body member 106 will have important utility in certain applications, especially as they relate to endoscopic requirements into any of the long, tortuous, cavities of the body commonly encountered especially in ENT and colorectal procedures.

The elongate body member 106 can be fabricated from any bio-compatible material known to those skilled in the art for use in fabricating medical instruments. The material can be lightweight and strong and can include, for example, surgical grade stainless steel, anodized aluminum, and polymeric materials and composites. The dimensions of the device 100 can vary depending on the type of procedure performed and can be readily determined by one of skill in the art. In general, the length and thickness of the device is in accordance with conventional medical devices.

The proximal end 102 can include a handle 103 that is grasped by a user, and can be adapted to assist the user in securely gripping and manipulating the device 100. For example, the handle 103 can include a rubber coating, grooves or similar finger grip configuration (e.g., surface preparations or artifacts), and the like.

The distal end 104 defines an operable end 105 of the device and can be in the form of conventional surgical and diagnostic medical device operable ends. For example, the operable end 105 can be in the form of gaspers, scissors, forceps, scalpels, punches, probes, dissectors, mono polar cautery, bi-polar ablation/cautery, CCD camera and lens. The general design of the operable end 105 can be in accordance with conventional operable ends.

In embodiments wherein the operable end 105 is in the form of a scalpel, probe, or similar static end that does not require actuation, the proximal end 102 can include a simple handle 103, much like that found on, for example, a conventional scalpel.

In embodiments wherein the operable end 105 is in the form of, for example, grasper or scissors, which include a pair of arms, jaws or other elements that are movable in relation to each other, the device includes an actuation mechanism (e.g. 112, 113) in connection with the operable end 105 and configured and arranged to move the arms, jaws or elements of the operable end 105. In one embodiment, the handle 103 is an actuating handle that, when manipulated, moves the arms, jaws or other elements. Such actuating handles are well known and, thus, the present handle 103 can be in accordance with conventional actuating handles. In one embodiment, the handle includes a trigger 112 (FIG. 5A) or a ring 113 (FIG. 5B) engaged by a finger or thumb of the user. Manipulation of the trigger 112 or ring 113, for example, pressing the trigger 112 or ring 113 towards the handle 103, causes the arms, jaws, or other elements to open or close. In another embodiment, the handle 103 can be similar to the handle of scissors or the like, with finger and thumb holes that can be opened and closed to open and close/relax the arms, jaws, or other elements. In other embodiments, one or more actuating buttons (not shown) are provided that opens and closes the arms, jaws, or other elements when pressed.

In embodiments wherein the operable end 105 has arms, jaws, or elements are controllable by an actuation mechanism, the body member 106 can be hollow and house apparatus that connects the actuation mechanism to the operable end 105. Manipulation of the actuation mechanism causes the apparatus to open and close the arms, jaws, or other elements. For example, the hollow body member 106 can house one or more cables or push/pull rods (not shown) in connection with a cam (not shown) to open and close arms, jaws or similar movable or grasping mechanisms.

The operable end 105 of the device, including, graspers, punches, scissors, RF ablative electrode/s, or CCD cameras with directional lenses, can be controllable in five degrees of freedom by actuating mechanisms. In some embodiments, fewer than five degrees of freedom can be provided as desired.

Figure 17A:
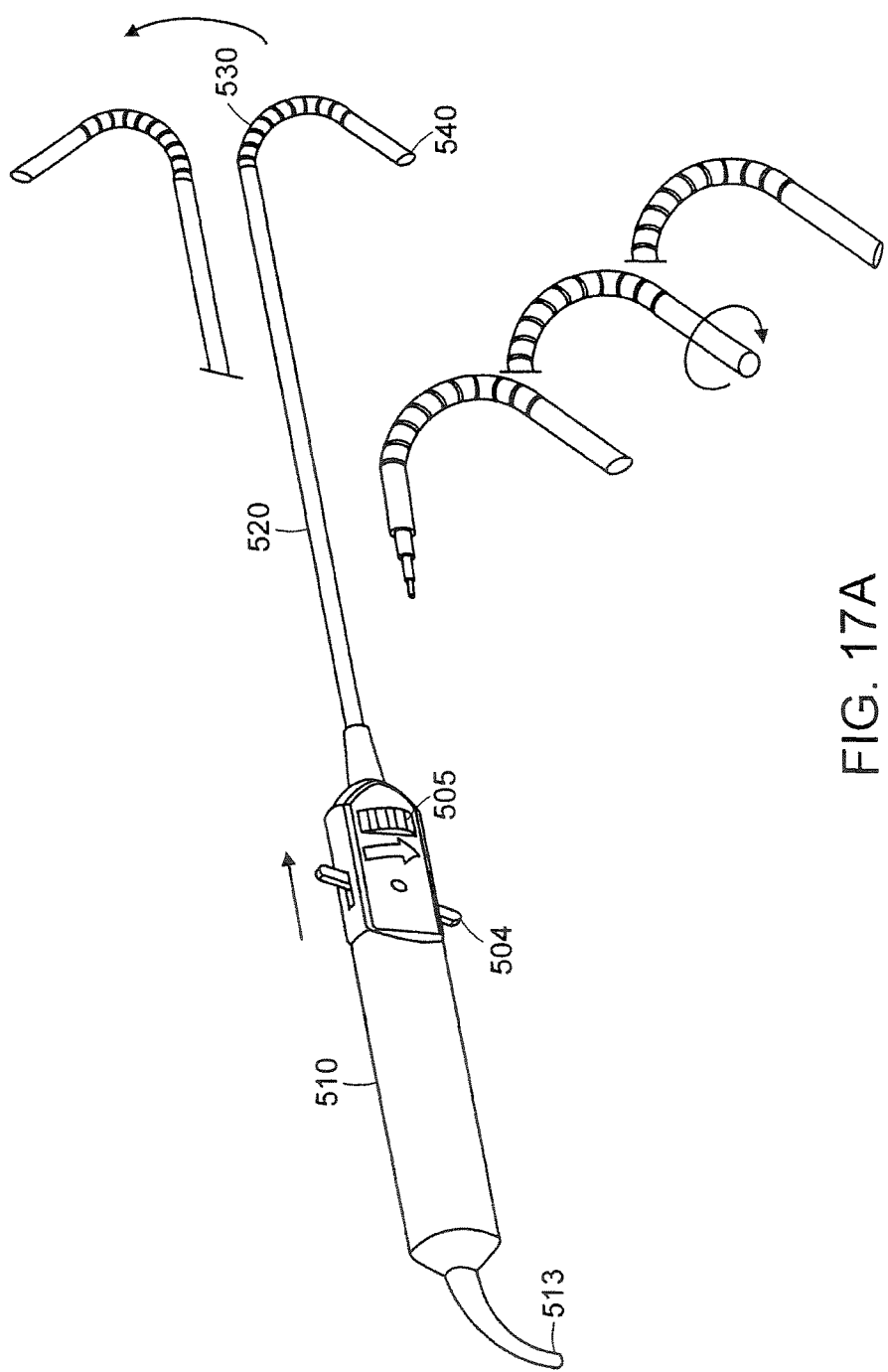
Figure 17B:
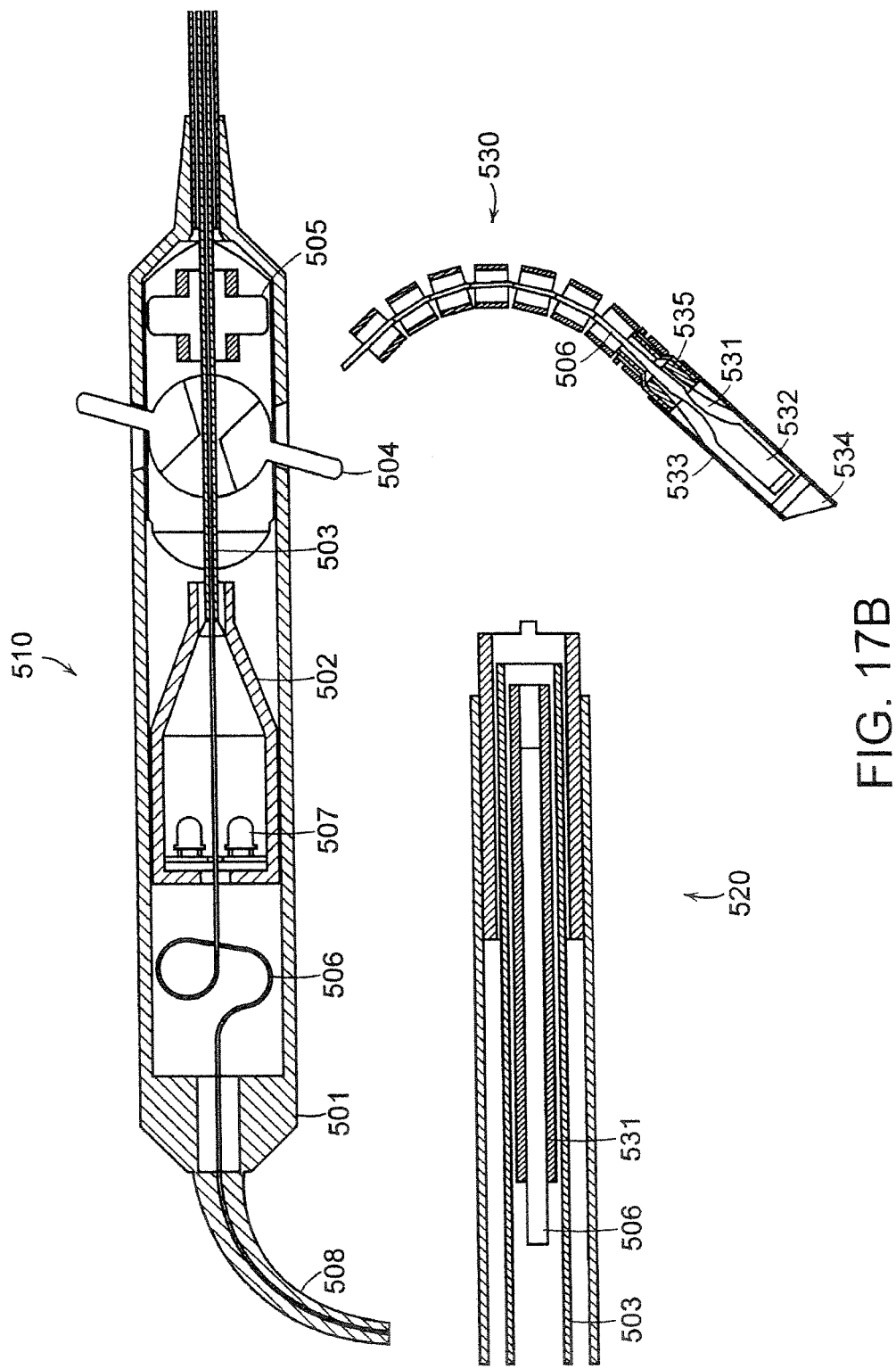
FIG. 17B shows a detailed cross-sectional view of the handle, the flexible distal end segment, and the elongate body member of the device shown in FIG. 17A.
Figure 26:
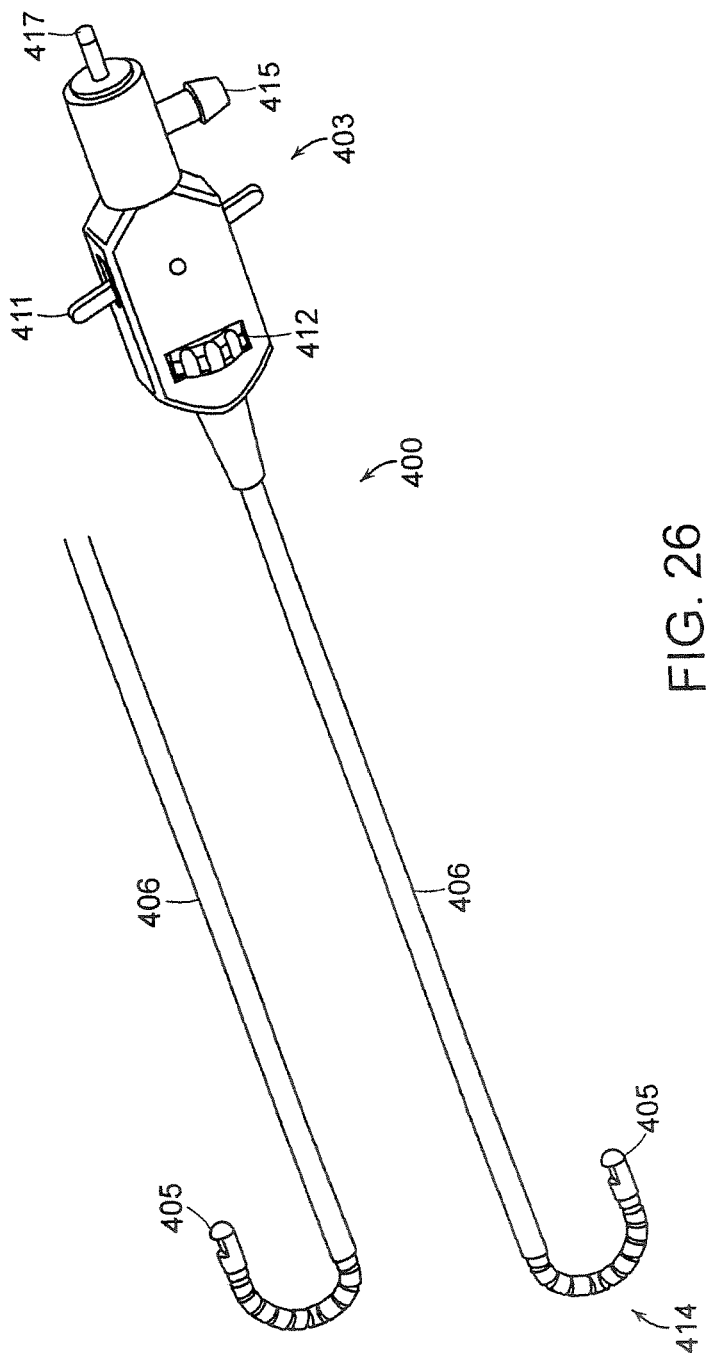
FIG. 26 shows a side view of a device in accordance with another embodiment of the present invention having a flexible distal end segment formed of vertebrae.

One degree of freedom is called "curvilinear bending" of a distal portion of the device. With this degree of freedom, the elongate body member 106 provides curvilinear bending motion about its longitudinal axis, which allows for the smooth bending into a desired arcuate shape. In one embodiment, at least a portion of the elongate body member 106 is flexible (e.g. distal flexible portion 214 in FIGS. 18A and 20; distal flexible portion 314 in FIGS. 22 and 24; distal flexible portion 414 in FIG. 26; and distal flexible portion 515 in FIG. 17A) and so as to provide the curvilinear bending motion. In one embodiment, the curvilinear bending motion is controllable at the proximal end 102 of the device. For example, the device can include a handle 103 or distal end 102 having a curvilinear bending actuation mechanism (not shown) that causes the body member 106 to curve and/or controls the amount of curve of the body member. The degree of bending is independent of the other degrees of freedom (e.g. rotation) and the actuation of operable end 105.

Figure 5A:
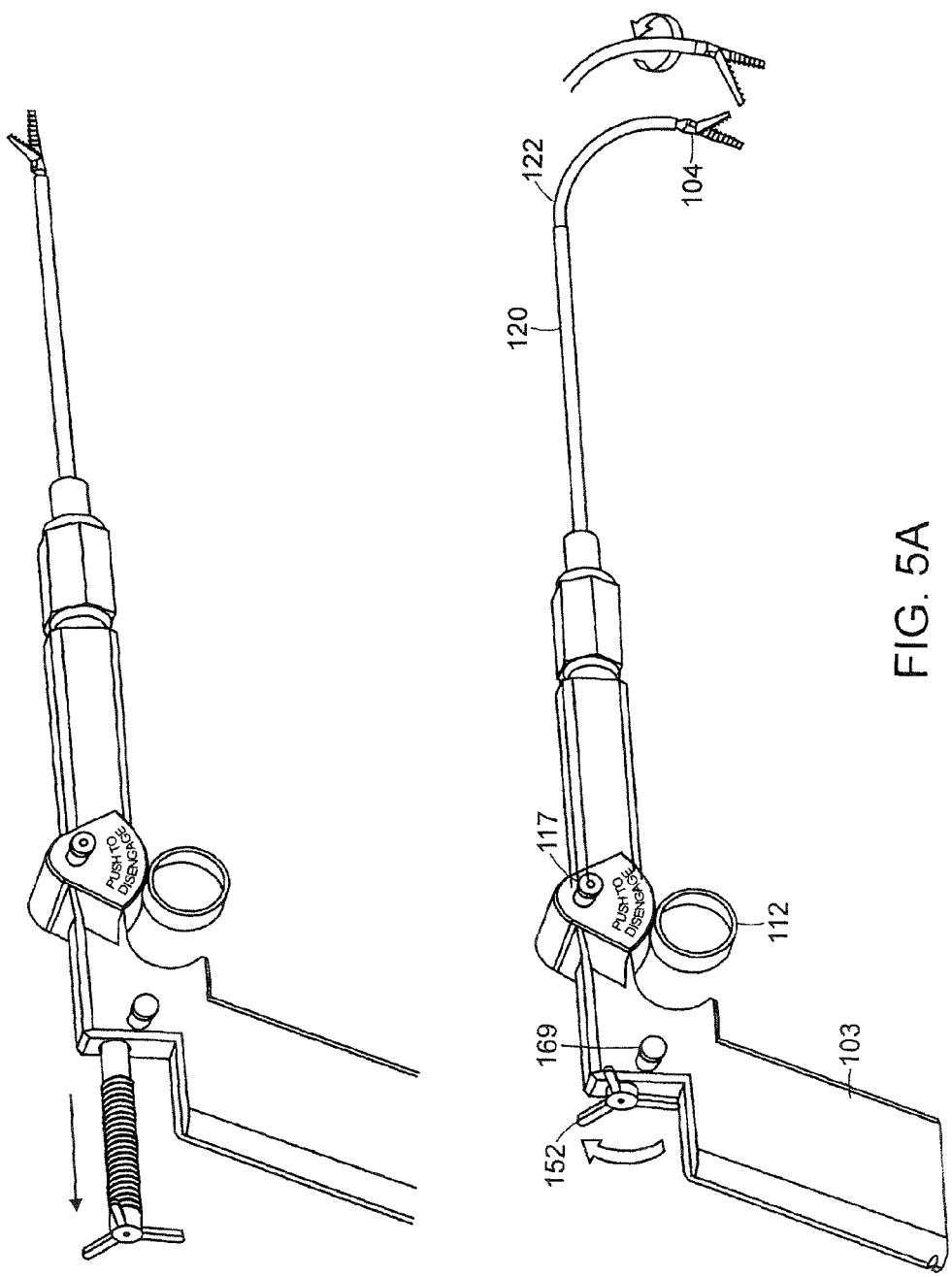
FIG. 5A shows a side view of a device in accordance with one embodiment of the present invention, wherein the distal end is in an extended curvilinear position, and a finger actuated trigger is provided.

In one embodiment, for example, as shown in FIGS. 6A-8D, curvilinear bending motion can be provided by forming the elongate body member 106 of at least two concentric body members including a relatively rigid outer body member 120 and an inner body member 122 having flexibility along at least a portion of its length. The inner and outer body members 122, 120 are shown as being generally tubular in shape. However, the shape of the inner and outer body members 122, 120 can be provided in other geometrical shapes, with the inner body member being slidably received within the outer body member. In one embodiment, shown, for example, in FIGS. 5A and 5B, the outer body member 120 is fixed to and extends from the handle 103, while the inner tubular member 122 is slidably disposed within the outer body member 120. The inner tubular member 122 distal end forms the distal end 104 of the elongate body member. The inner tubular member can further be received within at least a portion of the handle 103 as shown in FIG. 5A. When the inner body member 122 is housed within the outer body member, it takes on the shape of the outer body member. As the inner body member 122 is advanced outside of the outer body member 120, the inner body member is allowed to take on a curved profile due to its flexibility. The curvilinear bending motion can be about a radius as shown in the figures.

In some embodiments, the inner body member 122 can be pre-bent into a fixed radius form so as to control the bend radius of the inner body member 122 as it extends outside of the outer body member 120. In this aspect, the degree of bend can further be controlled by the amount by which the inner body member 122 is extended outside of the outer body member 120. Thus, for example, the degree of bending of the inner body member 122 can be iteratively adjusted with changes in the linear extension of the inner body member 122 outside of the outer body member 120 by the user, e.g. as the operative end 105 is translated into the joint capsule.

Figure 6A:
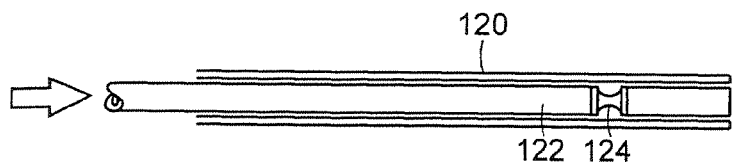
FIGS. 6A-D show one embodiment wherein the "curvilinear bending motion" degree of freedom is provided.
Figure 6B:
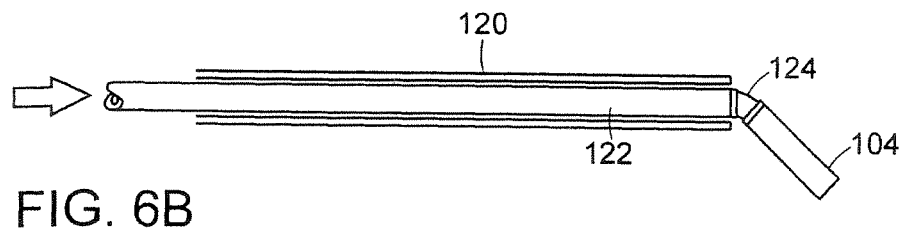
Figure 6C:
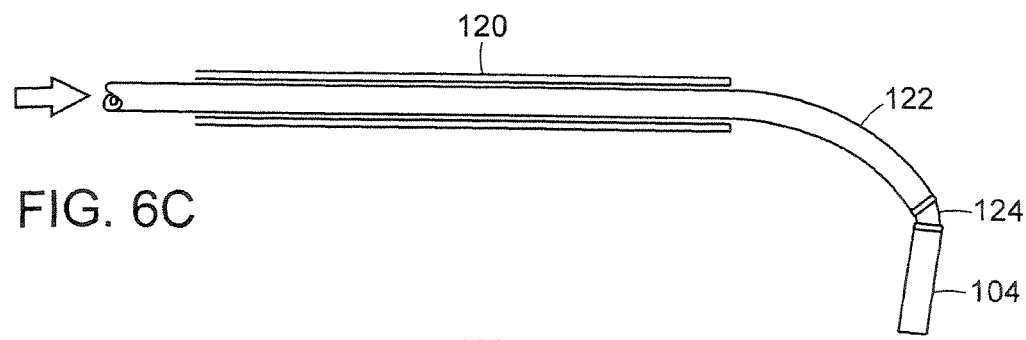
Figure 6D:
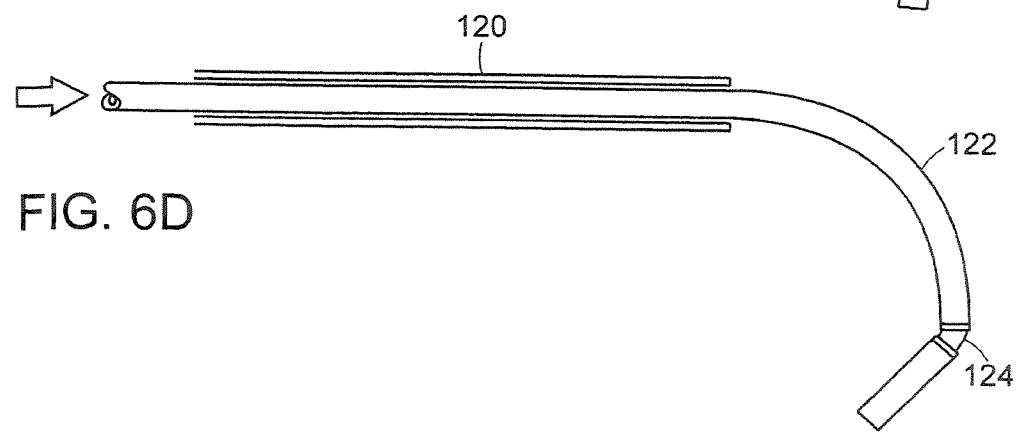
Figure 7A:
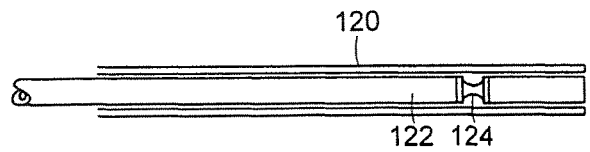
FIGS. 7A-D show the "rotation of the operable end" degree of freedom of one embodiment of the invention.
Figure 7B:
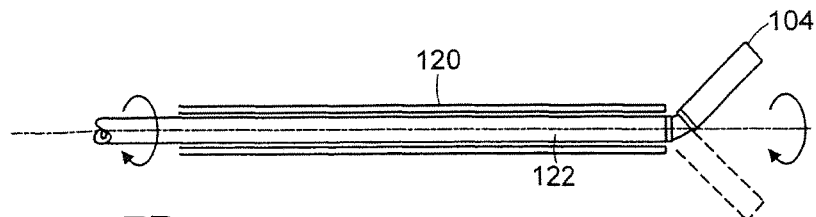
Figure 7C:
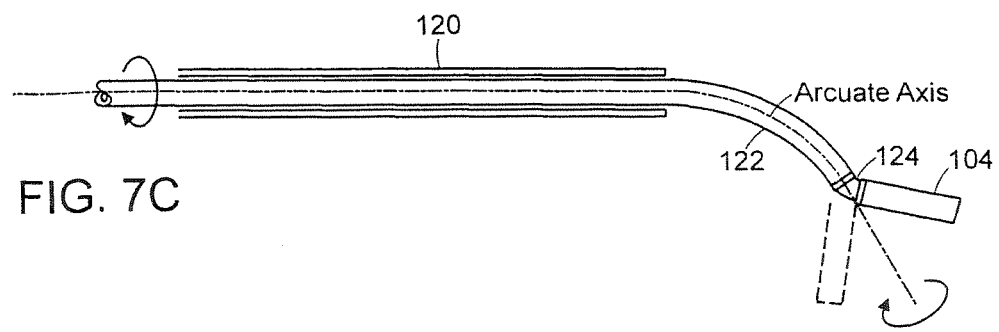
Figure 7D:
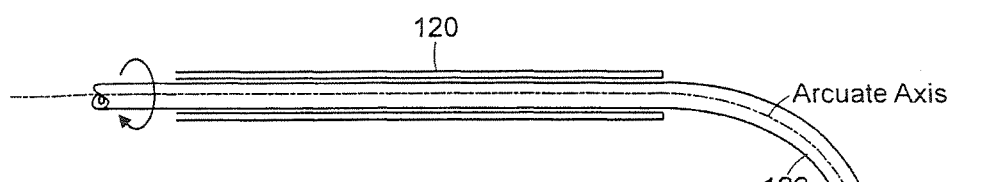
Figure 8A:
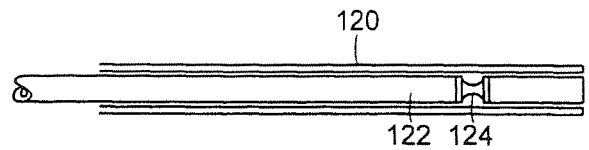
FIGS. 8A-D show the "rotation about the linear axis of the elongate body member" degree of freedom of one embodiment of the invention.
Figure 8B:
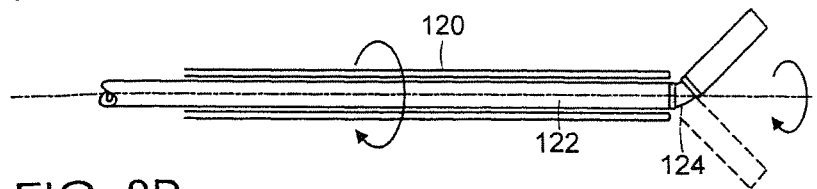
Figure 8C:
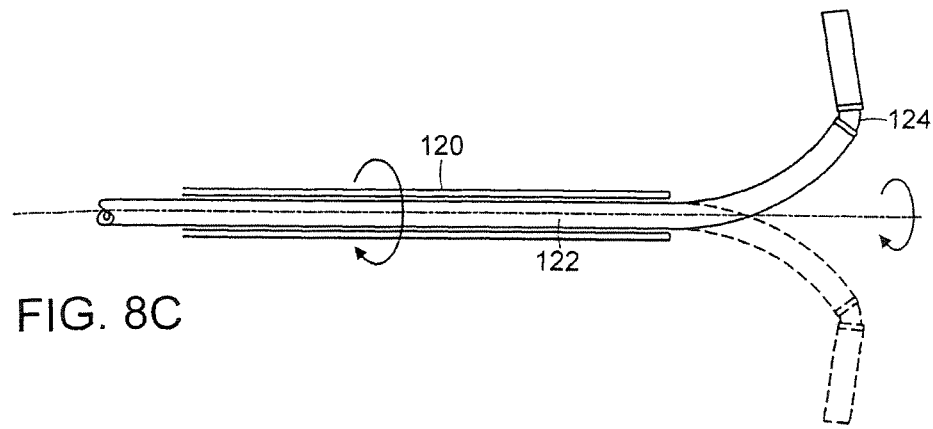
Figure 8D:
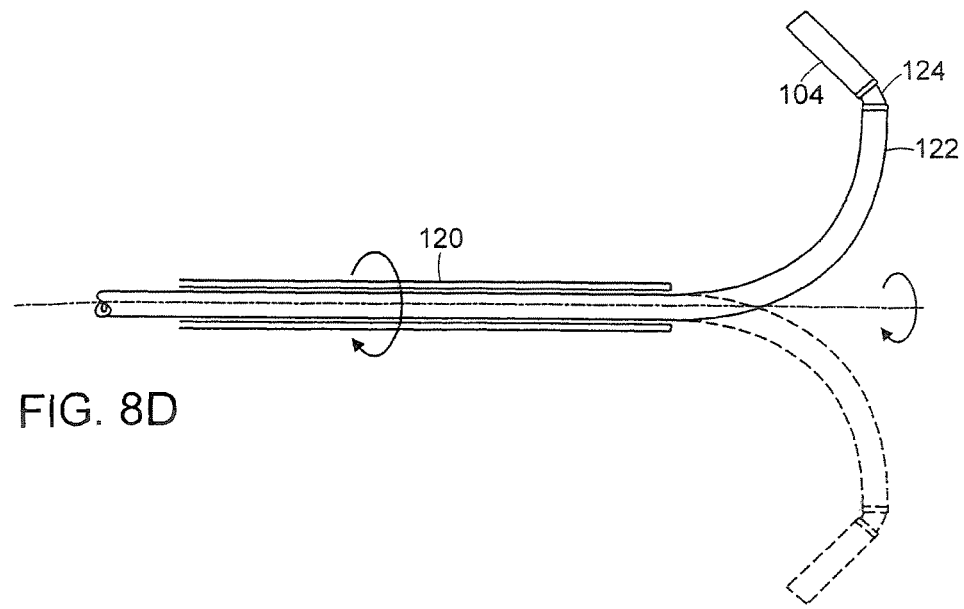
Figure 20:
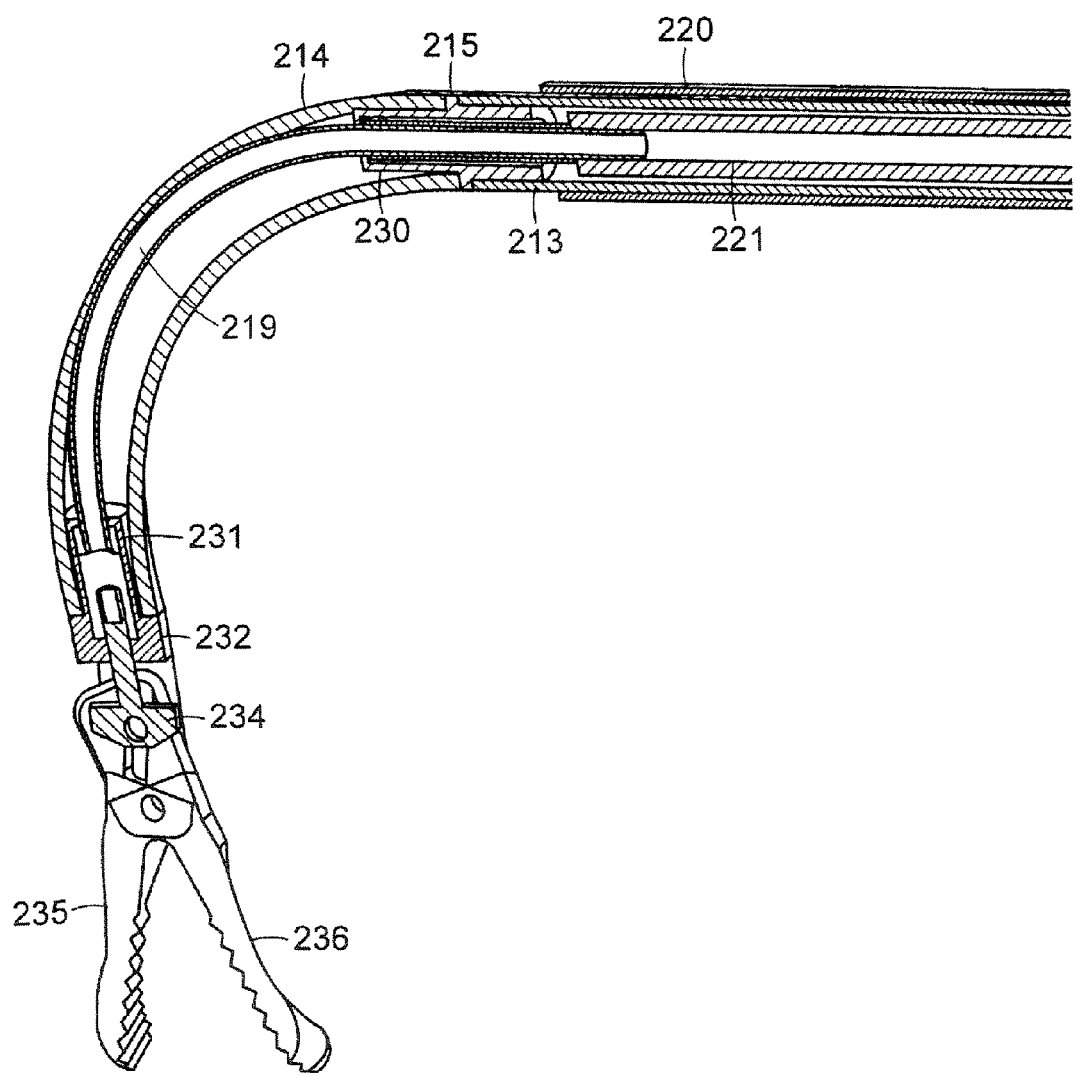
FIG. 20 shows a side cross-sectional detailed view of a distal portion of the device of FIG. 18A.

In some embodiments, a pre-bent member, such as a pre-bent member or wire (not shown), or similar form shown as pre-formed tube 219 in FIG. 20, is positioned along or embedded within the inner body member 122 along at least a portion of its length. When the inner body member 122 is housed within the outer body member 120 as shown in FIG. 6A, the inner body member 122 and the pre-bent member take on the shape of the outer body member 120. As the inner body member 122 is extended outside the outer body member 120, the inner body member 122 takes on the curvilinear shape of the pre-bent member or wire.

In another embodiment, the distal end 104 is in connection with the inner tubular member 122 via one or more articulating knuckle members 124, configured as shown in FIGS. 6A-D. When the inner body member 122 is within the outer body member 120, the inner body member 122 takes on the configuration of the outer body member 120 (straight) as shown in FIG. 6A. As the inner body member 122 is extended outside of the outer body member, it is allowed to bend at the one or more articulating knuckle member 124 to take on a curved profile.

In other embodiments, a shape memory material is embedded in or positioned along at least a portion of the inner body member 122. The shape memory material is formed into a desired curved profile and embedded within inner body member 122, which is flexible along at least a portion of its length. When unconstrained, the shape memory, and, thus, the inner body member 122, take on the pre-formed curved shape. Thus, when the inner body member 122 is retracted within the outer body member 120, it takes on the shape of the outer body member 120. As the inner body member 122 is extended outside the outer body member 120, the inner body member 122 takes on the shape of the shape memory material. In other embodiments, rather than embed a shape memory material within the inner body member 122, at least a portion of the inner body member 122 is formed of a shape memory material and pre-formed into a desired curved profile.

Figure 23:
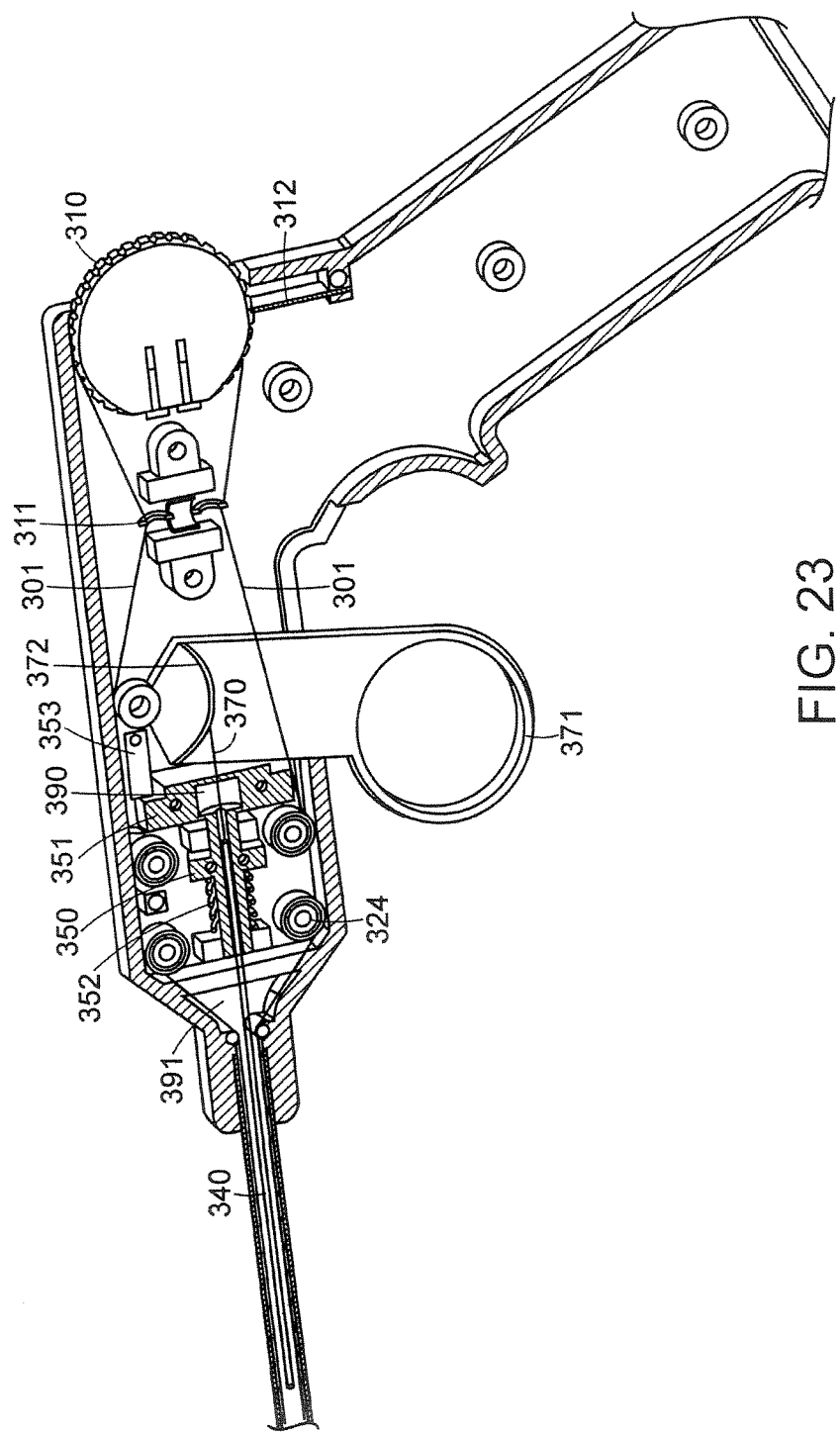
FIG. 23 shows a side cross-sectional detailed view of one embodiment of the handle of FIG. 22.
Figure 24:
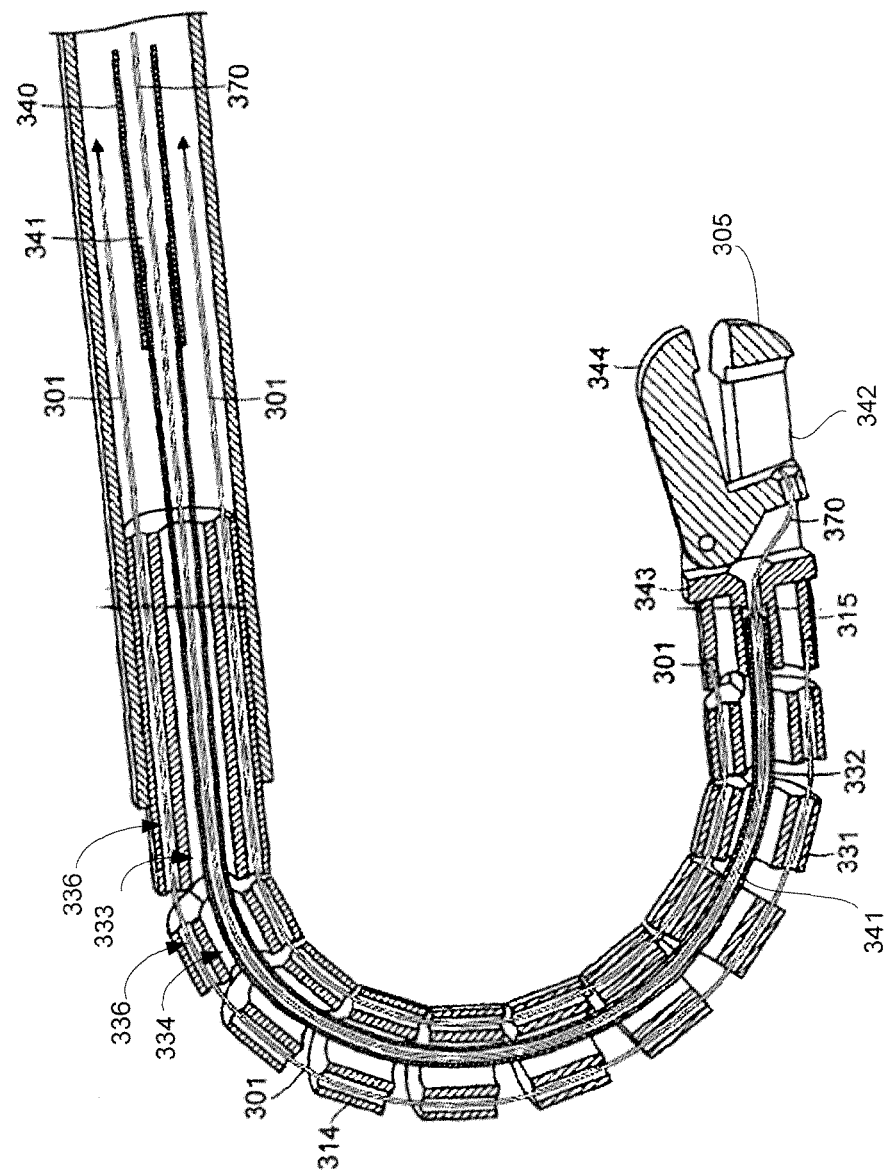
FIG. 24 shows a cross-sectional detailed view of a distal portion of the device of FIG. 22.
Figure 29:
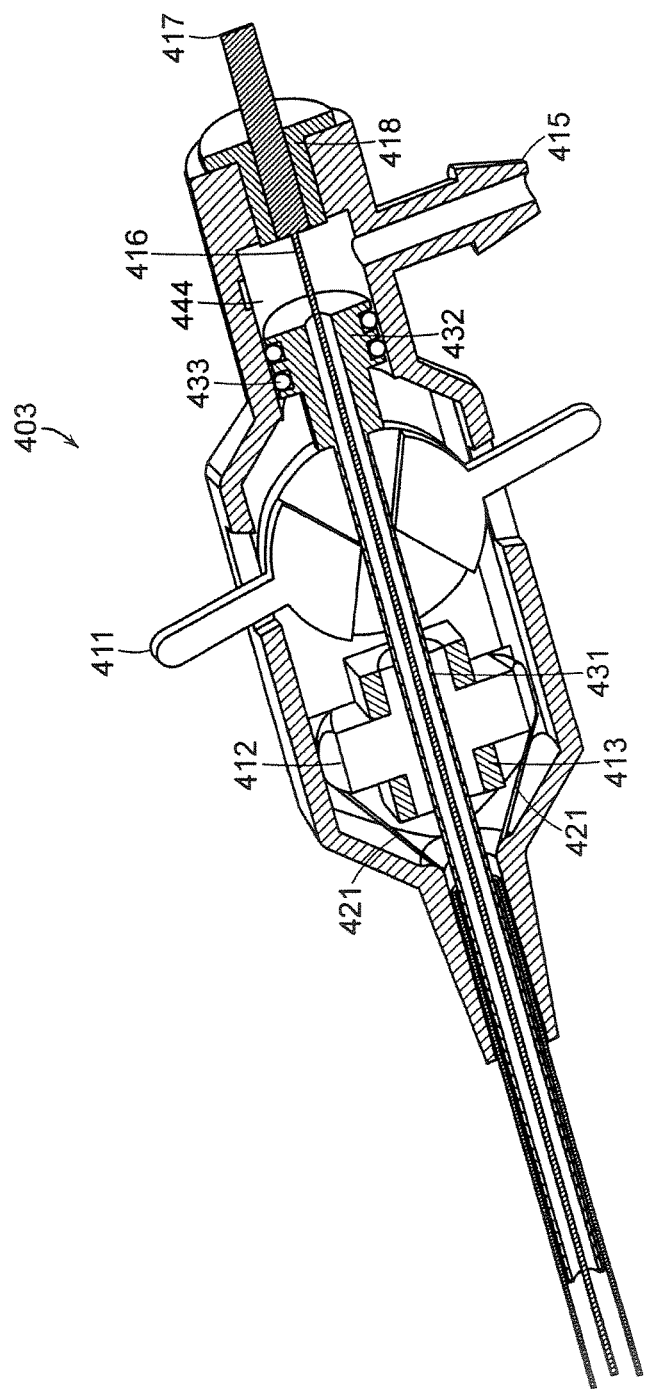
FIG. 29 shows a side cross-sectional detailed view of one embodiment of the handle of FIG. 26.

In another embodiment, the inner body member 122 is flexible along at least a portion of its length and its bending is controlled or articulated with a system of embedded steering cables (such as the steering cables 301 shown in FIGS. 23 and 24, and the steering cables 421 shown in FIG. 29). The degree of bend in the inner body member 122 is controlled, for example, by tensioning one of an opposing pair of cables (not shown), that causes the inner member 122 to bend proportionally to the pull force on the cables. For example, as shown in FIGS. 23 and 29, a rotational device or cam 310/411 is in connection with the pair of cables such that manipulation of the rotational device 310/411 results in tension on the cables and bending of the inner body member 122. The degree of bending can be iteratively adjusted by the user as the operable end 105 is translated into the joint capsule.

Figure 13:
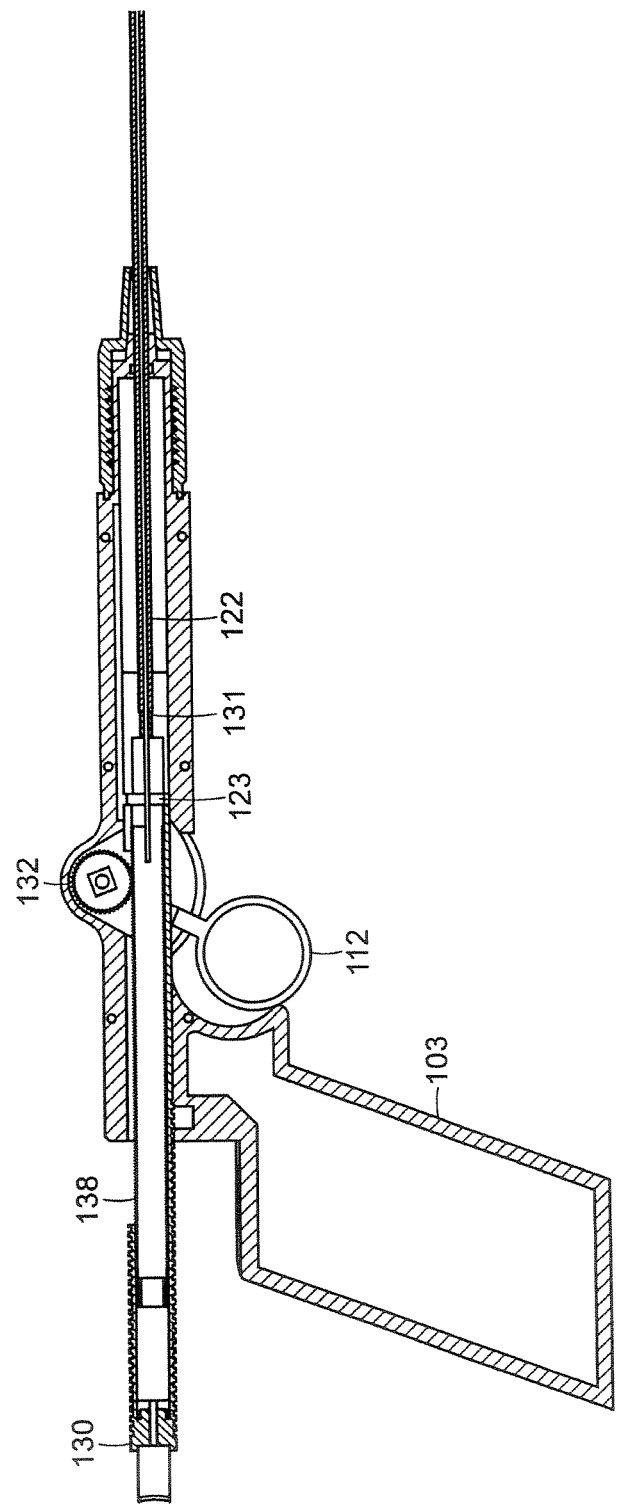
FIG. 13 shows a cross-sectional view of one embodiment of the handle, wherein the handle is actuated to provide the distal end in an extended position.
Figure 14:
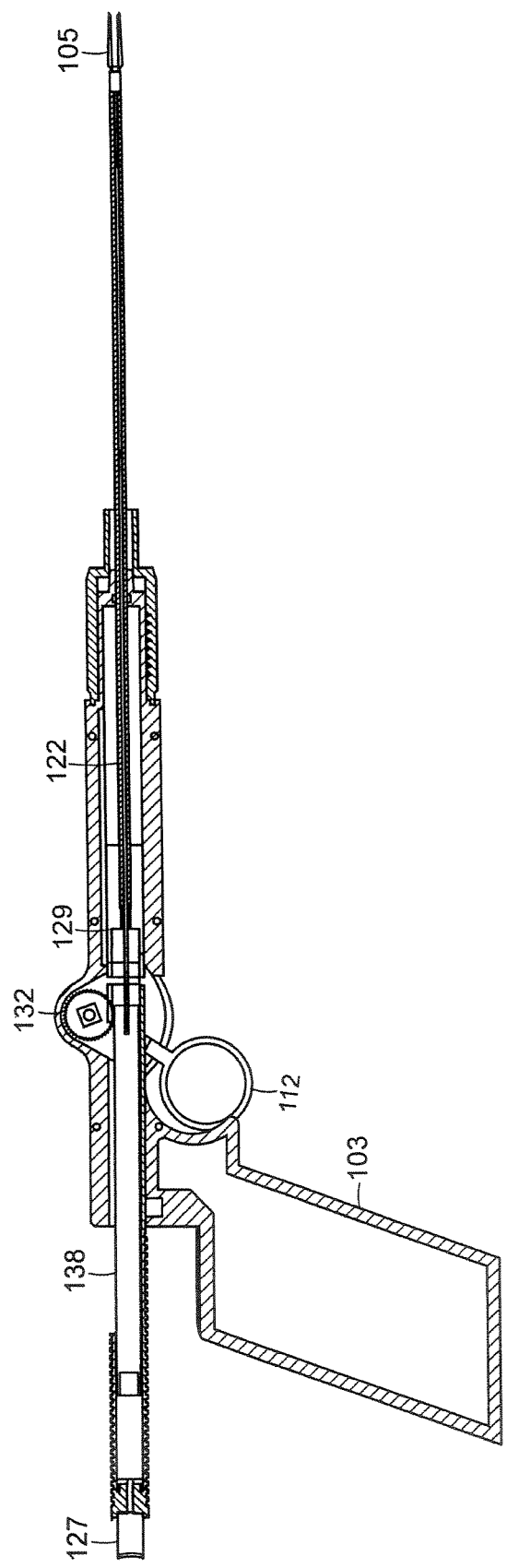
FIG. 14 shows a cross-sectional view of one embodiment of the device, wherein the trigger is actuated to provide the distal end in a retracted position.
Figure 15:
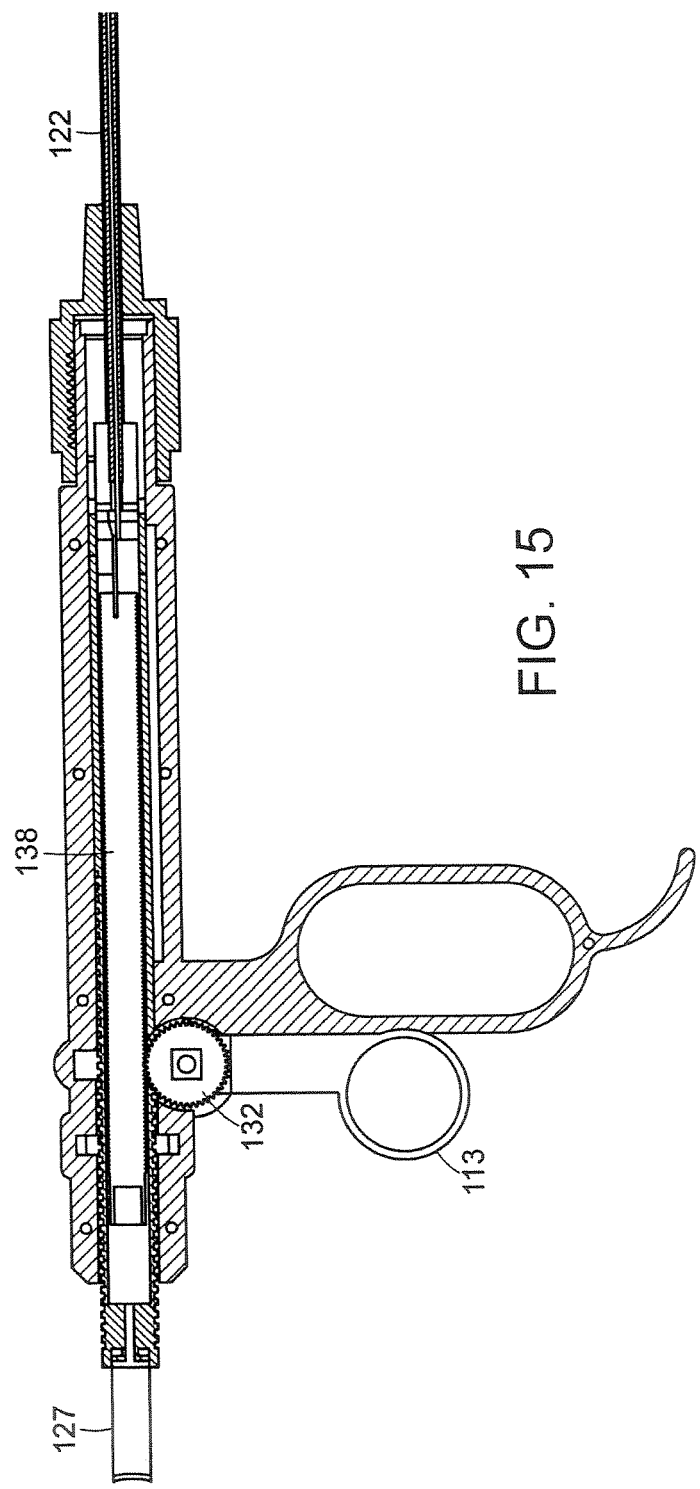
FIG. 15 shows a cross-section view of one alternate embodiment of the handle which uses a thumb-actuated trigger/ring.

Advancement of the inner body member 122 outside of the outer body member can be controlled by a curvilinear actuation mechanism in connection with the inner body member 122. In one embodiment, for example, as shown in FIGS. 13 and 14, the inner body member 122 extends from the distal end 104 to the handle 103. The inner body member 122 can be received within at least a portion of the handle, and is in connection with a slidable housing 130. In one embodiment, slidable housing 130 has a proximal end 127 and a distal end 129. Proximal end 127 is positioned outside of the handle 103 as shown in FIGS. 13 and 14, while distal end 129 is fixed to the inner body member 122. The slidable housing 130 is slidably received within the handle between an extended position, shown in the bottom view of FIG. 5A, and a retracted position, shown in the top view of FIG. 5A. When the slidable housing 130 is extended, it pushes the inner body member 122 in a distal direction and out of the outer body member 120. When the slidable housing 130 is retracted, it pulls the inner body member in a proximal direction and inside of the outer body member 120. The distal end of the slidable housing 130 can be directly in connection with the inner body member 122 or indirectly connected to the inner body member 122, for example, via a connection mechanism 131 as shown in FIGS. 13 and 14. In some embodiments, a ring or similar mechanism can be positioned at the proximal end 127 of slidable housing 130 to facilitate movement of the slidable housing 130 relative to handle 103.

In another embodiment, the slidable housing 130 can be in connection with one or more actuating triggers or buttons (not shown) at the distal end of the handle such that pushing the button(s) or trigger(s) causes the inner body member 122 to extend or withdraw relative to the outer body member 120 (e.g. via an actuating rod 123).

The device can be designed to bend at a radius that provides enhanced access to the site of the procedure. For embodiments wherein the device is adapted for use in hip procedures, the bend radius can correspond to the curvature of the femoral head. For example, the device can bend at approximately a 25 mm radius, which corresponds to the curvature of the femoral head. When the device designed for use in capsules smaller than the hip, such as the knee and the shoulder, the bend radius can be smaller to accommodate the size of the capsule. In one embodiment, the device is designed for use on the knee and shoulder, and the device bends at approximately a 12 mm radius. When the device is designed for use in capsules smaller than the knee and shoulder, such as the elbow, wrist, and intraverterbral spaces, the bend radius can be smaller in size to accommodate the capsule. For example, the bend radius for the elbow, wrist, and intraverterbral spaces can be as small as few mm. Outside the field of arthroscopy, for example, general abdominal laparoscopy for laparoscopic colosysectomy or appendectomy, the curvature would be larger, for example, the bend radius can be as large as a 50 mm.

Another degree of freedom, called "rotation about the linear axis of the elongate body member", provides rotation of the elongate body member 106, for example, as shown in FIGS. 8A-D. This rotation also moves the operable end 105 in a broad circular path as shown. This degree of freedom can simply be provided by rotation of the entire device 100, for example, by holding and rotating the handle.

Another degree of freedom is shown in FIGS. 7A-D, and is called "rotation of the operable end". This degree of freedom allows for the smooth rotation of the operable end 105 about the arcuate axis of the curved inner member 122. For example, an inner body member 122 can be rotatably and slidably disposed within outer body member 120. In one embodiment, the inner body member 122 is in connection with the slidable housing 130 that also rotates. The proximal end 127 of the slidable/rotatable housing 130 extends outside of the handle 103, as discussed above, and can be rotated relative to handle 103. As the slidable/rotatable housing 130 is rotated, the inner body member 122 also rotates. The inner member 122 can, thus, rotate about its arcuate axis irrespective of the extent or radius of the bend or degree of jaw actuation. This rotation can also be transferred to the distal end 104 rotatably mounted to the device.

Another degree of freedom is called "operable end motion". In those embodiments where the operable end 105 consists of a pair of intermating elements, e.g. graspers, punches, scissors, or the like, an actuating mechanism causes the movable elements to open and close one relative to the other. This allows the surgeon to grasp, resect or otherwise mechanically manipulate the target surgical tissue. The actuation is independent of the degree of extension, bending, or rotation. This motion can be controlled by the position of the actuation mechanism (e.g. trigger 112, ring 113) on the handle 103, which works in connection with apparatus (e.g. cable(s) or push/pull rods) to open or close arms, jaws, or other elements. For electronic applications, wherein the distal end 104 is in the form of a cautery tool or a camera or the like, the actuation mechanism (e.g. trigger 112, ring 113) can switch power to the cautery electrodes or electronically control one variable on the camera.

Figure 9:
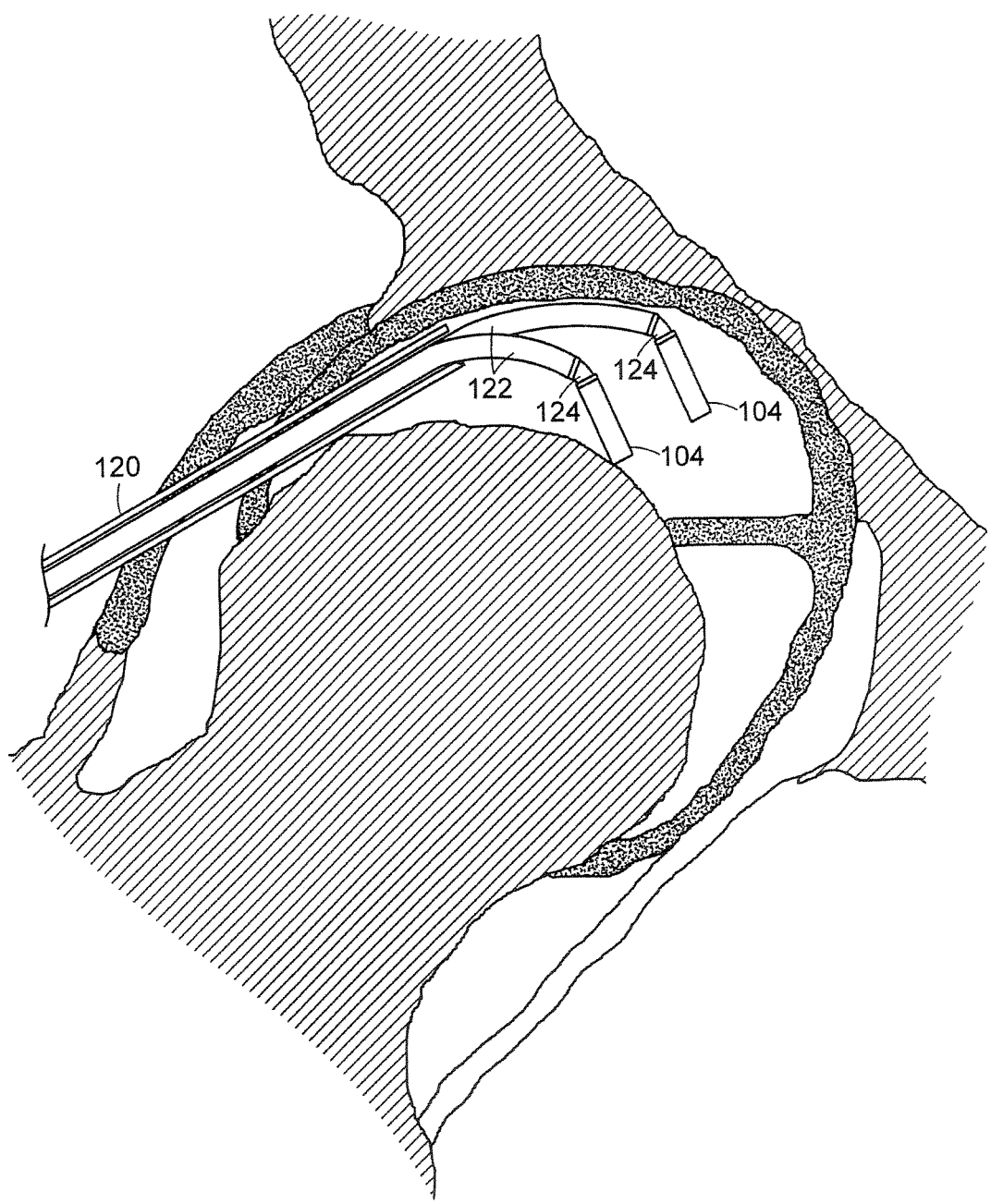
FIG. 9 shows "rectilinear extension" of the distal end degree of freedom of one embodiment of the invention with the device inserted in the hip joint capsule.

Another degree of freedom is called "rectilinear extension" of the distal end 104, and is illustrated schematically in FIG. 9. This degree of freedom allows the user to precisely control the degree of linear insertion of the operable end 105 into the hip joint capsule. This insertion impacts the depth of insertion and the depth of the distal end 104. Rectilinear extension can be irrespective of the bend radius, arcuate rotation, or jaw actuation.

The combination of the plurality of degrees of freedom allows visualization and access to the entire hip joint. Such visualization and access can be provided without interchanging access portals. The degrees of freedom can be controlled by one or more of the actuating mechanisms described herein. In some embodiments, these degrees of freedom can be operable by a single hand holding the device.

Figure 5B:
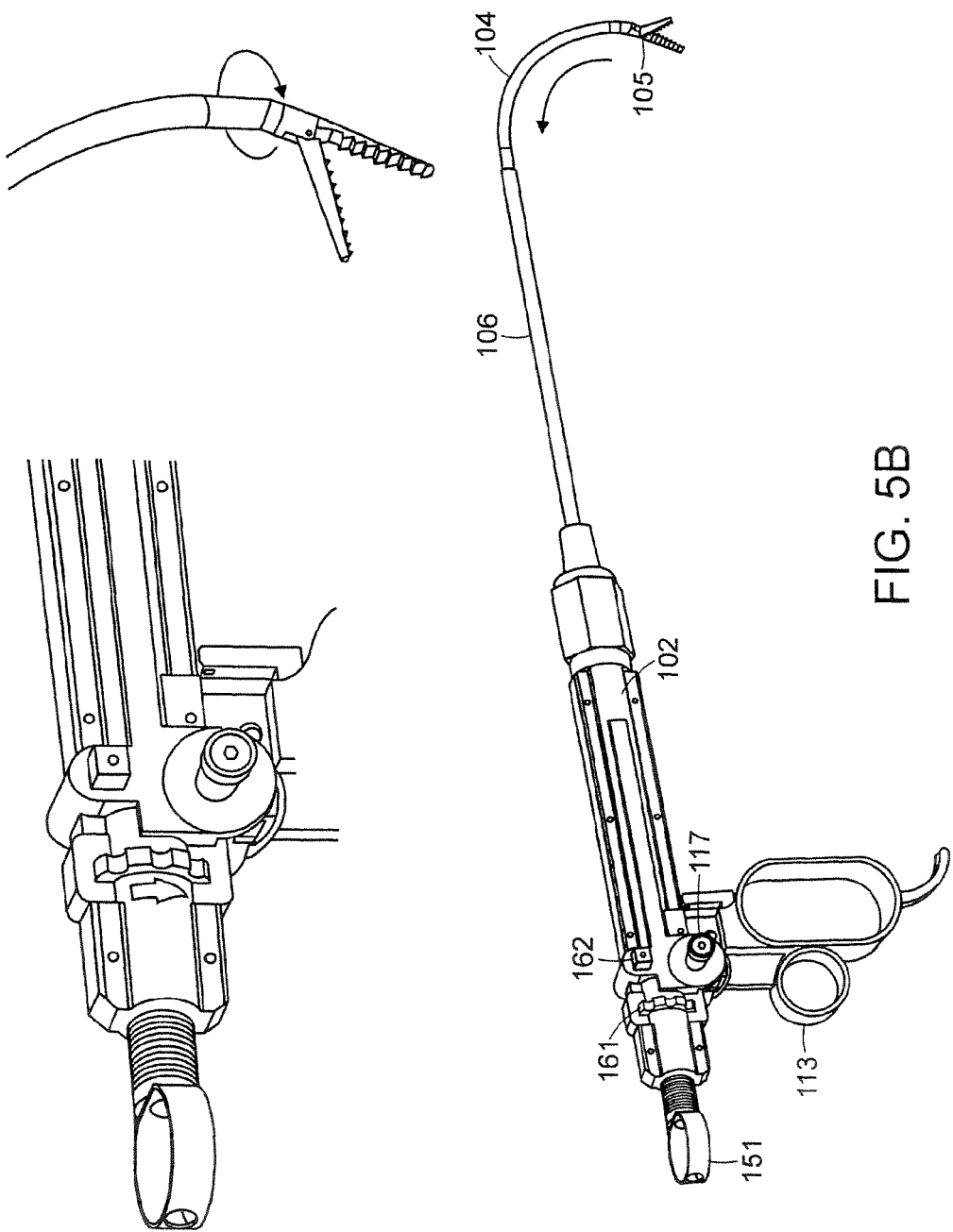
FIG. 5B shows a side view of a device in accordance with another embodiment of the present invention, wherein the distal end is in an extended curvilinear position, and a thumb actuated ring is provided.

In one embodiment, the degrees of freedom are provided by an actuating mechanism shown in FIGS. 5A, 5B, 10 and 11. The elongate body member 106 is interconnected with a proximal end 102 handle assembly, which is housed within handle 103. The body member 106 includes an outer body member 120, an inner body member 122, an articulating knuckle 124, and an operable end 105. Inner body member 122 is received within outer body member 120 and is interconnected with the slidable housing 130. The outer body member 120 is disposed about the inner body member 122 and is attached to the handle 103 (not shown) using conventional fastening means, such as a collett-like fastener or the like (e.g. as shown in FIGS. 5A and 5B). The body member 106, which is formed of the inner and outer body members 122, 120, can be removably interconnected and can be replacable in some embodiments. Three connecting points (a), (b), (c) are shown, for example in FIG. 11. An articulating knuckle 124 is positioned at the distal end of the inner body member 122 for connection to the operable end 105 either directly or indirectly. A jaw actuating rack 138 is located within the slidable housing 130. The rack 138 has ridges 140 along at least a portion of its length. A pinion 132 having ridges 142 that mate with ridges 140 on the rack 138 is positioned on the rack 138, and is in connection with an actuation mechanism 112 (which can be, for example, a trigger or ring or similar actuation mechanisms for engagement and manipulation by a finger or thumb). When the actuation mechanism 112 (e.g. trigger or ring) is manipulated (e.g. pulled), the rack 138 slides within the housing 130 which, in turn, pulls on the actuating rod 123 (FIG. 13) to actuate the operable end 105 (e.g. open and close the jaws). The pinion 132 can be pushed sideways so as to disengage the pinion ridges 142 from the rack ridges 140, and free the rack 138 to be extended or retracted smoothly. For example, a three-spoked hub 151, thumbring 152, or similar mechanism, can be positioned in connection with the rack 138 for extending or retracting the rack 138 distally or proximally. Motion of the rack 138 in a distal or proximal direction causes the inner body member 122, which is directly or indirectly in connection with the rack 138, to move. Such motion is defined as "rectilinear extension". Once the appropriate extension is achieved, the housing 130 can be locked in place by sliding the locking pin 170 to engage the slidable/rotatable housing 130. With the locking pin 170 engaged or not, the inner body member 122 can also be rotated with respect to the longitudinal axis of the device to further position the distal end 104 and operable end 105 as desired. This rotation is referred to above as the "rotation of the operable end". If desired, the outer body member 120 and the handle 103, which are fixed together (e.g. via a collett on a tapered lock), can rotate or move into and away from the hip joint capsule. These are referred to "rotation about the linear axis of the elongate body member" and "rectilinear extension" respectively. When the operable end 105 is positioned using these degrees of freedom, the trigger 112 can be used to manipulate the pinion 132 to move the rack 138 forward and backward relative to the housing 130, which pushes and pulls the push/pull rod assembly 136, which, in turn, opens and closes the grasping jaws or other movable elements on the operable end 108 ("operable end motion"). For example, FIG. 12 shows the trigger 112 in a forward position with housing 130 retracted, while FIG. 13 shows the trigger 112 in a backward position with housing 130 in an extended position.

Figure 12:
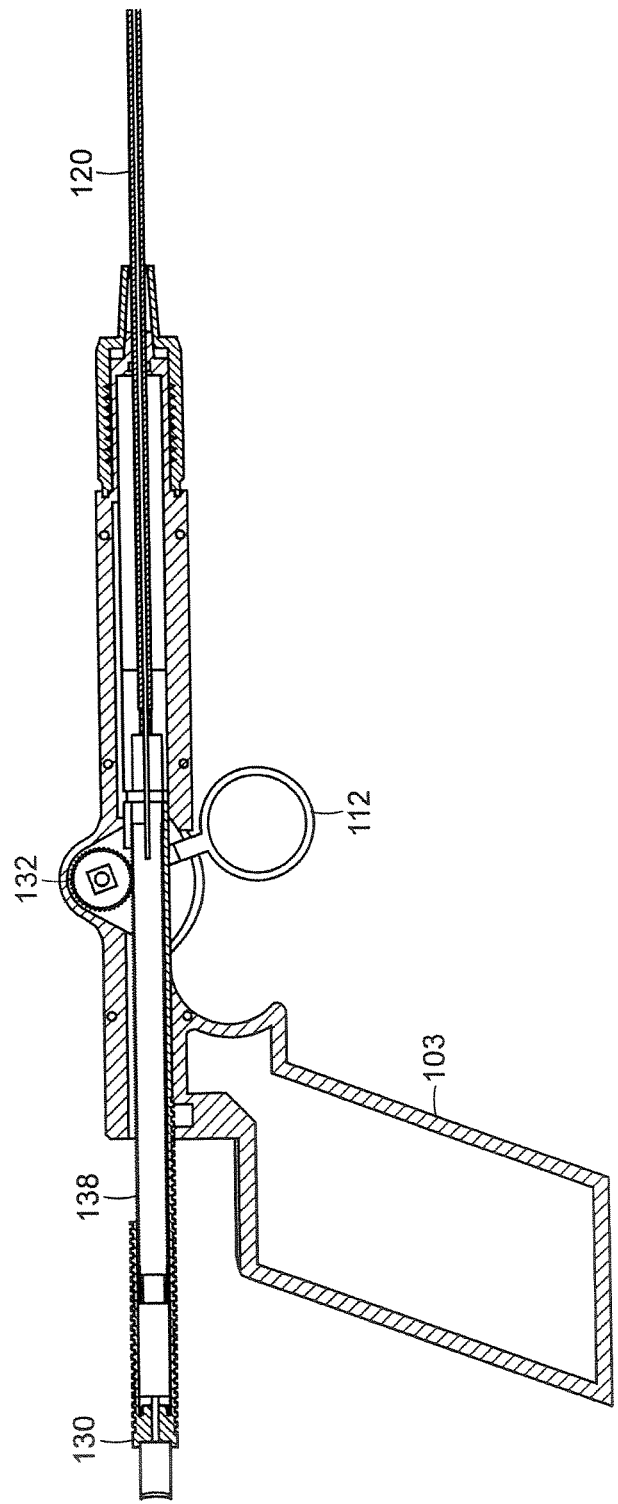
FIG. 12 shows a cross-sectional view of one embodiment of the handle, wherein the trigger is actuated to provide the distal end in a retracted position.

The rack 138, housing 130, pinion 132, and other elements can be enclosed in a proximal end portion of the device, such as the handle 103, for example, as shown in FIGS. 12 and 13. The handle 103 can be ergonomically shaped for comfort and access to the actuation triggers, rings, and other mechanisms by either the right or left hand. The handle 103 and its connection to the outer body member 120 is designed to withstand the manipulation and "prying" forces often employed to position the device. The trigger 112 is shown in both the retracted (FIG. 13) and extended (FIG. 12) positions. In some embodiments, the rack 138 has a spring (not shown) for spring loading, so as to pre-load the trigger 112 and allows the rack 138 to rotate with the housing 130. FIG. 14 shows another cross section view of this embodiment of the actuating handle, with the inner body member 122 retracted within outer body member 120.

In another embodiment, illustrated in FIGS. 18-21, the device is provided with a fixed-radius, pre-formed curvable distal end segment 214. The device 200 shown in FIG. 18 has a proximal end defining a handle 203, a distal end 204 defining an operable end 205 of the device 200, and an elongate body member 206 extending therebetween. The operable end 205 is rotatable, as shown, for example, in FIG. 21.

By combining one or more of the degrees of freedom discussed herein, precise positioning of the operable end 205 within the hip capsule can be achieved. Rectilinear extension can be achieved by the user holding the device by the handle 203 and simply moving the device by the handle in and out of the hip capsule. The user can further rotate the device about the linear axis of the elongate body member 206 by holding onto and rotating the handle 203. Motion about these two degrees of freedom can allow the user to begin to approach the coarse position within the hip capsule as desired. Further precise positioning of the device can be provided by providing curvilinear bending of the distal end segment 214 of the elongate body member 206 along its longitudinal axis into a desired arcuate shape. Such curvilinear bending can be achieved, for example, by any of the mechanisms described herein (e.g. wherein the device is provided with a fixed-radius, pre-formed curvable end segment, by advancement and withdrawal of the distal end segment 214 within and outside of an outer rigid member). The operable end 205 can further be positioned by rotation of the operable end 205 about the arcuate axis of the curved body member 206 as described herein. In those embodiments wherein the operable end 205 consists of a pair of intermating elements, e.g. graspers, punches, scissors, or the like, operable end motion/actuation can further position the operable end 205 as desired within the hip capsule.

Figure 18A:
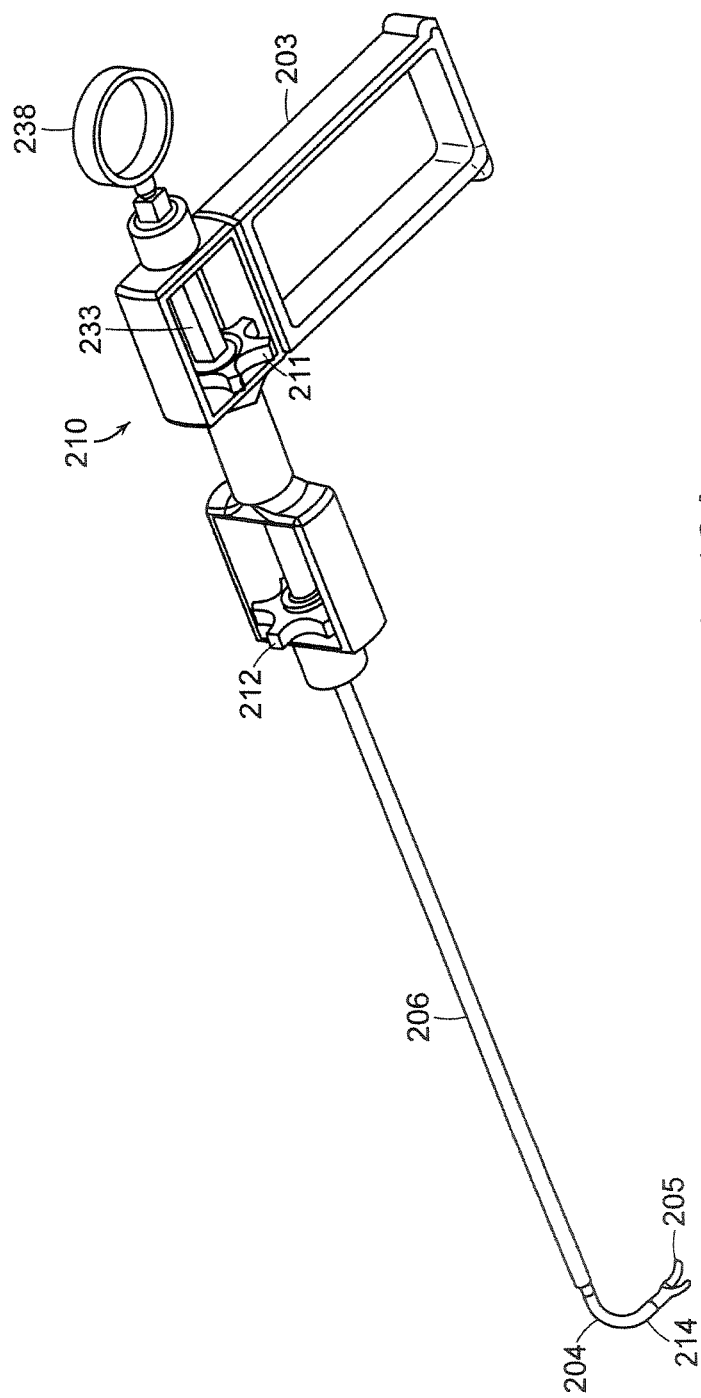
FIG. 18A shows a side view of a device in accordance with another embodiment of the present invention having a flexible distal end segment, wherein an actuation means is in a position that moves the flexible distal end segment forward.
Figure 18B:
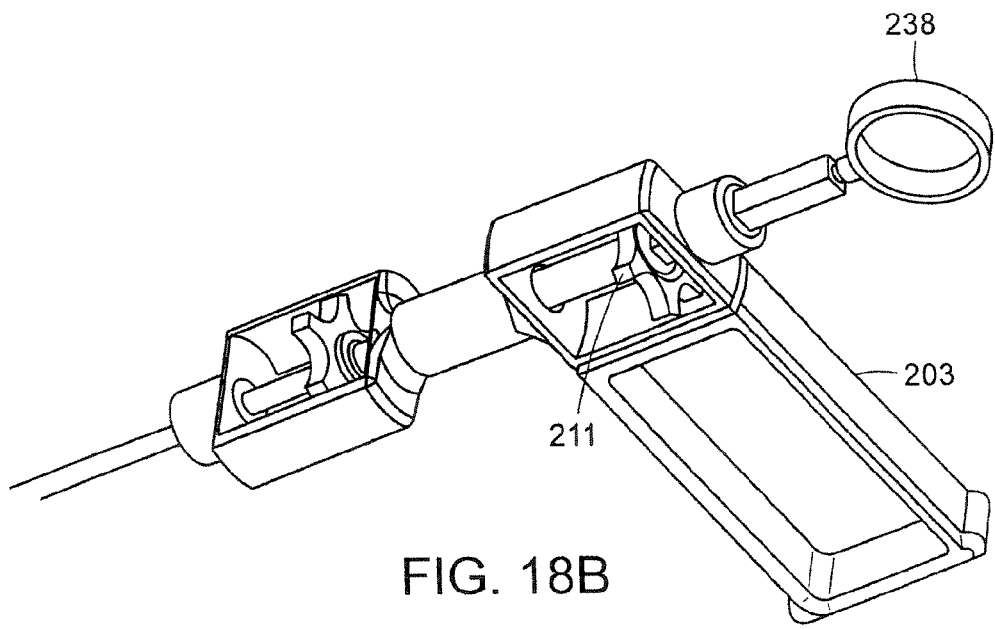
FIG. 18B shows side view of the handle of FIG. 18A with the actuation means is in a position that moves the flexible distal end segment backwards.
Figure 19B:
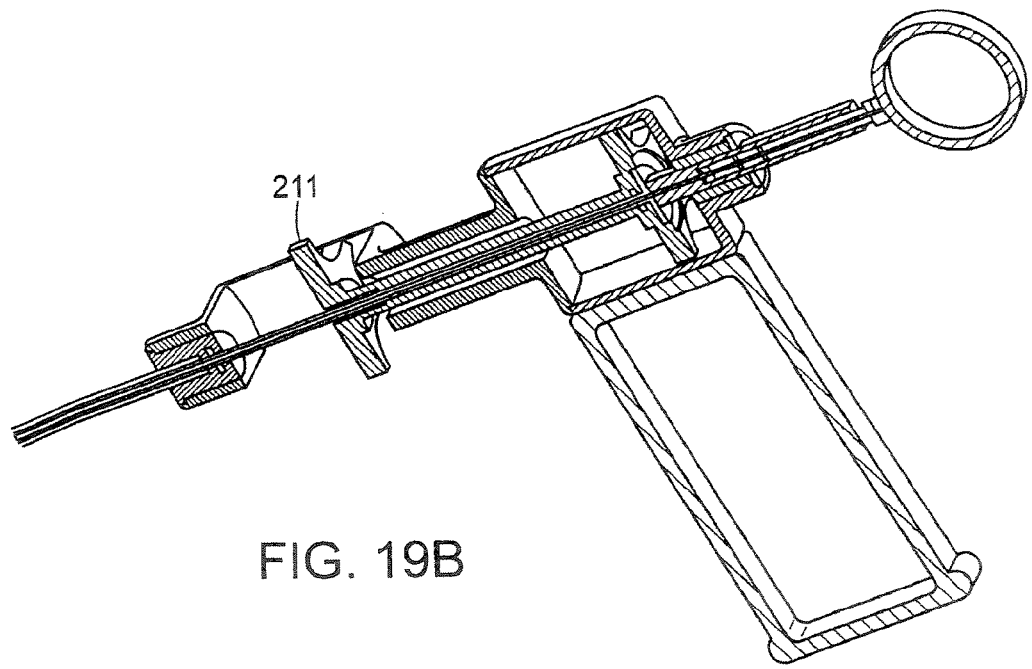
FIG. 19B shows a side cross-sectional detailed view of the handle of FIG. 18B.
Figure 19A:
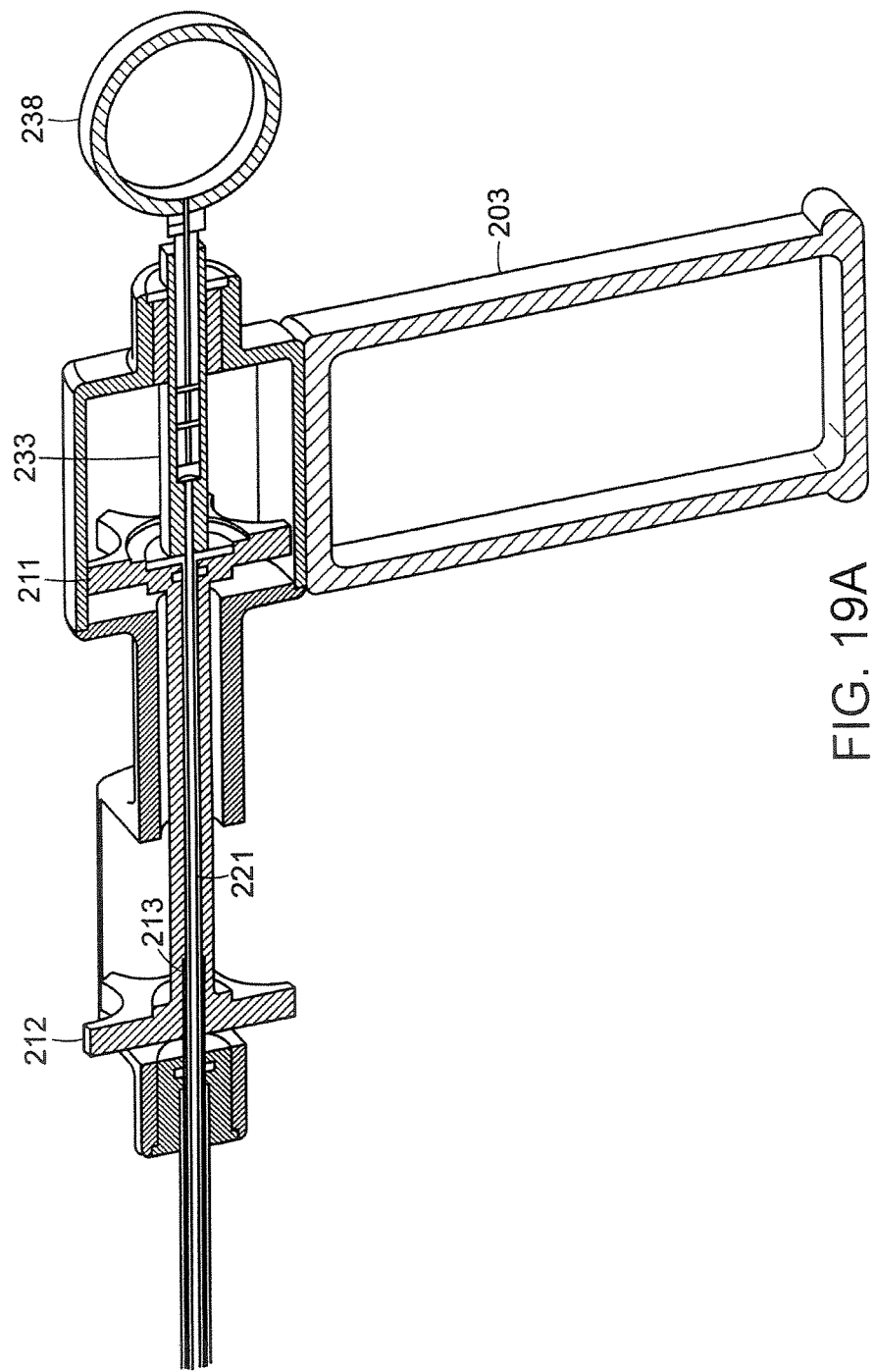
FIG. 19A shows a side cross-sectional detailed view of the handle of FIG. 18A.

One embodiment of a control means 210 for providing iterative rectilinear extension and curvilinear bending is illustrated in FIGS. 18A-B and 19A-B. The control means can be positioned, as shown, in the handle 203, or elsewhere in or along the device. For example, two knurled knobs 211 and 212 are interconnected to form a rectilinear extension control assembly. A user can use a thumb to push the knob 211 forward (e.g. as shown in FIGS. 18A and 19A), thereby causing the actuation means to slide forward and, in turn, to move forward the distal end segment 214. The user can further use, for example, the forefinger, to pull back the knob 212 like a trigger which, in turn, pulls the distal end segment 214 backwards (e.g. as shown in FIGS. 15B and 19B).

As shown in FIGS. 19 and 20, an inner tube 213 connects the control means 210 to the distal end segment 214 via an adapter 215. The inner tube 213 is slidably and rotatably positioned within at least a portion of an outer body member 220. The outer body member 220 is fixed relative to the handle 203. The outer body member 220 may be rigid or semi-rigid. A preformed member 219 can be positioned within the distal end segment 214 and is rotationally constrained to rotate with the handle 203 and is slidably constrained to slide with the distal end segment 214. Advancement of the inner tube 213 beyond the distal end of the outer body member 220 can be controlled by the control means 210. For example, the inner tube 213 can extend from the distal end of the outer body member 220 to the control means 210. In one embodiment, the inner tube 213 is received within at least a portion of the outer member 220, and is in connection with the control means 210. The control means 210 is slidably received within the handle 203 between an extended position (shown in FIGS. 18A and 19A), and a retracted position (shown in FIGS. 18B and 19B). When the preformed member 219 is within the outer body member 220, the preformed member 219 is constrained in the same shape (e.g. straight or other shape) as the outer body member 220. When the control means 210 is extended, it pushes the inner tube 213 and preformed member 219 in a distal direction and out of the outer body member 220. When the control means 210 is retracted, it pulls the inner tube 213 and preformed member 219 in a proximal direction and inside of the outer body member 220.

Curvilinear bending can further be provided as illustrated in FIGS. 18A and 20. Control means for curvilinear bending can, for example, be positioned within the handle 203. A hub 232 can be rotatably positioned in connection with the control means 210 in manner that causes the hub 232 to translate and rotate with the control means 210. The curvilinear bending, in this embodiment, can be controlled by the degree of extension of the preformed member 219 from within the outer body member 220. The curvilinear shape of the distal flexible end 214 can be controlled by the pre-formed shape of the preformed member 219. The preformed member 219 can, in some embodiments, be made from nitinol or spring temper stainless steel for limited flexural loading. In its unstressed state, the preformed member 219 can be formed into a radius that is best suited for the intended purpose. For the hip capsule, this is generally about 25 mm, although, different users of the device may have preferences for smaller or larger radii. In this embodiment, the preformed member 219 can be made from tubular material that provides the flexible distal end 214 with adequate structural support, in some instances stiff structural support, and which can further provide cannulated access (e.g. for an actuation wire/cable). For smaller radii, the preformed member 219 can be provided with a flat ribbon cross section. The dimensions can be chosen to meet the requirements of the design. These design aspects can include a reasonable force to withdraw the preformed member 219 back into the outer body member 220 and the stiffness and structural support that it provides to the flexible distal end 214. The preformed member 219 can be fixed to a collar at each end (230, 231) to provide a bearing surface over which the flexible distal end 214 can rotate. For example, the collar 230 can be fixed to the preformed member 219. A slider assembly 233 can be designed and disposed so as to translate with the control means 210 but not rotate. The slider assembly 233 can be provided so as to restrain the preformed member 219 in the plane of the handle 203 and to prevent it from rotating when the operable end 205 is rotated about its arcuate axis.

This control means 210, which includes the two knobs 211 and 212, the inner connector/tube 213, the adapter 215, the flexible distal end 214, the hub 232, and the operable end 205, all translate as a single element along the axis of a fixed preformed shape of preformed member 219. When the knob(s) is moved forward, the whole assembly moves forward. Similarly, when the motion of the knobs are reversed, the entire assembly translates back into the outer body member 220.

Figure 21:
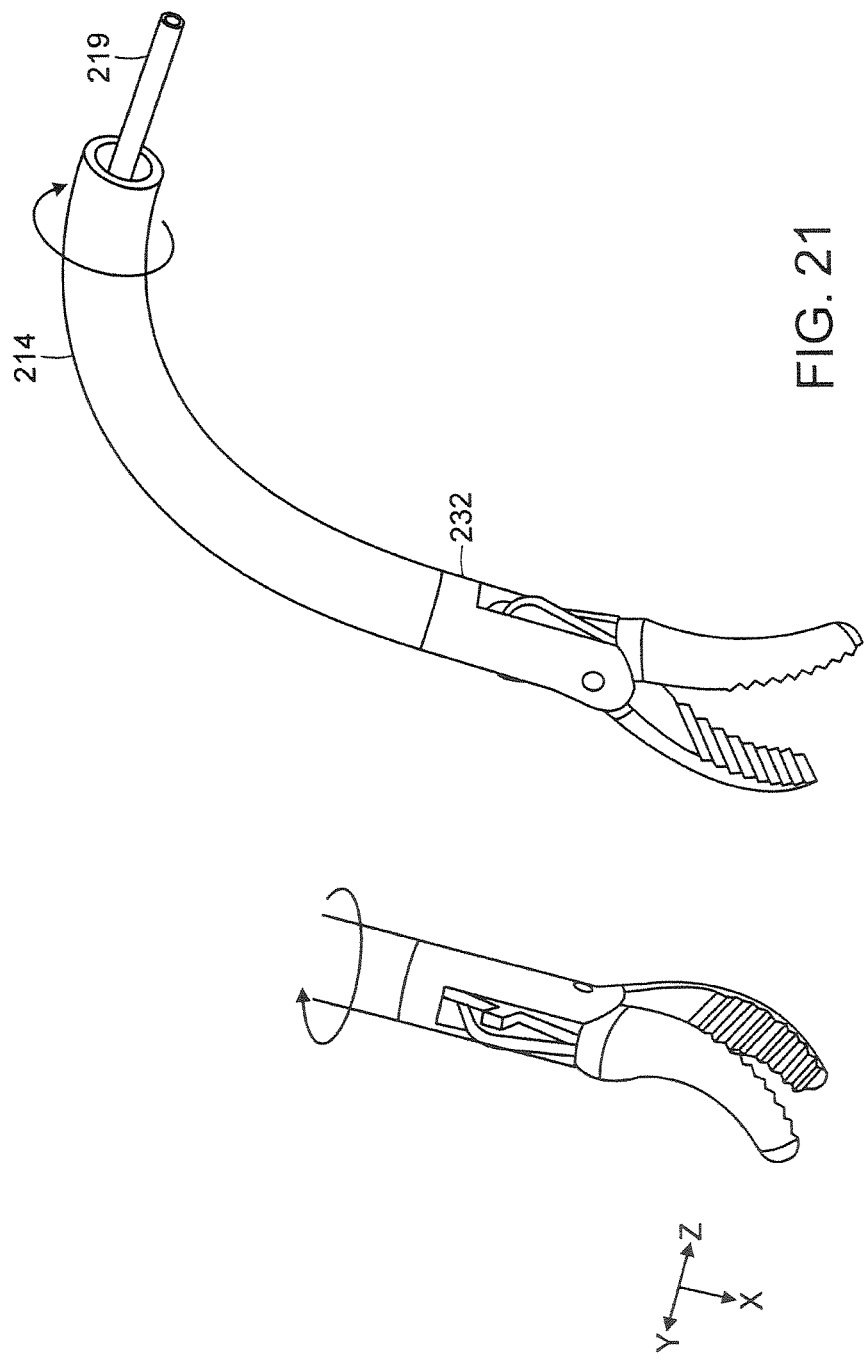
FIG. 21 shows schematically, rotation of the operable end and distal end segment of FIG. 18A.

Rotation of the operable end 205 of the device can be provided by rotation control means which can also be positioned at the distal end 204, such as in the handle 203 as shown, for example, in FIGS. 18A-B and 19A-B. In some embodiments, the control means 210, which provides extension and bending as described above, can also provide rotation. In one embodiment, one or more of the knurled knobs 211 and 212 rotate with respect to the handle 203 (e.g. for convenience, the knobs 211, 212 can be disposed for thumb-actuated rotation and/or forefinger rotation, for example, thumb rotation of knob 211 and forefinger rotation of knob 212). The preformed element 221 and preformed member 219 can be constrained so as to remain fixed with the handle 203 as one or more of the knobs 211, 212 rotate. The inner tube 213 can be secured to control means 210 so as to move with the control means 210. Thus, when the control means 210 moves distally/proximally, the inner tube 213, likewise, moves distally/proximally. The inner tube 213 is in connection with the flexible distal end segment 214, for example, via an adapter 215. The flexible end segment 213 is, in turn, in connection with the hub 232 of the operable end 205. This mechanism, which includes the knobs 211, 212, inner tube 213, adapter 215, flexible distal end 214, hub 232, and operable end 205 can be disposed so as to rotate as a single element about preformed element 219. For example, FIG. 20 illustrates one position of the operable end 205, while FIG. 21 shows another position of the operable end 205 after rotation of one or more knobs 211, 212 by 90 degrees. This rotation is independent of the translation, bend, and operable end degrees of freedom motion.

The operable end 205 can be in the form of movable portions, e.g. two parts such as jaws 235 and 236, that move relative to each other. In such embodiments, an actuation mechanism such as a cable (not shown) can be attached to a joint 234 that causes the jaws 235, 236 to move relative to one another. The actuating mechanism can be positioned within the elongate body member 206 (e.g. within or along preformed member 219) and is attached to the actuating thumb ring 238 such that the jaws 235, 236 close when the thumb ring 238 is moved forward and open when the thumb ring 238 is moved backward (or vice versa).

Figure 10:
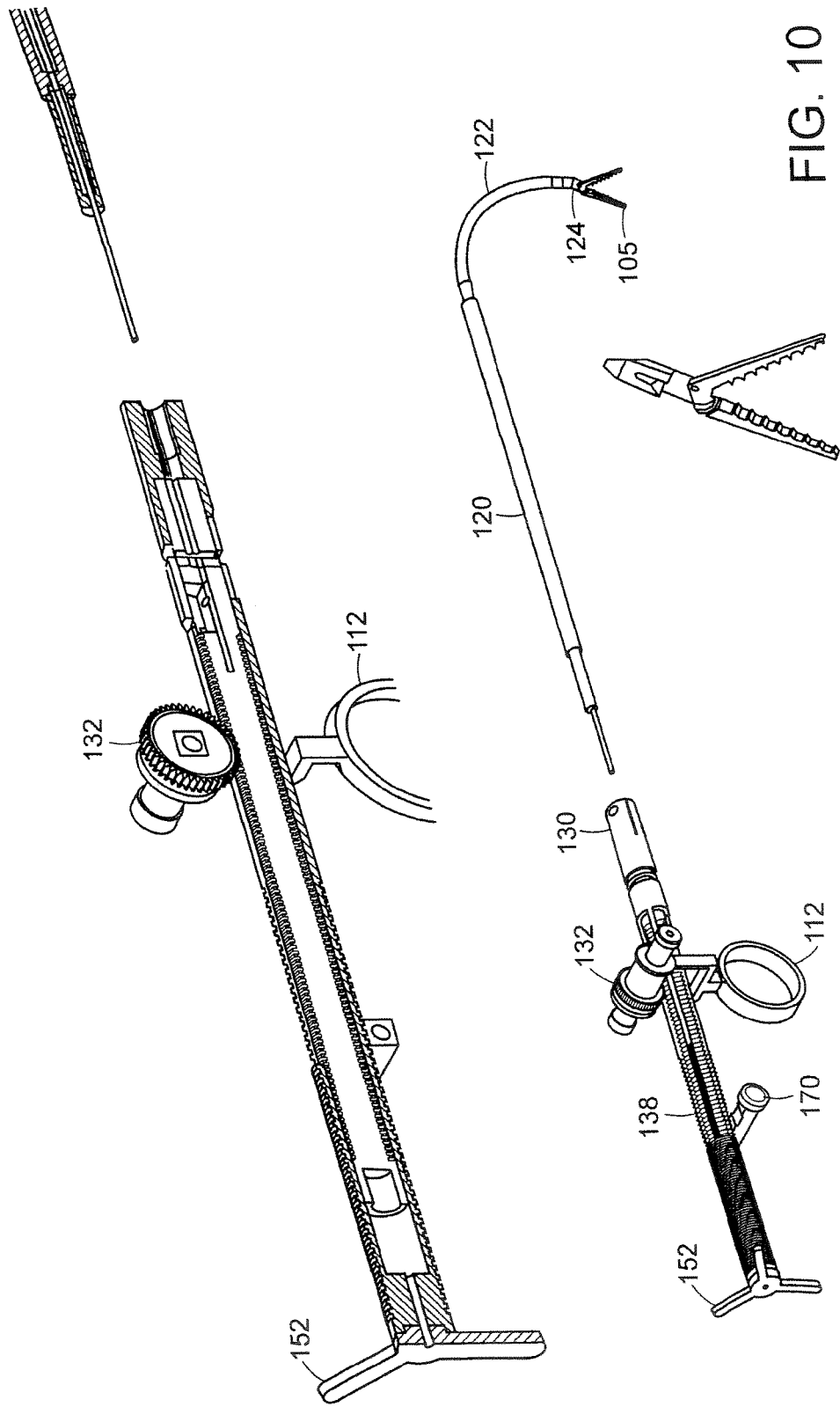
FIG. 10 shows an embodiment of an actuating handle as it can be used to extend an inner tube out of an outer tube and provide curvilinear motion of the inner tube and distal end.

Another device embodiment shown in FIG. 5B, positions the user's hand in a position common to that used to hold graspers and punches. A thumb ring 151 (FIG. 5B) or similar manipulation element (e.g. three-spoked hub 152, FIGS. 5A and 10) be used to linearly translate the operable end 105. The operable end 105 can be actuated (e.g. actuation of jaws) by moving the ring 113 shown in FIG. 5B. This configuration can utilize a rack 138 and pinion 132 mechanism as shown in FIG. 10 to effect the translation, arcuate rotation, and operable end actuation of the device. A release member 117 can be provided to release the rack 138 from the pinion 132 (e.g. using forefinger). Thus, for example, the thumb ring 151 can be used to translate the slidable/rotatable housing 130 (e.g. as shown in FIGS. 5A, 5B, 12, and 13) and the inner body member 122, while the knob 161 can be manipulated to rotate the slidable/rotatable housing 130 and the inner body member 122, and the trigger 113 can be manipulated to translate the rack 138 which actuates the operable end (e.g. opens and closes jaws). A locking member 162 can be used to lock the slidable/rotatable housing 130 in place, while a release member 117 can be used to engage/disengage the pinion 132.

Another embodiment of the device shown in FIG. 5A positions the user's hand in a position common to gripping a pistol. In this configuration, the thumb can be used to manipulate a three-spoked hub 151 (or other type of manipulation device) to effect linear translation and bending of the inner body member 122. Further, rotation of the three-spoked hub 151 can provide rotation of the operable end 105 as shown in the bottom figure of 5A. The forefinger can be used to actuate the operable end (e.g. jaws) using the trigger 112. This configuration can utilize a rack 138 and pinion 132 mechanism as shown in FIG. 10. A release member 117 can be provided to release the rack 138 from the pinion 132 (e.g. using forefinger). A locking means 169 can further be provided to lock the slidable rotatable housing 130 into a particular position.

In another embodiment, illustrated in FIGS. 22-26, the device is provided with a variable radius curvable distal end segment 314. The device 300 shown in FIG. 22 has a proximal end 302 defining a handle 303, a distal end 304 defining an operable end 305 of the device 300, and an elongate body member 306 extending therebetween. The operable end 305 is rotatable, as shown, for example, in FIG. 25. In the illustrated embodiment, the operable end 305 includes a lower jaw member 342 to which an upper jaw member 344 is pivotably attached. As will be discussed in more detail hereafter, the lower jaw member 342 may be connected to a flexible drive shaft 341 that may be selectively rotated within the curvable distal end segment 314, thereby causing the operable end 305 to rotate relative to the distal end segment 314 about its arcuate axis.

By combining one or more of the degrees of freedom discussed herein, precise positioning of the operable end 305 within the hip capsule can be achieved. Rectilinear extension can be achieved by the user holding the device by the handle 303 and simply moving and guiding the device by the handle in and out of the hip capsule. The user can further rotate the device about the linear axis of the elongate body member 306 by holding onto and rotating the handle 303. Motion about these two degrees of freedom can allow the user to begin to approach the coarse position within the hip capsule as desired. Further precise positioning of the device can be provided by providing curvilinear bending of a distal end segment 314 of the elongate body member 306 about its longitudinal axis into a desired arcuate shape.

In this embodiment, curvilinear bending of the distal end segment 314 is an iterative process of extending and bending. The control means for curvilinear bending of the distal end segment 314 can be positioned at the distal end, for example, in the handle 303. One or more pairs of tensioning cables 301, for example, as shown in FIG. 23 terminate at a thumbwheel-like or cam-like rotational device 310. As the rotational device 310 is rotated, one of the paired tensioning cables 301 is put into tension. A tensioning means 311 is positioned to keep non-tensioned cables in sufficient tension to retain its position in the handle 303, i.e. securely positioned over guides 324 that can be provided for proper actuation. A locking means 312 can be provided against the rotational device 310 to secure the rotational position of the rotational device 310 and subsequently secure the degree of bending of the distal flexible portion 314.

The pairs of tensioning cables 301 terminate distally at a distal portion 315 of the distal end segment 314 as shown, for example, in FIG. 24. The distal flexible portion 314 is shown as comprising of a series of vertebrae 331 interconnected by a integral web 332, which is in the form of a beam-like member that interconnects the vertebrae 331. In some embodiments as shown in the figures, the entire distal flexible portion, including the vertebrae 331 and web 332, is a single molded part. In other embodiments, while generally more expensive, the distal end segment 314 can be formed of a plurality of vertebrae individually formed and strung together, and relying on a pivoting hinge-like arrangement between the vertebra to provide the bending shape. By using an interconnecting web 332, the resulting bend will be in accordance with the classic predictions of any beam subjected to moment forces on each end. This distributes the stress over the length of the beam (and, here, the length of the distal end segment 314) and relieves any point of localized stress that would result if the vertebrae were hinged together at points. The vertebrae 331 can be generally cylindrical in shape, as shown, or of any other geometric shape. The principal of operation is that as one of the paired cables 301 is put into tension, the vertebrae 331 on that side compress as the interconnecting web 332 bends. The degree of bending is proportional to the stress in the cables 301. The distal end segment 314 can be fabricated of any conventional materials used in forming surgical devices and, for example, can be fabricated of a polymeric resin with mechanical properties that allow repeated bending stress in the elastic limit of the molded material.

The distal end segment 314 may also comprise a substantially non-bendable proximal portion 308. At least a portion of this proximal portion 308 may be disposed within and fixedly attached to the distal end of the elongate body member 306 as shown in FIG. 24.

Figure 24A:
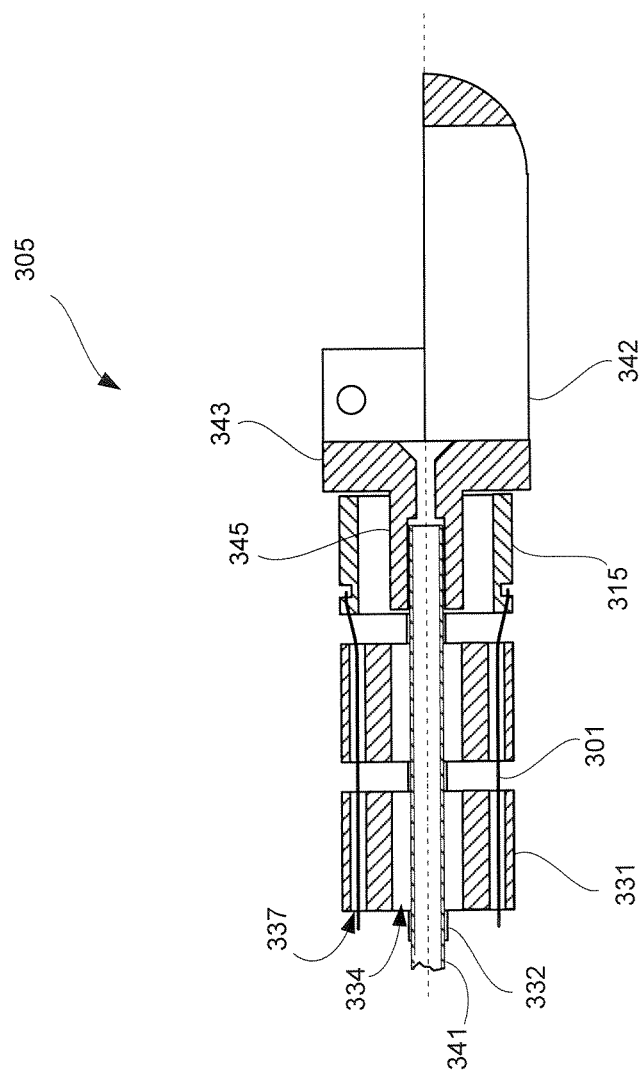
FIG. 24A shows a side cross-sectional view of the operable end of the device of FIG. 22.
Figure 25A:
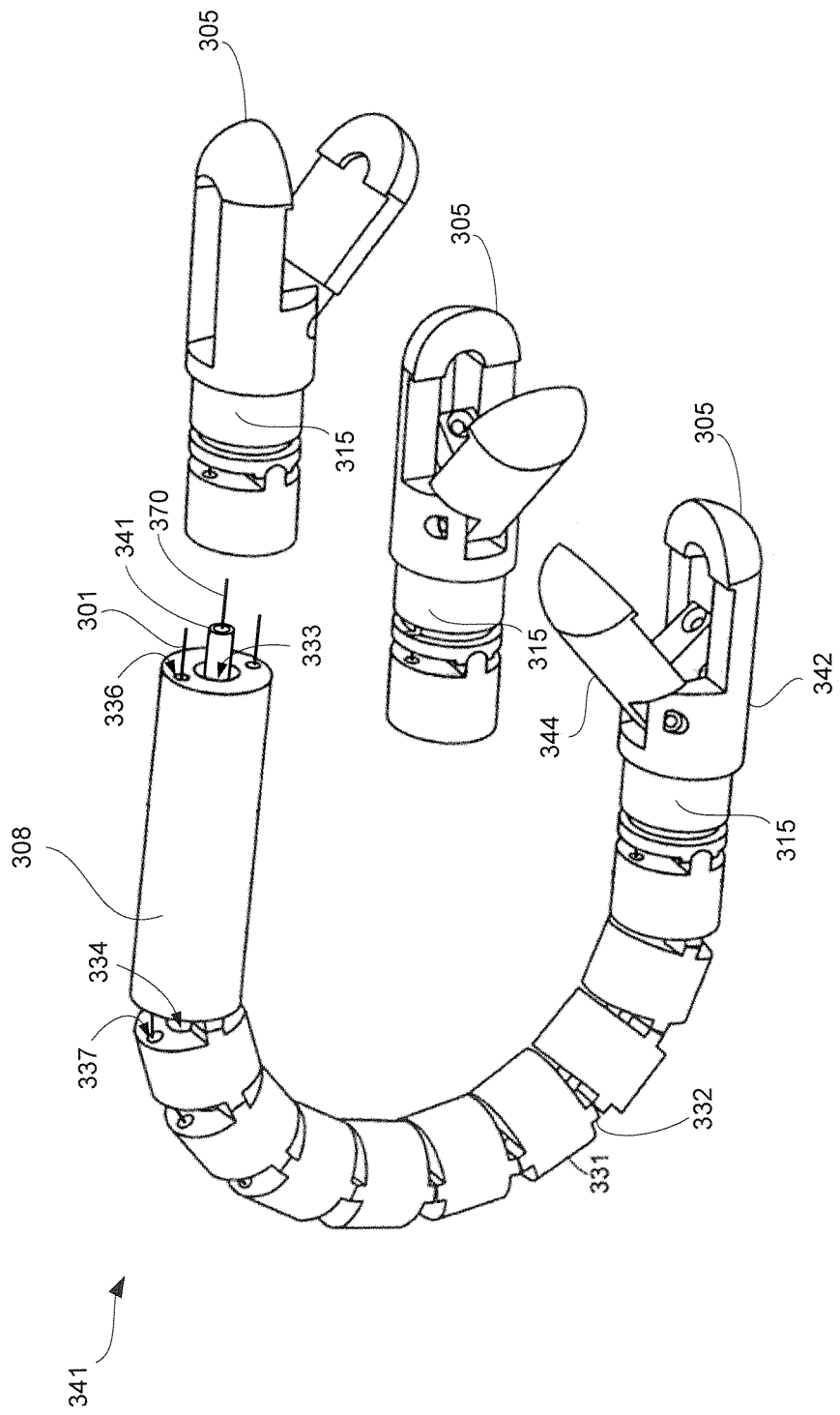
FIG. 25A shows schematically, rotation of the operable end relative to the distal end segment of FIG. 22.
Figure 25B:
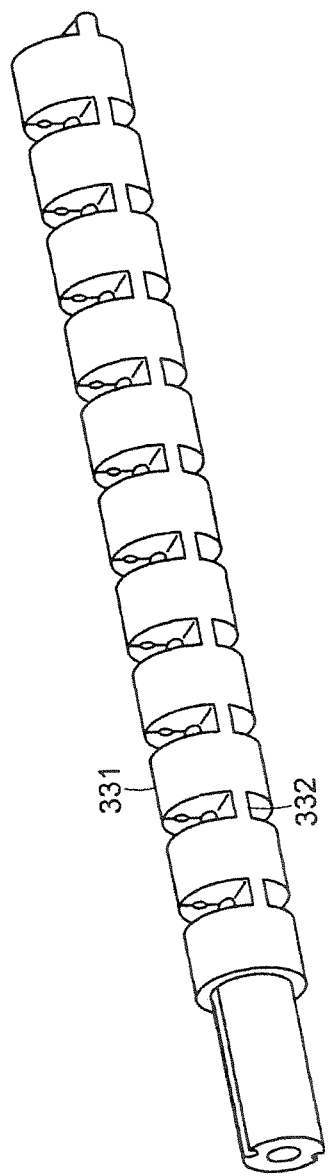
FIG. 25B shows a side view of one embodiment of the distal end segment of FIG. 22 in a straight position.

The position of the operable end 305 can further be refined by rotating the operable end 305 about it's arcuate axis as shown, for example, in FIG. 25A. Rotation control means 350 can be mounted in the handle 302 as shown, for example, in FIG. 23. A rotation extension tube 340 is secured in the rotation control means 350 in a manner that causes it to rotate as a rotational wheel 351 is rotated. A flexible drive shaft 341, which can be hollow, as shown in FIG. 24, is in connection with the extension tube 340 in a manner that causes it to rotate about its arcuate axis as the rotational wheel 351 is rotated. In turn, as best seen in FIG. 24A in which the upper jaw and actuation wire 370 are omitted for clarity, the bearing face 343 of the lower jaw 342 is secured to the drive shaft 341 by bearing face extension 345 in a manner that causes it to rotate as the drive shaft 341 and the rotation wheel 351 rotate. This causes the entire operable end 305 to rotate relative to the distal-most vertebra 315 when the rotational wheel 351 is rotated. The proximal portion 308 and the vertebrae 331 of the distal end segment 314 may be formed with longitudinal passages 333, 334 through which the flexible drive shaft 341 may be passed to connect the operable end 305 to the rotation control means 350. A spring-loaded pawl 353 can further be provided so as to secure the rotational position of the operable end 305 once the desired position has been achieved. The rotation control means 350 may also be spring-loaded 352 in a manner that keeps the bearing face 343 of the lower jaw 342 in contact with the distal portion end of the distal-most vertebra 315 of distal end segment 314.

Figure 22:
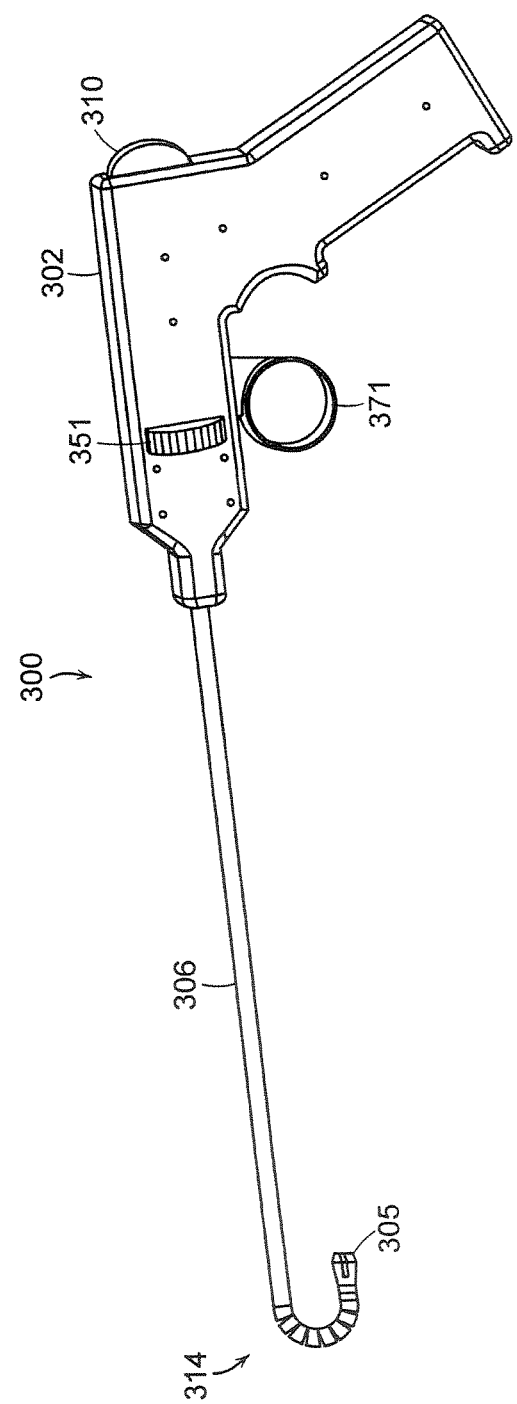
FIG. 22 shows a side view of a device in accordance with another embodiment of the present invention having a flexible distal end segment formed of vertebrae.
Figure 25C:
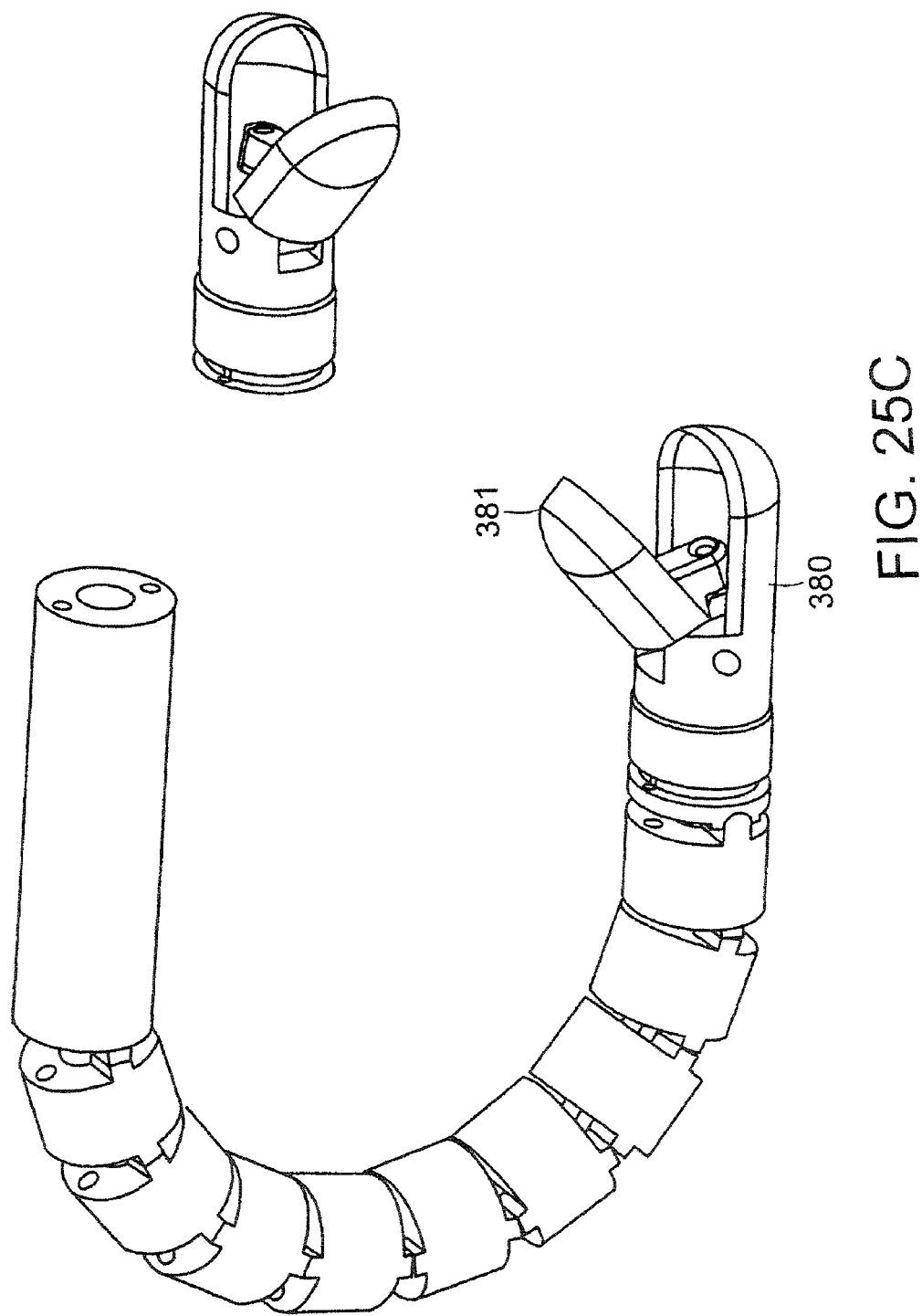
FIG. 25C shows a side view of another embodiment of the operable end of FIG. 22.
Figure 25D:
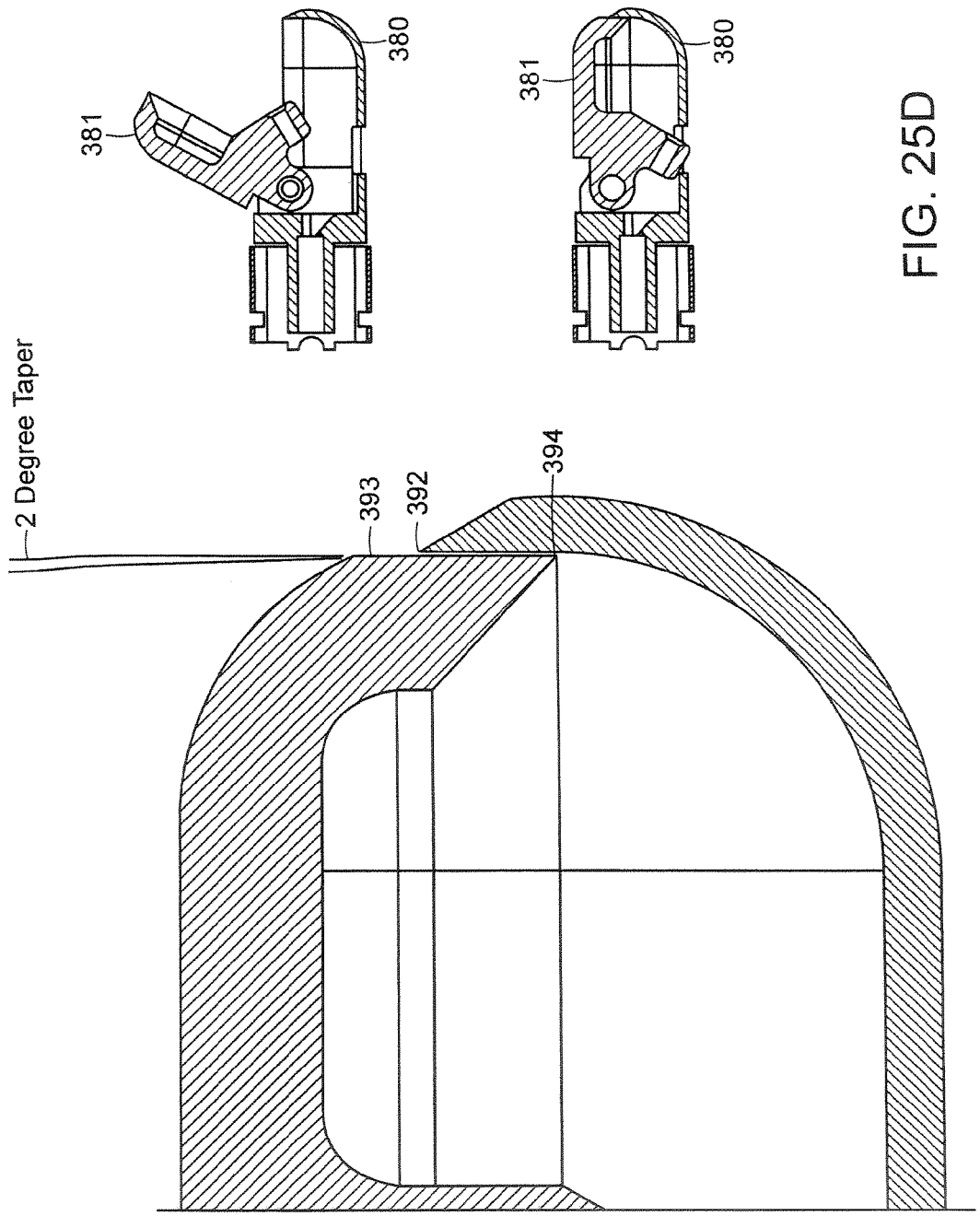
FIG. 25D shows a side view of the operable end of FIG. 25C in the form of overlapping jaws in an open and closed position.

One type of actuation means in the form of an actuating trigger 371 for controlling the movement of the operable end 305 is shown in FIGS. 22 and 23. The actuating trigger 371 can use a cam shaped surface 372 to control the shape of a wire 370 and to provide support when the wire 370 is in compression. A proximal end of the wire 370 is fixed to the cam shaped surface 372 in a manner that causes the wire 370 to be put into tension when the trigger 371 is pulled and into compression when the trigger 371 is pushed forward. The wire 370 is fixed at its distal end in the operable end 305, as shown in FIG. 24, in a manner that causes the operable end 305 to actuate when the trigger 371 is pushed and pulled (e.g. for jaws 380/381 to close when the trigger 371 is pulled and open when the trigger 371 is pushed forward or vice versa, as shown in FIGS. 25C and 25D). As noted above, the flexible drive shaft 341 may be formed as a tube to provide a passage for the wire 370 through the distal end segment 314.

Figure 11:
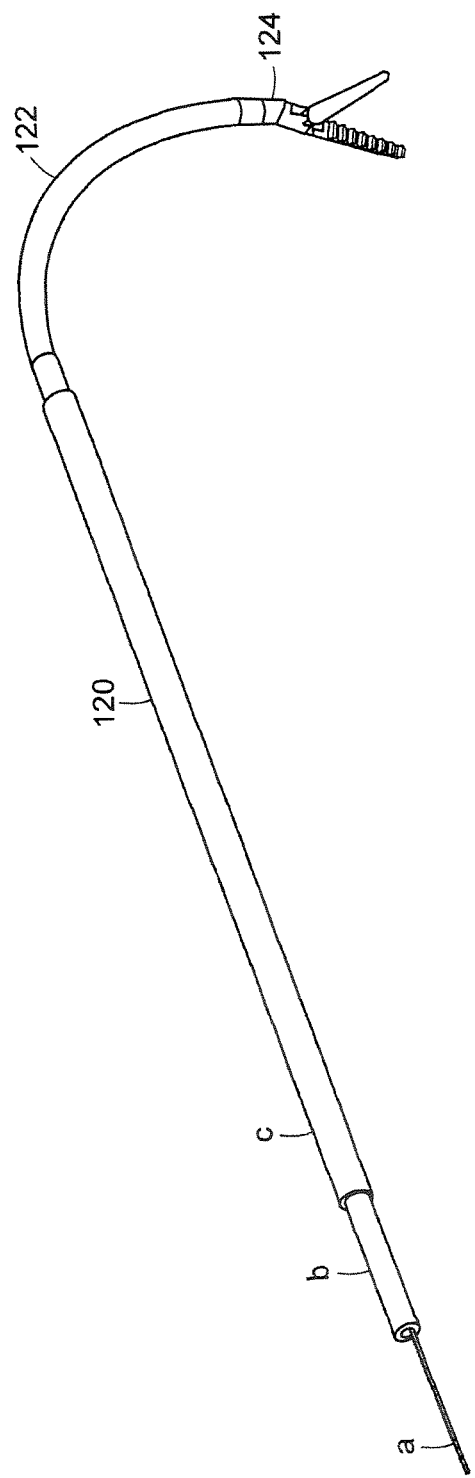
FIG. 11 shows an embodiment of the body member with a distal end in a curved and extended position.

In one embodiment, the operable end 305 is in the form of grasping jaws, as shown in FIGS. 25A, 21, and 11. In FIG. 25A, the operable end 305 includes upper and lower jaws 342, 344. In an alternate embodiment, the operable end 305 is in the form of overlapping jaws 380, 381, as shown in FIGS. 25C and 25D. These overlapping jaws 380, 381 can be designed to resect, or punch, tissue. The rotation and actuation means for the embodiments of FIGS. 25C and 25D can be in accordance with any of those set forth herein. However, the edges of the jaws 380, 381 overlap and are sharpened as shown in FIG. 25D in a manner that causes the sharpened edge of one jaw to contact and slide along the face of the mating jaw. Referring to FIG. 25D, the sharpened edge of one jaw, which can be, for example, a fixed jaw 380, is designed to contact with and slide along the ground face of the other jaw, for example, a moveable jaw 381, as the movable jaw 381 is closed against it. Similarly, the sharpened edge of the movable jaw 381 can be designed to come into contact with and slide along the ground face of the fixed jaw 380 as the movable jaw 381 is closed against the fixed jaw 380. To enable this contact, the edge of the movable jaw 381 can be ground or formed to a slight taper, the leading edge of which just clears the leading edge of the fixed jaw 380 and moves closer to it as the jaws are closed. The closing movement of the jaws continues until contact is made between the jaws in the manner described. In some embodiments, if desired, both jaws 380, 381 can be movable.

Because the distended hip joint capsule is typically filled with circulating saline at a slight pressure, the pressurized saline will leak from any open path in the device. Thus, these open paths should be sealed. For example, the leak path around the actuating wire can be sealed, for example, with an embedded silicone element 390. The leak path around the rotation extension tube 340 and tension cables 301 can also sealed, for example, with an embedded silicon element 391. The leak path around the elongate body member 306 can be sealed using conventional seals used in conventional cannulas. Other conventional sealing techniques and materials can also be used.

The basic handle type and actuation mechanism(s) can vary, based on the curvilinear/bending motion, rotational motion, and linear actuation/rectilinear extension principles disclosed above as well as the specifics of the operable ends as discussed herein. The handles can be reusable and sterilizable. The operable ends can be single-use sterile disposable devices, or reusable and sterilizable. The entire device can also be reusable and sterilizable or can be a single-use sterile disposable device.

Figure 16:
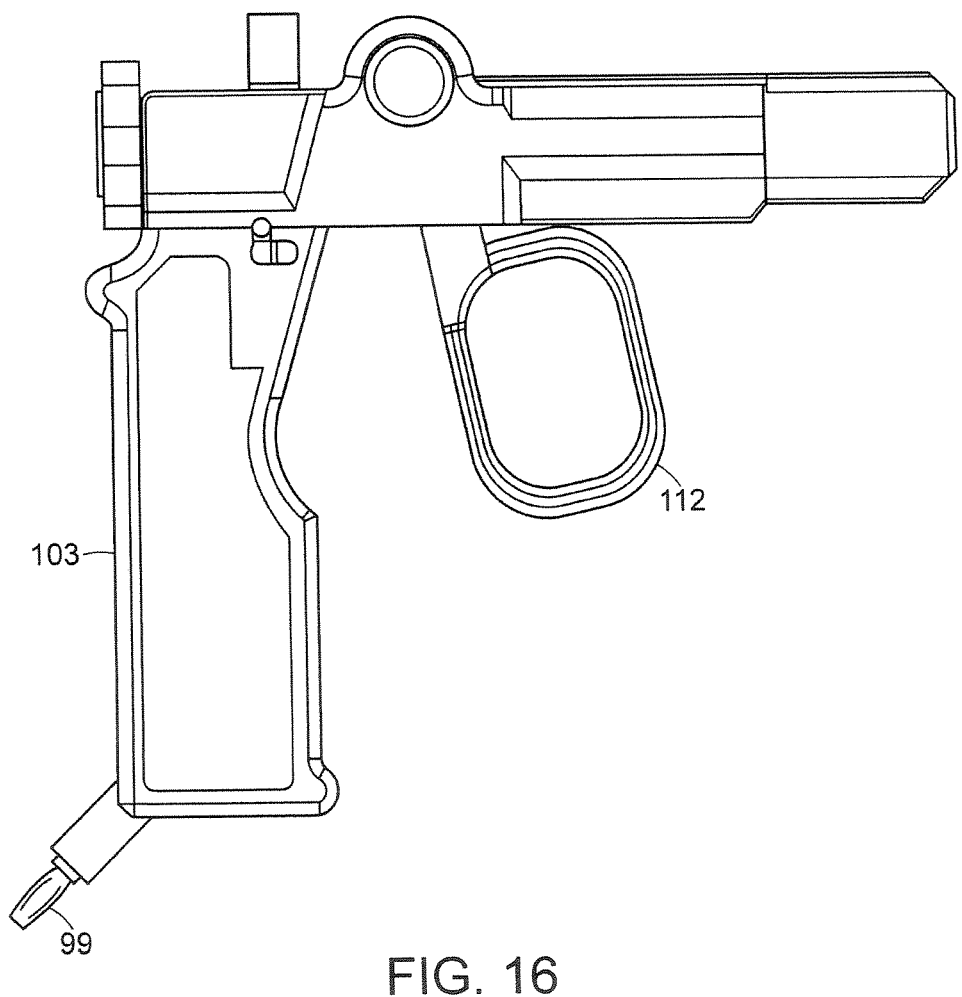
FIG. 16 shows an embodiment of a handle used for electrocautery applications.

In some embodiments, the device provides RF electrocautery. In such embodiments, the handle of the device can provide the curvilinear/bending motion, rotational motion, operable end motion, and linear actuation/rectilinear extension principles disclosed above as well as power leads for interconnection with an RF power generator. The device can further be provided with the appropriate types and positions of electrical insulative materials. Such materials can be housed in the elongate body member of the device and/or the handle. A schematic of an RF handle is shown in FIG. 16. The basic features of the device can be the same as those provided for graspers, scalpels, dissectors, and other operable ends. The device will further include power wires within the device (e.g. inside the flexible inner body member) electrically interconnected with a power connector 99, as well as the appropriate insulative measures (e.g. between the inner and outer body members). In some embodiments, the RF operable end is in the form of a mono-polar tip, which has no moving parts. In other embodiments, the RF operable end is in the form of a bi-polar tip, which includes a pair of movable electrode (jaws). In bi-polar applications, the opposing jaws generally are electrically insulated from each other. The basic handle type and actuation mechanism(s) for RF devices can vary similar to those provided for graspers, scalpels, dissectors, and other devices described herein. Such variations can be based on the curvilinear/bending motion, arcuate rotation, and linear actuation principles disclosed above as well as the specifics of the operable ends as discussed herein. The handles can be reusable and sterilizable. The operable ends can be single-use sterile disposable devices, or reusable and sterilizable. The entire device can also be reusable and sterilizable or can be a single-use sterile disposable device.

Further, interchangeable operable ends in the form of a multiplicity of electrocautery tips can be provided to make available the numerous shaped electrodes that are used by surgeons. For example, mono-polar tips have no moving parts can be provided as well as bi-polar tips which include a pair of movable electrode (jaws). In one embodiment, the device is in the form of a mono-polar device and the handle can be devoid of an operable end actuation mechanism discussed above In other embodiments, the device provides visualization of the entire capsule via a camera positioned as an operable end in combination with any of the basic embodiments described herein. Any conventional camera mechanism and associated components can be used. In one embodiment, shown in FIGS. 17A and B, the camera is an electronic CCD device 532 positioned within a mounting cylinder 533. Distal to the CCD are the lenses 534 that function to shape the image fed to the camera. Included among the lenses 534 is an angled lens that that shifts the field of view to something off axis of the camera (e.g. 30.degree. off axis). This is useful to provide the surgeon with a more direct image of the surgical target. Surrounding the CCD is a bundling of fiber optics 531 that are potted into arc-shaped areas formed between the round mounting cylinder 533 and a CCD chip 532. These fiber optics 531 transfer light from the distal end of the device (e.g. handle 510) to the camera tip, and are angled to be normal to the distal lens face. The signal wire bundle 506 and the fiber optic 531 can be co-located within the rotation tube 503 that extends though the outer tube 520 to the handle 510.

A rotation tube 503 is fixed to a rotation knob 505 in the handle 510 and a light-focusing enclosure 502. As the knob 505 is rotated, the light focusing enclosure 502 and the rotation tube 503 are likewise rotated, which, in turn, rotates an adapter 535 at the distal end of the distal flexible portion 530. The mounting cylinder 533 and all of the camera components mounted therein, are rotatable with the adapter 535.

The fiber optics 531 are terminated at the focus of the light-focusing enclosure 502. The fiber optics 531 are potted together and polished to provide a mirror smooth surface to receive and transfer the light emitted from a multiplicity of LED light sources 507. This light is focused onto the fiber optics face and is reflected through the fibers to the distal end of the camera lens system 534. The CCD signal wire bundle 506 passes through the light focusing enclosure 502 and is coiled into a service loop to take up the twisting of the wire bundle 506.

As in the other embodiments described herein, a thumb-rotation wheel or similar mechanism can be used in connection with a pair of opposing cables to put one of the cables in tension and to relax the opposing cable. The tension causes the flexible distal end portion 530 to bend in proportion to the force applied to the cables.

The entire assembly is sterilizable, for example, by steam autoclave or sterile soak solutions.

In another embodiment, the expensive CCD camera is replaced by a low-cost digital camera chip available using CMOS technology, the general features of which may be in accordance with conventional CMOS technology. This, combined with a low-cost LED illumination source and the other low-cost molded plastic components, position the camera to be disposable device and delivered sterile to the customer using EtO sterilization methods.

In another embodiment, the camera is reusable. For example, the camera can be reusable for a limited number of times and is referred to as a "reposable" device that is sterilized each time through the use of a sterile soaking solution.

In another embodiment, illustrated in FIGS. 26-31, the device is provided with a variable radius curvable end segment 414. The device 400 shown in FIG. 26 has a proximal end defining a handle 403, a distal end defining an operable end 405 of the device 400, and an elongate body member 406 extending therebetween. The operable end 405 is rotatable and can provide suction, as shown, for example, in FIG. 27. In some embodiments, the operable end 405 is in the form of a powered instrument blade.

An external rotational drive force may be connected to the device with coupler onto a bearing shaft 417 and a vacuum source can be connected via vacuum port 415. The handle 405 houses the control means for the degrees of freedom of the tip (three degrees provided by curvilinear bending of the distal flexible portion 414, rotation of the operable end 405, and rotation about the axis of the device). Tension steering cables 421 can be provided in the handle 403 to control the bend radius of the flexible portion 414. The flexible portion 414 can be in accordance with any of the embodiments described above, for example, it can be in the form of a single piece injection molded plastic made from materials chosen for the their bending fatigue resistance properties, e.g. urethane, nylon, santoprene, elastomers and the like. The design can include a series of vertebra 422 interconnected by beam-shaped webs as described herein. In other embodiments, the device can include a series of discreet vertebrae strung together over the cables 421. As the tension in one of the cables 421 increases, the vertebral geometries surrounding that cable move closer together, thereby placing the beam-shaped web 424 in a state of bending. The stress is distributed linearly over the distance between the neutral axis and the thickness of the beam. This improves the fatigue life of the beam-shaped webs 424, by avoiding the stress riser point loads that are common with a hinged geometry as opposed to a bending geometry. The molded piece can further contain an axial hole 426 through which a flexible drive tube 431 (FIG. 30) can be placed for the purpose of rotating the operable end, as well as holes (not shown for each tensioning cable 421).

An embodiment of the control means is shown in FIG. 29. The steering cables 421 are routed around strategically positioned bearing rods and terminated on the circumference of a rotational wheel 411 (which can be conveniently positioned for rotation by the thumb or forefinger). As the rotational wheel 411 is rotated, one of the pair of steering cables 421 is placed into tension. The other cable is slackened to extend over its elongated distance. A rotation knob 412 can be disposed so as to rotate (e.g. in bearing saddles 413) and can be conveniently disposed for rotation by a finger (e.g. forefinger) or the thumb. A rotation tube 431 can be anchored securely within the rotation knob 412, such that when the knob 412 is rotated, the tube 431 rotates as well. At the distal end of the device, this rotation translates into the rotation of the operable end 405. The tube 431 can be terminated at the proximal end of the device in a sealed housing 432 with seals 433 (e.g. o-ring seals). The seals 433 are provided to hold the vacuum in a vacuum chamber 444, without preventing rotation. The vacuum chamber 444 is interconnected with an external vacuum source through a flexible hose positioned over the vacuum port 415. A flexible rotational actuating cable 416 is terminated at the proximal end in the bearing shaft 417. The bearing shaft rotates in a shaft seal 418 which holds the vacuum of the vacuum chamber 444. The vacuum chamber 444 pulls fluid and resected tissue from the operable end 405, through the rotation tube 431, and out of the device through the vacuum port 415. To prevent the tissue from plugging the rotation tube pathway, a flexible rotational actuating cable 416 can be designed and disposed to rotate in a random, non-linear pattern to disrupt any tissue coagulation. This random, non-linear pattern can be kept unstable by varying the tension in the cables 421. For example, the actuating cable 416 can rotate within the limits of straight on the center line with high tension or in contact with the walls of the rotation tube 431 with low tension or even slight compression.

Figure 27A:
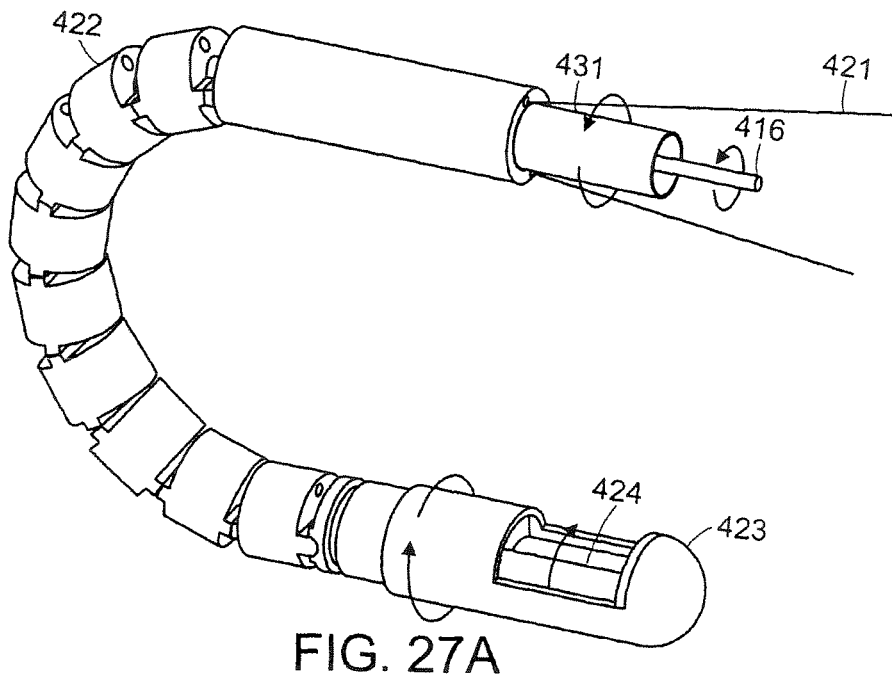
FIG. 27 shows side detailed views of the operable end of the device of FIG. 26.
Figure 27B:
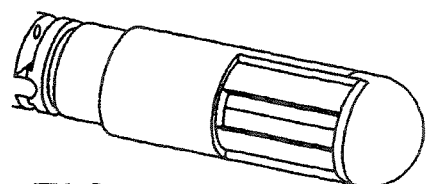
Figure 27C:
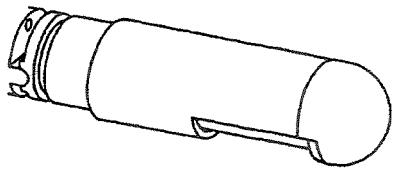
Figure 28A:
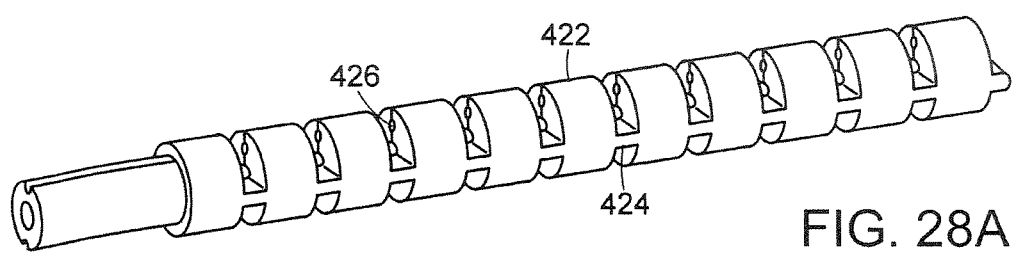
FIGS. 28A and B shows detailed views of one embodiment of the distal end segment of FIG. 26 in a straight position.
Figure 28B:
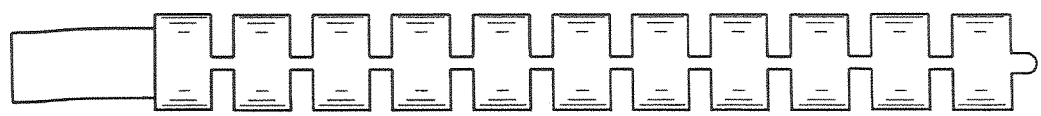
Figure 30:
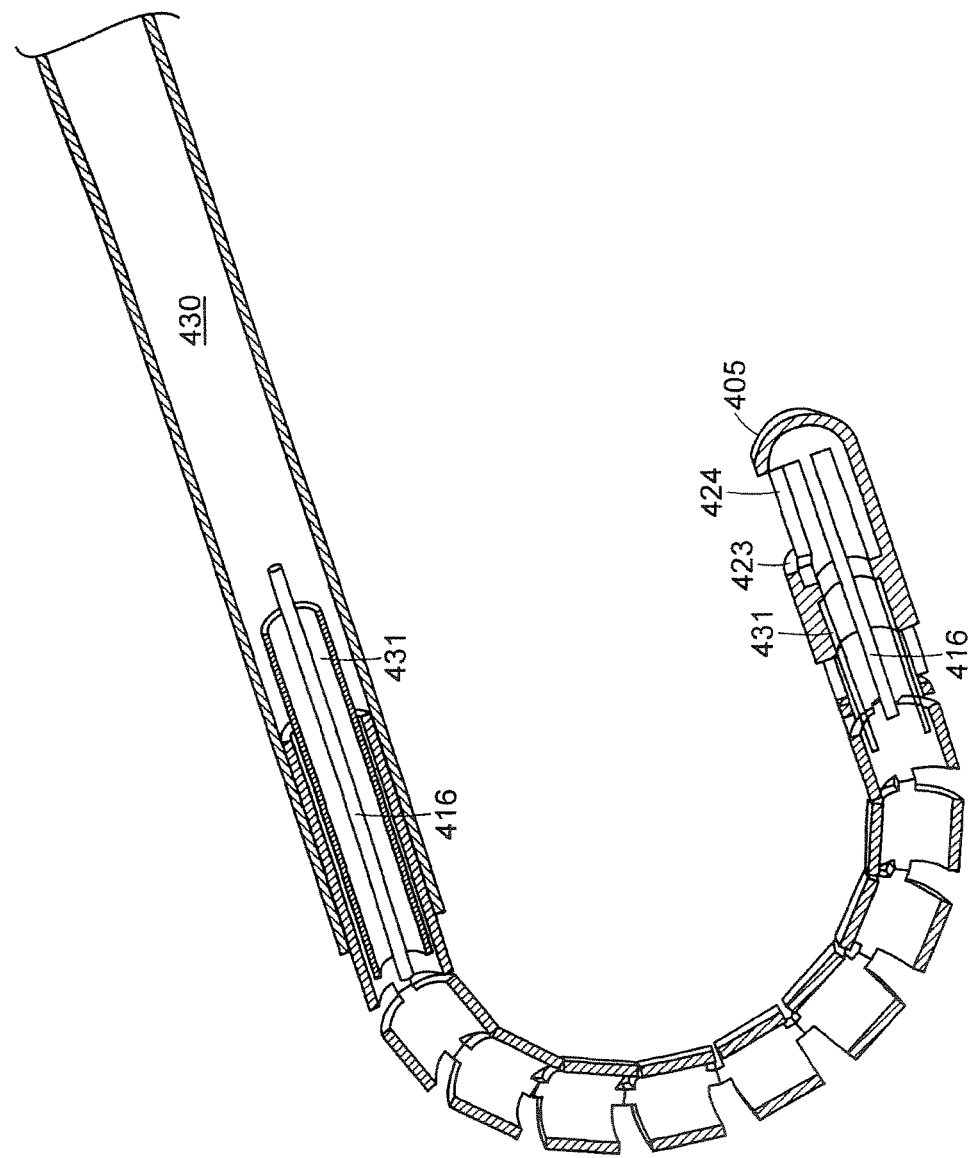
FIG. 30 shows a cross-sectional detailed view of a distal portion of the device of FIG. 26.

The flexible rotational actuating cable 416 is terminated distally in the cylindrical-shaped rotatable resecting piece 424 of the operable end 405 as shown in FIG. 30. This piece 424 rotates freely within a fixed resecting piece 423. Mating resecting pieces can be provided in a manner that cause tissue to be pulled by vacuum or suction through a window formed in the operable end 405 and into the cavity formed by the rotating piece 424 as shown, for example, in FIG. 27. The tissue is resected as it is entrapped between sharpened edges of the rotating piece 424 and the sharpened edges of the fixed piece 423. The rotation tube 431 is terminated distally into the fixed piece 423 in a manner that allows it to rotate about its arcuate axis, thereby exposing the rotating cutting window or windows only to the target surgical tissue as shown in FIG. 27.

Figure 31:
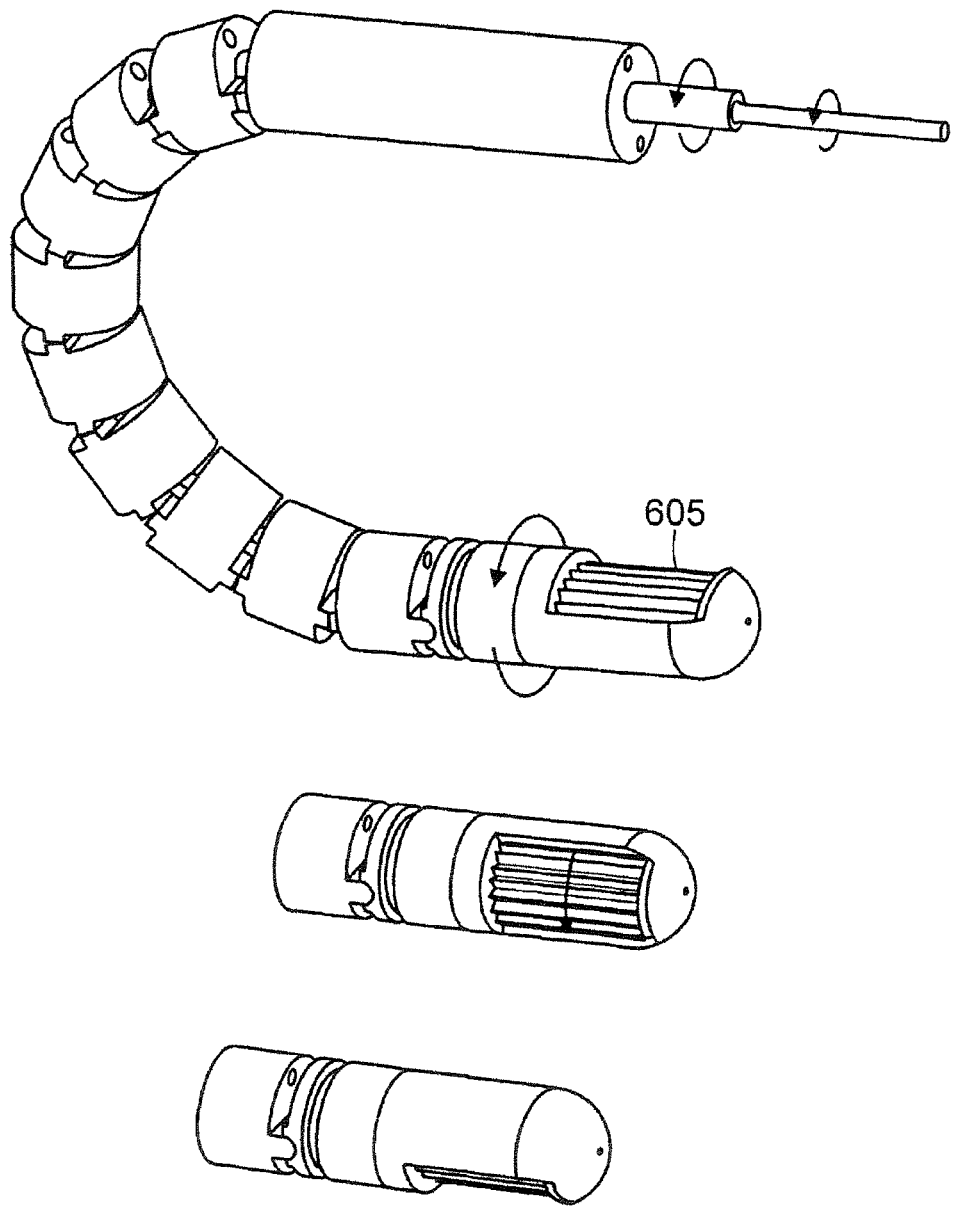
FIG. 31 shows views of the distal end and operable end of another embodiment of the invention.

Another embodiment is shown in FIG. 31. In this embodiment, the device is distally terminated in a burr 605 that is designed primarily for bone resection. Removal of the debris can be provided with or without suction as described herein.

The above embodiments address the need for a surgical instrument with a flexible tip that offers multiple degrees of freedom at its operable end to facilitate maneuverability and access. The various embodiments can make use of a variety of implements at the operable end, many of which require application of a significant compressive load at the instrument tip. The curvature of the flexible end segments of these instruments is generally controlled by tensioning cables or rods. In order for these systems to be effective in the application of a compressive load, the operable end must no be significantly deflected when the compressive force is applied. For example, if the end segment is bent to a 45 degree angle and a compressive load is applied during a punching operation, the force will tend to compress the end segment into a shorter length. This deflection may prohibit the force from being delivered to the tissue and no punching is accomplished.

In general, there is a trade-off between maneuverability (i.e., flexibility and controllability) and the ability to withstand a compressive load without significant deflection. The device 700 illustrated in FIGS. 32A and 32B overcomes this problem by providing an additional flexible member in the end segment of the instrument. The additional flexible member is structured so as to prevent the shortening of the end segment due to compressive loading. The device of this embodiment has a handle at its proximal end (not shown) to which is attached an elongate body member 706 to which is attached a curvable distal end segment 714 terminating at an operable end 705. The operable end 705 may comprise any of the previously discussed implements and may be rotatable relative to the curvable end segment 714. In the embodiment of FIGS. 32A and 32B, the operable end 705 comprises upper and lower grasping or cutting jaws similar to those of FIGS. 25A and 25C. For simplicity, only the lower jaw member is 742 is illustrated in FIGS. 32A and 32B. As in previous embodiments, the operation of the jaws of the operable end 705 may be controlled through the use of a cable (not shown) attached to the lower jaw and threaded back through the center of the curvable end segment 714 and the elongate body member 706.

The curvable end segment 714 of the device 700 includes an exterior flexible member 730 configured for flexibility and maneuverability and an interior flexible member 780 configured to prevent shortening and consequent deflection of the curvable end segment 714 when a compressive load is applied. The exterior flexible member 730 is attached to the distal end of the elongate member 706 in a manner similar to that of the end segments of the previous embodiments. The exterior flexible member 730 has a central passage formed therethrough. As discussed in more detail hereafter, this passage is sized and configured to accommodate a flexible rotation control drive shaft 708 and the interior flexible member 780. The exterior flexible member 730 may be further configured with one or more passages through which may be disposed tensioning cables 701 for controlling the bending of the exterior flexible member 730, and any cables required for operating the operable end 705.

Like the entire distal flexible portion of the previous embodiments, the exterior flexible member 730 may be formed as a plurality of vertebrae 731 interconnected by web members 732. The vertebrae 731 and web members 732 may be integrally formed as a single molded part. Alternatively, the exterior flexible member 730 may be formed from a plurality of vertebrae individually formed and pivotably attached to one another by hinges. As before, the interconnecting web 732 produces bending in accordance with the classic predictions of any beam subjected to moment forces on each end. This distributes the stress over the length of the beam (and, here, the length of the exterior flexible member 730) and relieves any point of localized stress that would result if the vertebrae 731 were hinged together at points. The vertebrae 731 can be generally cylindrical in shape, as shown, or of any other geometric shape.

As in previous embodiments a pair of tensioning cables 701 are attached to diametrically opposed points adjacent the distal end of the exterior flexible member 730. In the illustrated embodiment the tensioning cables 701 are attached to the distal-most vertebra 715. When a tension force is applied to one of the tension cables 701 (or if both cables 701 are under tension, when the tension force in one cable 701 than in the other cable 701), the vertebrae 731 are caused to compress on the side of the tensioned cable 701, thereby causing the interconnecting webs 732 to bend. The degree of bending is proportional to the differential tensile stress in the cables 701. Any of the previously discussed control and locking mechanisms for establishing and maintaining the tension force in the cables 701 (and thus a desired bending profile) may be used in conjunction with the device of this embodiment.

The device 700 includes a rotation control member 704 that is attached at its distal end to the operable end 705 and that is operably connected at its proximal end to a rotation control mechanism in the handle. The rotation control mechanism may be similar to the rotation control means discussed in connection with previous embodiments. The rotation control member 704 has an extension tube portion 707 rotatably disposed within the elongate body tube 706 and a flexible drive shaft portion 708 disposed through the central passage of the exterior flexible member 730. The flexible drive shaft portion 708 extends distally from the distal end of the extension tube portion 707. The extension tube portion 707 and the flexible drive shaft portion 708 each define a central passage that, together, form a rotation control member passage 709 that extends from the proximal end to the distal end of the rotation control member 704 to provide a passage for any cables required to operate the operable end 705. It will be understood that the extension tube portion 707 and the flexible drive shaft portion 708 may be formed as separate members that are permanently attached to one another or may be integrally formed as a single structure.

The flexible drive shaft portion 708 is fixedly attached to the operable end 705. It can therefore be seen that selective rotation of the rotation control member 704 will produce a rotation of the operable end 705 about the axis of the flexible drive shaft portion 708. When the flexible drive shaft portion 708 is straight, this axis is a linear axis and when the flexible drive shaft portion 708 is bent, this axis is an arcuate axis.

The interior flexible member 780 is formed as a spring-like member having a plurality of coils 781. The interior flexible member 780 is configured for slidable disposition within the central passage of the exterior flexible member 730 and with its own central passage for slidable and rotational disposition therethrough of the flexible drive shaft portion 708 of the rotation control member 704.

The interior flexible member 780 is sized and positioned so that when the exterior flexible member 730 is bent, the interior flexible member 780 is also bent and conforms to the arc established by the inner passage of the exterior flexible member 730. This, in turn, will cause the flexible drive shaft portion 708 of the rotational control member 704 to bend, conforming to the central passage of the interior flexible member 780. The interior flexible member 780 is further configured so that when it is bent, its distal end 782 engages a proximal surface of the operable end 705 and its proximal end 784 engages a distal surface of the extension tube portion 707 of the rotational control member 704.

The interior flexible member 780 is further configured so that when the flexible end segment 714 is in a straight, unbent configuration, the coils 781 are in a relaxed state in which there is no space between adjacent coils 781. As best seen in FIG. 32B, the interior flexible member 780 is also configured so that when it is bent, a radially inward (with respect to the arc established by the bend) portion of each coil 781 remains in contact with a radially inward portion of each adjacent coil 781. At the same time, a space is introduced between a radially outward portion of each coil 781 and a radially outward portion of each adjacent coil 781. In a particular embodiment, the coils 781 are substantially rectangular as illustrated in FIGS. 32A and 32B.

It can be seen that by maintaining contact between the coils 781 along their radially inward portions, a compression load may be transmitted from the operable end 705 through the coils 781 to the extension tube portion 707 of the rotational control member 704.

In operation, the tensioning cables 701 are used to bend the exterior flexible member 730 to take on a desired curvature. The size and configuration of the exterior member vertebrae 731 provides leverage so that the curvable end segment may be selectively curved with relatively little force on the tensioning cables 701. The slidably disposed interior flexible member 780 is forced to adopt a conforming curvature.

The device 700 of FIGS. 32A and 32B provides a combination of flexibility, maneuverability and resistance to deflection when a compressive load is applied at the operable end. As noted above, any of the previously described operable end implements may be used with this embodiment. The nested disposition of the two flexible members 730, 780, however, produces an effect that may compromise the integrity of the device 700 in some applications. As with any bending member, each of the flexible member 730, 780 has a neutral fiber (NF). The NF is an imaginary fiber through the bending member that neither undergoes elongation nor compression during bending. At any radius larger than that of the NF, the member expands and at any radius smaller than the NF, the member compresses. The configuration of the exterior flexible member 730 is such that its NF is essentially along the arcuate axis through its center. The configuration of the interior flexible member 780, however, is such that its NF is through its radially inward contacting portions. As a result, the NF of the interior flexible member 780 defines a shorter radius arc than does the NF of the exterior flexible member 730. Because their actual lengths remain unchanged when the distal end segment is curved, the difference in arc radius causes the interior flexible member 780 to protrude from the distal end of the exterior flexible member 730, thus potentially compromising the integrity of the device 700. The effect is illustrated by a comparison of the position of the operable end 705 relative to the distal end of the exterior flexible member 730 in the uncurved configuration of FIG. 32A and in the curved configuration of FIG. 32B. As shown in FIG. 32A, the operable end 705 and the distal end of the interior flexible member 780 extending some distance outward from the distal end of the exterior flexible member 730.

This effect may be countered as illustrated by the device 800 according to another embodiment of the invention, which is illustrated in FIGS. 33A and 33B. The device 800 is similar to the device 700 in most respects. It has a handle at its proximal end (not shown) to which is attached an elongate body member 806 to which is attached a curvable distal end segment 814 terminating at an operable end 805. The operable end 805 may comprise any of the previously discussed implements and may be rotatable relative to the curvable end segment 814. As shown in FIGS. 33A and 33B, the operable end 805 may comprises upper and lower grasping or cutting jaws similar to those of FIGS. 25A and 25C, For simplicity, only the lower jaw member is 842 is illustrated in FIGS. 33A and 33B. As in previous embodiments, the operation of the jaws of the operable end 805 may be controlled through the use of a cable (not shown) attached to the lower jaw and threaded back through the center of the curvable end segment 814 and the elongate member 806.

As in the previous embodiment, the curvable end segment 814 of the device 800 is formed from two flexible members: an exterior flexible member 830 and an interior flexible member 880 configured to prevent deflection of the curvable end segment 814 when a compressive load is applied. The exterior flexible member 830 is attached to the distal end of the elongate member 806 in a manner similar to that of the end segments of the previous embodiments. The exterior flexible member 830 has a central passage formed therethrough. This passage is sized and configured to accommodate a flexible rotation control drive shaft 808 and the interior flexible member 880. The exterior flexible member 830 may also be configured with one or more passages through which may be disposed tensioning cables 801 for controlling the bending of the exterior flexible member 830 and any cables required for operating the operable end 805.

The exterior flexible member 830 may be formed as a plurality of vertebrae 831 interconnected by web members 832. The vertebrae 831 and web members 832 may be integrally formed as a single molded part. Alternatively, the exterior flexible member 830 may be formed from a plurality of vertebrae individually formed and pivotably attached to one another by hinges. As before, the interconnecting web 832 produces bending in accordance with the classic predictions of any beam subjected to moment forces on each end. The vertebrae 831 can be generally cylindrical in shape, as shown, or of any other geometric shape.

As in previous embodiments a pair of tensioning cables 801 are attached to diametrically opposed points adjacent the distal end of the exterior flexible member 830. In the illustrated embodiment the tensioning cables 801 are attached to the distal-most vertebra 815. When a tension force is applied to one of the tension cables 801 (or if both cables 801 are under tension, when the tension force in one cable 801 than in the other cable 801), the vertebrae 831 are caused to compress on the side of the tensioned cable 801, thereby causing the interconnecting webs 832 to bend. The degree of bending is proportional to the differential tensile stress in the cables 801. Any of the previously discussed control and locking mechanisms for establishing and maintaining the tension force in the cables 801 (and thus a desired bending profile) may be used in conjunction with the device of this embodiment.

The device 800 includes a rotation control member 804 that is attached at its distal end to the operable end 805 and that is operably connected at its proximal end to a rotation control mechanism in the handle. The rotation control mechanism may be similar to the rotation control means discussed in connection with previous embodiments. The rotation control member 804 is similar to that of the previous embodiment, having an extension tube portion 807 rotatably disposed within the elongate body tube 806 and a flexible drive shaft portion 808 disposed through the central passage of the exterior flexible member 830. The extension tube portion 807 and the flexible drive shaft portion 808 each define a central passage that, together, form a rotation control member passage 809 that extends from the proximal end to the distal end of the rotation control member 804. As before, the flexible drive shaft portion 808 may be formed as separate members that are permanently attached to one another or may be integrally formed as a single structure.

The flexible drive shaft portion 808 is fixedly attached to the operable end 805. It can therefore be seen that selective rotation of the rotation control member 804 will produce a rotation of the operable end 805 about the axis of the flexible drive shaft portion 808. When the flexible drive shaft portion 808 is straight, this axis is a linear axis and when the flexible drive shaft portion 808 is bent, this axis is an arcuate axis.

The interior flexible member 880 is substantially similar to the interior flexible member 780 of the previous embodiment. The interior flexible member 880 is sized and positioned so that when the exterior flexible member 830 is bent, the interior flexible member 880 is also bent and conforms to the arc established by the inner passage of the exterior flexible member 830. This, in turn, will cause the flexible drive shaft portion 808 of the rotational control member 804 to bend, conforming to the central passage of the interior flexible member 880. The interior flexible member 880 is further configured so that when it is bent, its distal end 882 engages a proximal surface of the operable end 805 and its proximal end 884 engages a distal surface of the extension tube portion 807 of the rotational control member 804.

The interior flexible member 880 is further configured so that when the flexible end segment 814 is in a straight, unbent configuration, the coils 881 are in a relaxed state in which there is no space between adjacent coils 881, As best seen in FIG. 33B, the interior flexible member 880 is also configured so that when it is bent, a radially inward (with respect to the arc established by the bend) portion of each coil 881 remains in contact with a radially inward portion of each adjacent coil 881. At the same time, a space is introduced between a radially outward portion of each coil 881 and a radially outward portion of each adjacent coil 881. In a particular embodiment, the coils 881 are substantially rectangular as illustrated in FIGS. 33A and 33B.

As in the previous embodiment, the tensioning cables 801 are used to bend the exterior flexible member 830 to take on a desired curvature. The size and configuration of the exterior member vertebrae 831 provides leverage so that the curvable end segment may be selectively curved with relatively little force on the tensioning cables 801. The slidably disposed interior flexible member 880 is forced to adopt a conforming curvature.

To prevent the protrusion of the interior flexible member 880 from the distal end of the exterior flexible member 830, the device 800 incorporates a biasing mechanism 890 that serves to bias the rotation control member 807 toward the proximal end of the elongate outer member 806. The rotation control member 807 transfers this biasing force to the operable end 805 to assure that when the flexible end segment 814 is bent, the operable end 805 stays in contact with the distal end of the exterior flexible member 830, As in the previous embodiment, the difference in NF between the two flexible members when the flexible end segment 814 is bent results in an excess length of the interior flexible member 880. As a result of the biasing force, however, the proximal end 884 of the interior flexible member 880 is forced to move in the proximal direction so that the excess length is drawn into the elongate body member 806.

In the embodiment illustrated in FIGS. 33A and 33B, the biasing mechanism 890 includes a helical spring 892 disposed circumferentially around the rotation control member 807 within the interior of the elongate outer member 806. The rotation control member 807 is formed with an inwardly extending tab 894 or other stopping mechanism that engages the distal end of the spring 892. The rotation control member 807 is formed with an outwardly extending circumferential flange 896 or other structure for engaging the proximal end of the spring 892. As shown in FIG. 33A, when the distal end segment 814 is in an uncurved configuration, the spring 892 is in a relatively compressed state. As shown in FIG. 33B, when the distal end segment 814 is curved, the effective length of the interior flexible member 880 is greater than the effective length of the exterior flexible member. However, the biasing force of the spring 892 acting on the rotation control member 807 keeps the operable end 805 in contact with the exterior flexible member 830 and causes the interior flexible member 880 to be withdrawn in the proximal direction.

It will be understood that the biasing mechanism 890 is not limited to use in conjunction with the vertebrate flexible members of the illustrated embodiment, but could be used in conjunction with any elongate surgical instrument embodiment of the invention that has a curvable end segment with two nested flexible members having different neutral fiber lengths when the curvable end segment is curved.

Thus, alternate embodiments can be contrived as required by the customer. The handles can be reusable and sterilizable. The operable ends can be single-use sterile disposable elements, or they can be reusable and sterilizable. If desired, the entire device can be disposable.

For each of the various types of devices and operable ends, individual devices can be provided. In other embodiments, one or more devices can be provided with a variety of interchangeable operable ends. Thus, for example, a single base device can be provided with interchangeable operable ends ranging from the various stationary operable ends (e.g. scalpel), movable operable ends (e.g. scissors, dissectors, clamps), RF operable ends, and visualization operable ends. In such embodiments, the base device can include at least the handle portion of the device including the various actuation mechanisms for actuating operable end arms or jaws, actuating RF electrodes, and actuating the cameras. These actuation mechanisms can be used as applicable to each operable ends and can be enabled/disabled based on the operable end attached to the device. The base device can further include an elongate body member, in the form of an inner and outer body member or not, with the interchangeable portion being the distal, operable end. Thus, in such embodiments, the base device would be provided with a plurality of operable ends that can be removably and interchangeably attached to the elongate body member/inner body member. In other embodiments, the base device includes the handle and the outer body member, with the interchangeable portion being the inner body member having the operable end attached thereto. In such embodiments, the base device would be provided with a plurality of inner body members, each having a different operable end attached thereto. Further, each inner body member could be provided with the appropriate actuation mechanism where required (e.g. electrical and insulation mechanisms housed therein). In other embodiments, the base device includes the handle, with the elongate body member/inner and outer body member being the interchangeable portion. In such embodiments, the base device would be provided with a plurality of elongate body members/inner and outer body members having different operable ends attached thereto.

Further, interchangeable operable ends in the form of a multiplicity of electrocautery tips can be provided to make available the numerous shaped electrodes that are used by surgeons. For example, mono-polar tips have no moving parts can be provided as well as bi-polar tips which include a pair of movable electrode (jaws). In one embodiment, the device is in the form of a mono-polar device and the handle can be devoid of an operable end actuation mechanism discussed above.

In each of these embodiments, the interchangeable portion(s) are provided with a connection mechanism that mates with a connection mechanism on the base device. Conventional connection mechanisms that can provide repeat connection and removal between the removable interchangeable elements can be used in these embodiments (e.g. mating threaded portions and mating tabs and grooves).

In some embodiments, a single device is provided with a handle for performing grasping, cutting, etc. and electrocautery and, as such, a single handle can be provided for both types of procedures. A separate device can be provided for visualization. As such, the surgeon can use one handle for visualization and one handle for tissue manipulation and ablation.

For all of the embodiments, all or portions of the device can be reusable or disposed of. In some embodiments, removable and interchangeable distal ends, inner/outer body member(s), and/or elongate body members that can be reused or disposed of as desired.

Methods of the present invention comprise performing arthroscopic procedures using the present devices so as to visualize and access to the entire joint without switching cannulated access portals. These methods are performed with devices that flexibly move within the site of the procedure by use of a distended joint and a curvilinear segment. The devices are capable of being extended into the joint and curving at a radius required to visualize and access to the entire distended capsule volume and eliminates any "no see" zones. The devices also obviate the requirement that the devices be interchanged into more than one access portal to allow for the visualization of the entire joint. In one embodiment, the device is adapted for hip procedures and is adapted for extension into the hip joint approximately 3 inches and curving at a radius approximately equal to that of the femoral head.

During use, the handle or proximal end is positioned outside the body. At least the distal portion of the body member is positioned inside the joint capsule, for example, as shown in FIG. 9. In one embodiment, two incisions are made and a cannula is inserted through each incisions to provide access to the joint capsule. The elongate body member of one device having a visualization mechanism at its distal end is inserted through one cannula. The elongate body member of another device having an operable end (e.g. scissors, dissector, forceps, punch, etc) is inserted through the other cannula. The elongate body member of one or more of the devices are extended and provided in a curved profile to enhance access to the various parts of the joint. In one embodiment, the body member is provided as an inner and outer body member, and, once the outer body member is positioned within the joint capsule, the inner body member is extended outside of the outer body member and provided in a curved profile. The procedure is performed and the devices withdrawn through the cannula after they are returned to a straight profile. Such procedures can be used in any type of arthroscopic surgery, such as the hip.

In another aspect, the invention generally relates to a method for performing minimally invasive hip arthroscopic surgical procedures by providing a device comprising a handle at a proximal end, a flexible or curvable portion at the distal end, and an elongate body member extending therebetween. An operable end is further rotatably mounted at the distal end. The bend radius of the flexible or curvable portion can be controlled, for example, in two ways: (1) a fixed-radius curvable device having an inner member with an embedded pre-formed shape, pre-formed to the desire radius, can be slidably extended from its location within an outer body member until the desired protruding radius is achieved through the actuation of a mechanism within the handle, and (2) a variable radius device having a system of steering cables (or cable) embedded in an articulating flexible or curvable distal end segment can be tensioned by rotation of a cam-like actuator located in the handle to achieve the desired bend radius. In each case, the user can iteratively adjust the extension and the degree of bending to accurately position the operable end in the joint capsule. The method further comprises (i) positioning the flexible or curvable distal portion into a straight configuration either by retracting the pre-formed end segment into the straight outer member, or tensioning the system of opposing steering cables until the flexible or curvable distal end segment is straight; (ii) inserting the straight elongate member into the hip capsule; (iii) iteratively adjusting the degree of extension and the bend radius to position the operable end in the desired arcuate position through the manipulation of control mechanisms in the handle; (iv) iteratively adjusting the degree of rotation about the linear axis of the elongated body member; (v) adjusting the rotational position of the operable end about it's arcuate axis to the desired rotational orientation using control mechanisms in the handle; (vi) performing the intended procedure by actuating the operable end by, for example, tensioning a cable to the desired effect through the manipulation of control mechanisms in the handle; (vii) re-establishing the straight configuration of the flexible or curvable distal end segment and re-positioning the operable end into its closed position as required; and (viii) removing the device from the body.

The above-described method is particularly effective for devices that have a relatively long, flexible end segment and in devices having controls that are soft and iterative in nature for precise maneuverability. In many applications, however, devices with shorter, more robust, flexible tips may be desirable. Such devices may, for example, have a bending limit at or below 90 degrees. With such devices, a method of deployment other than the above-described iterative method may be preferable. This method may be employed using a sequence of "set-and forget" bending and rotation adjustments. More specifically, the surgeon may adjust the degree of bending for best access to the target tissue and then lock it in place. The surgeon may also selectively rotate the operable end of the device (e.g., grasping or cutting jaws) to the best angle of approach to the target tissue and then lock that in place. This will position the jaws (or other implement) of the operable end to punch or grasp or otherwise manipulate the target tissue in the desired way.

In a hip arthroscopy procedure, a typical sequence for using a steerable instrument with an operable end at the distal end of a curvable end segment in a method according to the invention would thus include the following sequence:
 (a) Placing the flexible end segment into a straight configuration;
 (b) Inserting the distal end of the device into the body and into the distended capsule;
 (c) Linearly translating the operable end into the capsule;
 (d) Adjusting the degree of bend of the flexible end segment and locking the position;
 (e) Adjusting the angle of rotation of the operable or visualization end and locking the position;
 (f) If necessary, making minor adjustments in position by translating and or rotating the handle of the device to allow engagement or visualization of the target tissue;
 (g) Performing the procedure; i.e. grasping, resecting, ablating, or otherwise surgically manipulating the target tissue or establishing a clear visual image of the target surgical area within the capsule;

Upon completion of the procedure, the device may be returned to its straight configuration and withdrawn. It will be understood that variations in the sequence may be made without departing from the spirit and scope of the invention. For example, the order in which the bending and rotation positions are established may be reversed.

Any of these methods can be expanded to include the interaction of two devices as describe herein by (i) providing a first portal in the posterolateral position and second portal in the anterolateral position; (ii) inserting a first device in the anterolateral position, the first device comprising a handle at a proximal end, an operable end comprising a visualization device at a distal end, a body member extending, and an operable end capable of being iteriively manipulated to translate, bend, rotate to achieve the desired position in the capsule and to actuate as required to achieve the desired field of view; (iii) inserting a second device in the posterolateral position, the second device comprising a handle at a proximal end, an operable end comprising a operative device at a distal end, a body member extending therebetween, and an operable end capable of being iteratively manipulated to translate, bend, and rotate to achieve the desire position ion the capsule and to actuate as required to achieve the desired surgical outcome Methods in accordance with these aspects can further include multiple operative devices. For example. After the visualization portal has been set up, it could be necessary to use one operative device to resect tissue (e.g. a punch), a second operative device to remove tissue and loose bodies, a third device to cauterize any remaining bleeding sites, etc.

The present invention also includes kits (not shown) that comprise one or more devices in accordance with the invention, that can be packaged in sterile condition. Such kits also may include one or more interchangeable distal ends, operable ends, body members (elongate body member, inner body member, outer body member) for use with the devices, and/or written instructions for use of the device(s) and/or the equipment. In some embodiments, the kit also can also include flexible and/or rigid access cannulas that are sealed against the saline distension pressure within the joint capsule and inserted using "safe access" trocars, mechanical flexation device(s) that mechanically distends the hip joint laterally as well as longitudinally along the line of action coincident with the center line of the femoral neck, and fluid management systems to control the flow and pressure of the saline in the hip capsule.

In one embodiment, the kit includes some combination of the following equipment: a curvilinear visualization device, a curvilinear instrument capable of mechanically manipulating tissue, such as a grasper, a punch, scissors, a clamp, a retractor, a powered instrument blade, a bone resection tool, or the like, and a curvilinear instrument capable of electrically manipulating tissue, such as a monopolar or bi-polar cautery, or the like. The visualization device, mechanical manipulating device and electrical manipulating device can be provided as two or more proximal ends or handles together with interchangeable body members having thereon a variety of visualization, mechanical, and electrical elements. In another embodiment, the visualization device, mechanical manipulating device and electrical manipulating device can be provided as two or more proximal ends or handles with attached body members together with interchangeable inner tubular members having thereon a variety of visualization, mechanical, and electrical elements. In another embodiment, the visualization device, mechanical manipulating device and electrical manipulating device can be provided as two or more proximal ends or handles with attached body members together with interchangeable distal operable ends in the form of a variety of visualization, mechanical and electrical operable elements. Thus, the desired visualization, mechanical or electrical device can be provided simply by interchanging the body member, tubular member or operable end.

The foregoing description of the invention is merely illustrative thereof, and it is understood that variations and modifications can be effected without departing from the scope or spirit of the invention as set forth in the following claims. For example, the curvilinear approach for the precise delivery of a multiplicity of operable ends has great utility beyond hip applications described herein, (e.g. knee and shoulder arthroscopy, as well as smaller joint arthroscopy). The smaller diameters of the device (e.g. approximately 3.5 mm for graspers and RF probes and approximately 4.0 mm for cameras) as well as the flexibility of each device also make it useful for other applications that require delicate visualization and tissue manipulation, including, but not limited to, laparoscopic cholecystectomies, appendectomies, hernia repair, bariatric gastric by-pass, and certain thoracic and spinal procedures.

What is claimed is:

1. A device for diagnostic or surgical procedures comprising:
    a tubular outer body member having a proximal end and a distal end;
    a handle attached to the proximal end of the tubular outer body member;
    a flexible distal end segment extending from the distal end of the tubular outer body member, the flexible distal end segment having an axial end segment passage formed therethrough;
    first and second cables disposed so that a first portion of each cable is disposed within the tubular outer body member and a second portion of each cable is disposed within the flexible distal end segment, each cable having a distal end attached to an attachment point of the flexible distal end segment on its outer surface adjacent its distal end, the attachment points of the first and second cables being diametrically opposed so that when tensile forces are applied to one or both of the cables, a difference in the tensile force applied to the two cables causes the flexible distal end segment to bend;
    a rotation control member comprising:
        an extension tube portion rotatably disposed within the tubular outer body member;
        a flexible drive shaft portion attached to and extending distally from a distal end of the extension tube portion for rotation therewith, at least a portion of the flexible drive shaft portion being rotatably and slidably disposed within the axial end segment passage so as to take on a profile of the flexible distal end segment while being rotational therein; and
        an operable end attached at a distal end of the flexible drive shaft portion for rotation therewith, the flexible drive shaft portion being selectively rotatable to establish a desired rotational orientation of the operable end relative to the flexible distal end segment, the operable end having at least two operating states,
    wherein the extension tube portion is operably connected to a rotation control mechanism housed in the handle, the rotation control mechanism being configured to allow selective and endless rotation of the extension tube portion, the flexible drive shaft portion and the operable end while the flexible distal end segment remains rotationally fixed, and
    wherein the operable end is connected to an actuation mechanism, and further wherein the actuation mechanism comprises a third cable longitudinally movably disposed within the flexible drive shaft portion, wherein movement of the third cable causes the operable end to change operating states,
    whereby the handle and the flexible tubular body are used in a first manipulation of the operable end, the first and second cables are used in a second manipulation of the operable end, the rotation control member is used in a third manipulation of the operable end, and the actuation mechanism is used in a fourth manipulation of the operable end, with each of said manipulations being independent of, and having no effect on, the other of said manipulations.

2. The device of claim 1 wherein the flexible distal end segment comprises a plurality of vertebrae.

3. The device of claim 2 wherein the plurality of vertebrae are interconnected by an integral web.

4. The device of claim 3 wherein the vertebrae and web are integrally formed as a single member.

5. The device of claim 1 further comprising:
    bending means attached to the flexible distal end segment for selectively bending the flexible distal end segment to a desired bending profile.

6. The device of claim 5 further comprising:
    profile locking means for locking the flexible distal end segment in the desired bending profile.

7. The device of claim 1 wherein the flexible distal end segment comprises:
    an exterior flexible member attached to the distal end of the outer body member, the exterior flexible member having an exterior member axial passage formed therethrough; and
    an interior flexible member having proximal and distal ends and defining the axial end segment passage, at least a portion of the interior flexible member being disposed within the exterior flexible member so as to take on a profile of the exterior flexible member.

8. The device of claim 7 wherein the interior flexible member is configured so that when the flexible distal end segment is bent, the distal end of the interior flexible member engages a surface of the operable end and the proximal end of the interior flexible member engages a surface of the rotation control member.

9. The device of claim 8 wherein the interior flexible member is further configured to transmit a compression load from the operable end to the rotation control member when the operable end is operated.

10. The device of claim 8 further comprising:
a biasing arrangement including a spring in engagement with the rotation control member and the tubular outer body member to bias the rotation control member in a proximal direction relative to the tubular outer body member.

11. The device of claim 7 wherein the interior flexible member is a flat coil spring.

12. The device of claim 11 wherein the biasing arrangement and the rotation control member are sized and configured so as to cause the operable end to maintain engagement with the distal end of the exterior flexible member through a predetermined range of flexible end segment bending profiles.

13. The device of claim 7 wherein the exterior flexible member comprises a plurality of vertebrae.

14. The device of claim 7 wherein each cable has a distal end attached to an attachment point of the exterior flexible member on its outer surface adjacent its distal end, the attachment points of the first and second cables being diametrically opposed so that when tensile forces are applied to one or both of the cables, a difference in the tensile force applied to the two cables causes the exterior flexible member to bend.

15. The device of claim 1 wherein the outer diameter of the rotation control member makes a close sliding fit with the inner diameter of the flexible distal end segment.

* * * * *